United States Patent
Hu et al.

(10) Patent No.: US 12,325,676 B2
(45) Date of Patent: Jun. 10, 2025

(54) CATIONIC LIPID COMPOUND AND COMPOSITION FOR DELIVERY OF NUCLEIC ACIDS AND USE THEREOF

(71) Applicants: Shenzhen Rhegen Biotechnology Co., Ltd., Shenzhen (CN); Wuhan Rhegen Biotechnology Co., Ltd., Wuhan (CN)

(72) Inventors: Yong Hu, Shenzhen (CN); Yafei Li, Shenzhen (CN); Zhaoyu Hu, Shenzhen (CN)

(73) Assignees: Shenzhen Rhegen Biotechnology Co., Ltd., Shenzhen (CN); Wuhan Rhegen Biotechnology Co., Ltd., Wuhan (CN)

( * ) Notice: Subject to any disclaimer, the term of this patent is extended or adjusted under 35 U.S.C. 154(b) by 0 days.

(21) Appl. No.: 18/625,544

(22) Filed: Apr. 3, 2024

(65) Prior Publication Data

US 2024/0360072 A1 Oct. 31, 2024

Related U.S. Application Data

(63) Continuation of application No. PCT/CN2023/101290, filed on Jun. 20, 2023, and a continuation-in-part of application No. PCT/CN2022/143764, filed on Dec. 30, 2022, which is a continuation-in-part of application No. PCT/CN2022/143764, filed on Dec. 30, 2022.

(30) Foreign Application Priority Data

Jun. 20, 2022 (CN) .......................... 202210695125.5

(51) Int. Cl.
| | |
|---|---|
| C07C 229/12 | (2006.01) |
| A61K 9/1271 | (2025.01) |
| A61K 39/215 | (2006.01) |
| A61K 48/00 | (2006.01) |
| C07C 219/06 | (2006.01) |
| C07C 229/16 | (2006.01) |
| C07C 323/12 | (2006.01) |
| C07C 323/52 | (2006.01) |
| A61K 39/00 | (2006.01) |

(52) U.S. Cl.
CPC .......... *C07C 229/12* (2013.01); *A61K 9/1271* (2013.01); *A61K 39/215* (2013.01); *A61K 48/0033* (2013.01); *C07C 219/06* (2013.01); *C07C 229/16* (2013.01); *C07C 323/12* (2013.01); *C07C 323/52* (2013.01); *A61K 2039/53* (2013.01); *A61K 2039/55555* (2013.01); *C12N 2770/20034* (2013.01); *C12N 2770/20071* (2013.01)

(58) Field of Classification Search
CPC .............................. A61K 9/127; A61K 9/1271
See application file for complete search history.

(56) References Cited

U.S. PATENT DOCUMENTS

| | | |
|---|---|---|
| 2017/0119904 A1 | 5/2017 | Ansell et al. |
| 2019/0125839 A1 | 5/2019 | Frederick et al. |
| 2020/0368254 A1 | 11/2020 | Xu et al. |
| 2022/0081392 A1 | 3/2022 | Du et al. |
| 2023/0093138 A1 | 3/2023 | Huang et al. |

FOREIGN PATENT DOCUMENTS

| | | | |
|---|---|---|---|
| CN | 112979483 A | 6/2021 | |
| CN | 113185421 A | 7/2021 | |
| CN | 113999128 A | 2/2022 | |
| CN | 114380724 A | 4/2022 | |
| CN | 114773217 A | 7/2022 | |
| JP | 2001194776 A | 7/2001 | |
| WO | WO-2018170306 A1 * | 9/2011 | ........... A61K 31/573 |

OTHER PUBLICATIONS

International Search Report issued for counterpart Chinese patent application No. PCT/CN2023/101290 mailed on Oct. 5, 2023, 3 pages.
First Office Action and Search Report issued on Aug. 4, 2022 for counterpart Chinese patent application No. 202210695125.5.
Supplemental Search Report issued on Aug. 26, 2022 for counterpart Chinese patent application No. 202210695125.5.
Meng fanhao et al., China Medical Science and Technology Press, Pharmaceutical Chemistry, pp. 385-386.
Originating from the product catalog "STN Search Report 1" provided by Ukrorgsyntez Ltd. and others, the STN Search Platform Registry database.
CAS:"RN:66928-03-8", Registry, Nov. 16, 1984, CAS:"RN:66853-93-8", Registry, Nov. 16, 1984, CAS:"RN:66928-90-5", Registry, Nov. 16, 1984, CAS:"RN:65212-59-1", Registry, Nov. 16, 1984 CAS:"RN:65212-57-9", Registry, Nov. 16, 1984.

* cited by examiner

*Primary Examiner* — James W Rogers
(74) *Attorney, Agent, or Firm* — Hoffman Warnick LLC

(57) ABSTRACT

Provided in the present invention are a cationic lipid compound and a composition for delivery of a nucleic acid, and the use. The compound is represented by the following formula (I). Further provided in the present invention are the use of a nano-lipid particle using the compound as a key component in the delivery of a nucleic acid; a component containing a delivery carrier; a preparation method; and a usage method.

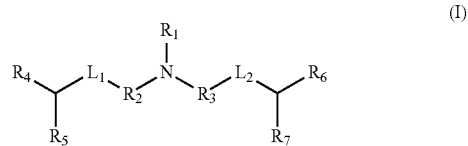

(I)

13 Claims, 4 Drawing Sheets

Specification includes a Sequence Listing.

CATIONIC LIPID COMPOUND AND COMPOSITION FOR DELIVERY OF NUCLEIC ACIDS AND USE THEREOF

SEQUENCE LISTING

The sequence listing contained in the electronic file titled "GAI22CN4962PB-US-Sequences.xml," created 8 Jul. 2024 and comprising 9 kb, is hereby incorporated herein.

FIELD OF TECHNOLOGY

The present disclosure relates to the field of lipid delivery carriers. Particularly, The present disclosure relates to a class of cationic lipid compounds which, when combined with other lipid components, are capable of forming drug-carrying nano-lipid particles, thereby enabling the delivery of nucleic acids from outside to inside of cells in vitro and in vivo. Specifically, the present disclosure relates to a cationic lipid compound and a composition for delivery of nucleic acids and use thereof.

BACKGROUND ART

Nucleic acid drugs replace, compensate, block or modify specific genes by introducing exogenous genes into target cells or tissues to achieve the purpose of treating and preventing diseases. They are relatively simpler to develop and produce, and have the advantages of short R&D cycle, high success rate in clinical development, and better plasticity for improvement. Nucleic acid vaccines, as one of the mainstays of COVID-19 prevention in recent years, have also proved their great potential in the market.

However, naked mRNA has a short circulation time in vivo, is easily degraded, and is difficult to enter target cells or target tissues. Therefore, improving the in vivo delivery efficiency of mRNA drugs is one of the key directions to improve the effectiveness of this class of products.

Currently, the most widely used delivery carriers for nucleic acid drugs are lipid nanoparticles, which have the characteristics of improving the efficacy of gene drugs as well as targeted delivery effects, and can protect nucleic acids from rapid degradation in vivo, so as to prolong the circulation time and enhance targeted delivery. The lipid nanoparticles are comprised of 2-4 lipid components, including cationic lipid compounds, 0-2 auxiliary lipids and 0-1 PEG lipids, in which cationic lipid compounds play a key role in encapsulation and release of nucleic acids. Therefore, it is crucial to develop novel, efficient and low-toxic cationic lipid compounds.

SUMMARY OF THE DISCLOSURE

The present disclosure provides a class of sulfur-containing cationic lipid compounds, including pharmaceutically acceptable salts thereof and stereoisomers or tautomers thereof. They are primarily used in combination with other lipid components in specific ratios, to form lipid nanoparticles for delivery of prophylactic or therapeutic agents, such as therapeutic nucleic acids.

Another object of the present disclosure is to provide methods for synthesizing this class of lipid compounds, by using readily available raw materials via a reaction route with mild conditions, high product yields, low instrumentation requirements and simplicity of operation.

In some examples, the therapeutic nucleic acids include plasmid DNA, messenger RNA, antisense oligonucleotides (ASON), micro RNA (miRNA), interfering RNA (miRNA), dicer substrate RNA, complementary DNA (cDNA).

The present disclosure also provides formulations and methods of use of such cationic lipid compounds when used in combination with other lipid components, and applications thereof in cellular and animal models.

In embodiments of the present disclosure, there is provided a cationic lipid compound having the following structure of formula (I):

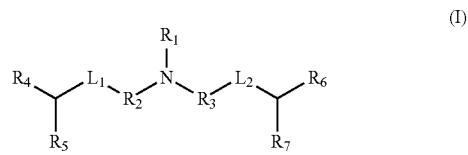

or a pharmaceutically acceptable salt, tautomer or stereoisomer thereof, wherein:

$L_1$ and $L_2$ are linkage bonds or divalent linkage groups, and the divalent linkage groups are each independently selected from any one of —C(=O)—, —OC(=O)—, —C(=O)O—, —OC(=O)O—, —O—, —S—, —S—S—, —C(=O)S—, —SC(=O)—, —N($R_8$)C(=O)—, —C(=O)N($R_8$)—, —N($R_8$)C(=O)O—, —OC(=O)N($R_8$)—, —SC(=O)N($R_8$)—, —N($R_8$)C(=O)S—, —C(=S)—, —SC(=S)— and —C(=S)S—; and $R_8$ is H or a $C_1$-$C_{12}$ alkyl;

$R_2$ and $R_3$ are each independently a substituted or unsubstituted $C_1$-$C_{18}$ linear alkylene or —$R_9$-$L_3$-$R_{10}$—; $R_9$ and $R_{10}$ are each independently a substituted or unsubstituted $C_1$-$C_{10}$ linear alkylene; and $L_3$ is O or S;

$R_4$, $R_5$, $R_6$ and $R_7$ are each independently hydrogen, or a substituted or unsubstituted $C_1$-$C_{30}$ aliphatic hydrocarbon group, or —$R_{11}$-$L_4$-$R_{12}$; $R_{11}$ and $R_{12}$, when present, are each independently a substituted or unsubstituted $C_1$-$C_{18}$ aliphatic hydrocarbon group; and $L_4$ is O or S;

at least one of $R_2$, $R_3$, $R_4$, $R_5$, $R_6$ and $R_7$ contains O or S;

$R_1$ is H, —$R_{13}$, —O$R_{13}$, —$R_{13}$—OH, —$R_{13}$—O$R_{14}$, —$R_{13}$—OC(=O)$R_{14}$, —$R_{13}$—NHC(=O)—$R_{14}$, —$R_{13}$—OCH$_3$ or —$R_{13}$—N($R_{14}$)($R_{15}$); $R_{13}$ is a $C_1$-$C_{12}$ linear alkyl or branched alkyl, $R_{10}$ and $R_{15}$ are each independently H or a $C_1$-$C_{12}$ linear alkyl, or $R_{10}$ and $R_{15}$ and the N atom attached thereto form a $C_3$-$C_{10}$ heterocyclic group.

In some specific embodiments of the present disclosure, $R_8$ is H or methyl.

In some specific embodiments of the present disclosure, $R_1$ is —$R_{13}$—OH or —$R_{13}$—N($R_{14}$)($R_{15}$), $R_{13}$ is a $C_1$-$C_{12}$ linear alkyl; and $R_{10}$ and $R_{15}$ are each independently a $C_1$-$C_{12}$ linear alkyl;

$R_2$ is a $C_1$-$C_{18}$ linear alkylene;

$L_1$ is —C(=O)S—, —SC(=O)—, —OC(=O)— or —C(=O)O—;

$R_4$ and $R_5$ are each independently a $C_1$-$C_{30}$ aliphatic hydrocarbon group;

$R_3$ is a $C_1$-$C_{18}$ linear alkylene;

$L_2$ is —C(=O)S—, —SC(=O)—, —OC(=O)— or —C(=O)O—;

$R_6$ is methyl or ethyl;

$R_7$ is —$R_{11}$-$L_4$-$R_{12}$; $R_{11}$ and $R_{12}$, when present, are each independently a substituted or unsubstituted $C_1$-$C_{18}$ aliphatic hydrocarbon group, and $L_4$ is O or S.

In some specific embodiments of the present disclosure, $R_{13}$ is a $C_1$-$C_8$ linear alkyl or branched alkyl, $R_{10}$ and $R_{15}$ are each independently H or a $C_1$-$C_5$ linear alkyl, or $R_{10}$ and $R_{15}$ and the N atom attached thereto form a $C_3$-$C_8$ heterocyclic group.

In some specific embodiments of the present disclosure, $R_2$ and $R_3$ are each independently a substituted or unsubstituted $C_1$-$C_{18}$ linear alkyl.

In some specific embodiments of the present disclosure, $R_2$ and $R_3$ are each independently a substituted or unsubstituted $C_1$-$C_{12}$ linear alkyl.

In some specific embodiments of the present disclosure, $R_4$, $R_5$, $R_6$ and $R_7$ are each independently H, or a substituted or unsubstituted $C_1$-$C_{18}$ aliphatic hydrocarbon group, or —$R_{11}$-$L_4$-$R_{12}$; $R_{11}$ and $R_{12}$, when present, are each independently a substituted or unsubstituted $C_1$-$C_{10}$ aliphatic hydrocarbon group, $L_4$ is O or S; at least one of $R_4$, $R_5$, $R_6$ and $R_7$ contains O or S, and at most two of them are hydrogen.

In some specific embodiments of the present disclosure, $R_4$, $R_5$, $R_6$ and $R_7$ in the structure of formula (I) are each independently H or an alkyl chain as described below, or each independently an ether group or a thioether group formed by replacement of any carbon atom in the alkyl chain below with O or S.

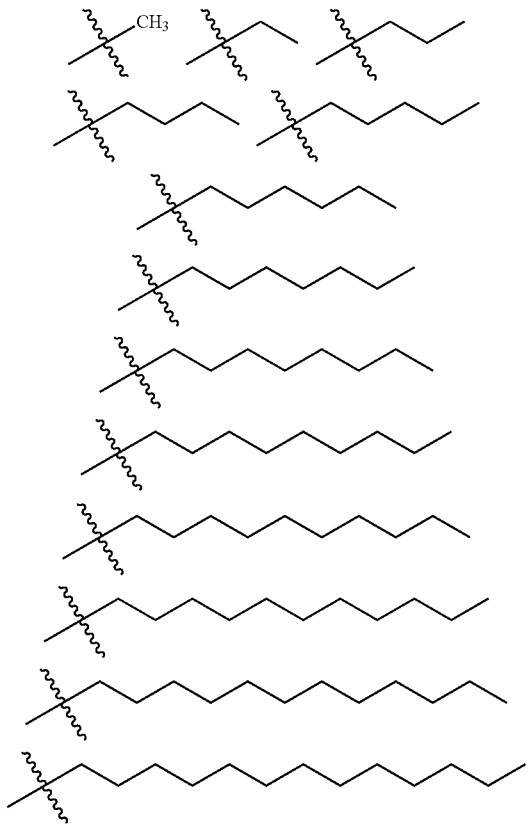

In some specific embodiments of the present disclosure, $R_1$ is —$R_{13}$—OH or —$R_{13}$—N($R_{14}$)($R_{15}$), $R_{13}$ is a $C_1$-$C_5$ linear alkyl, preferably, a $C_2$-$C_4$ linear alkyl; $R_{10}$ and $R_{15}$ are each independently a $C_1$-$C_{12}$ linear alkyl, preferably are each independently a $C_1$-$C_3$ linear alkyl;
 $R_2$ is a $C_2$-$C_{12}$ linear alkylene, preferably a $C_5$-$C_9$ linear alkylene, more preferably a $C_5$-$C_7$ linear alkylene;

$L_1$ is —C(=O)S—, —SC(=O)—, —OC(=O)— or —C(=O)O—;
$R_4$ and $R_5$ are each independently a $C_3$-$C_{13}$ aliphatic hydrocarbon group, preferably a $C_6$-$C_{10}$ linear alkyl, more preferably a $C_6$-$C_8$ linear alkyl;
$R_3$ is a $C_2$-$C_{10}$ linear alkylene, preferably a $C_3$-$C_7$ linear alkylene, more preferably a $C_5$-$C_7$ linear alkylene;
$L_2$ is —C(=O)S—, —SC(=O)—, —OC(=O)— or —C(=O)O—;
$R_6$ is methyl or ethyl;
$R_7$ is —$R_{11}$-$L_4$-$R_{12}$; $R_{11}$ is a $C_1$-$C_{10}$ alkyl, preferably a $C_1$-$C_3$ alkyl; $R_{12}$ is a $C_3$-$C_{13}$ alkyl, preferably a $C_6$-$C_{10}$ alkyl, more preferably a $C_6$-$C_8$ alkyl; $L_4$ is O or S.

According to some specific embodiments of the present disclosure, wherein:
$R_1$ is —$R_{13}$—OH, $R_{13}$ is a $C_{1-3}$ linear alkyl;
$R_2$ is a $C_5$-9 linear alkyl;
$L_1$ is —OC(=O)— or —C(=O)O—;
$R_4$ and $R_5$ are each independently a $C_6$-$C_{10}$ linear alkyl;
$R_3$ is a $C_5$-7 linear alkyl;
$L_2$ is —OC(=O)— or —C(=O)O—;
$R_6$ is methyl, ethyl or propyl;
$R_7$ is —$R_{11}$-$L_4$-$R_{12}$; $R_{11}$ is a $C_1$-$C_2$ alkyl; $R_{12}$ is a $C_3$-$C_{13}$ alkyl; $L_4$ is O or S.

According to some specific embodiments of the present disclosure, wherein: $R_1$ is —$R_{13}$—OH, $R_{13}$ is a $C_2$ linear alkyl;
$R_2$ is a $C_5$-7 linear alkyl; preferably a $C_7$ linear alkyl;
$L_1$ is —OC(=O)— or —C(=O)O—;
$R_4$ and $R_5$ are each independently a $C_8$ linear alkyl;
$R_3$ is a $C_5$-7 linear alkyl; preferably a $C_5$ linear alkyl;
$L_2$ is —OC(=O)—;
$R_6$ is methyl;
$R_7$ is —$R_{11}$-$L_4$-$R_{12}$; $R_{11}$ is a $C_5$-$C_8$ alkyl; $R_{12}$ is a $C_5$-$C_8$ alkyl; $L_4$ is O or S.

According to some specific embodiments of the present disclosure, wherein:
$L_1$ and $L_2$ are each independently selected from any one of —OC(=O)—, —C(=O)O—, —C(=O)S— and —SC(=O)—;
$R_2$ and $R_3$ are each independently a substituted or unsubstituted $C_1$-$C_{18}$ linear alkylene;
$R_4$, $R_5$ and $R_6$ are each independently H, or a substituted or unsubstituted $C_1$-$C_{30}$ aliphatic hydrocarbon group;
$R_7$ is —$R_{ii}$-$L_4$-$R_{12}$; $R_{11}$ and $R_{12}$, when present, are each independently a substituted or unsubstituted $C_1$-$C_{18}$ aliphatic hydrocarbon group, $L_4$ is O or S;
$R_1$ is H, —$R_{13}$—OH, —$R_{13}$—OCH$_3$ or —$R_{13}$—N($R_{14}$)($R_{15}$); $R_{13}$ is a $C_1$-$C_{12}$ linear alkyl or branched alkyl, $R_{10}$ and $R_{15}$ are each independently H or a $C_1$-$C_{12}$ linear alkyl, or $R_{10}$ and $R_{15}$ and the N atom attached thereto form a $C_3$-$C_{10}$ heterocyclic group.

According to some specific embodiments of the present disclosure, wherein:
$L_1$ and $L_2$ are each independently selected from any one of —OC(=O)—, —C(=O)O—, —C(=O)S— and —SC(=O)—;
$R_2$ and $R_3$ are each independently a substituted or unsubstituted $C_3$-$C_{10}$ linear alkylene;
$R_4$, $R_5$ and $R_6$ are each independently H, or a substituted or unsubstituted $C_1$-Cis aliphatic hydrocarbon group;
$R_7$ is —$R_{11}$-$L_4$-$R_{12}$; $R_{11}$ and $R_{12}$, when present, are each independently a substituted or unsubstituted $C_1$-$C_{18}$ aliphatic hydrocarbon group, $L_4$ is O or S;
$R_1$ is —$R_{13}$—OH; $R_{13}$ is a $C_1$-$C_6$ linear alkyl or branched alkyl.

According to some specific embodiments of the present disclosure, wherein:
- $L_1$ and $L_2$ are each independently selected from any one of —OC(=O)— and —C(=O)O—;
- $R_2$ and $R_3$ are each independently a substituted or unsubstituted $C_3$-$C_{10}$ linear alkylene;
- $R_4$, $R_5$ and $R_6$ are each independently H, or a substituted or unsubstituted $C_1$-$C_{18}$ aliphatic hydrocarbon group;
- $R_7$ is —$R_{11}$-$L_4$-$R_{12}$; $R_{11}$ and $R_{12}$, when present, are each independently a substituted or unsubstituted $C_1$-$C_{10}$ aliphatic hydrocarbon group, $L_4$ is O or S;
- $R_1$ is —$R_{13}$—OH; $R_{13}$ is a $C_1$-$C_6$ linear alkyl or branched alkyl.

According to some specific embodiments of the present disclosure, wherein:
- $L_1$ and $L_2$ are each independently selected from any one of —OC(=O)— and —C(=O)O—;
- $R_2$ and $R_3$ are each independently a substituted or unsubstituted $C_3$-$C_9$ linear alkylene;
- $R_4$, $R_5$ and $R_6$ are each independently H, or a substituted or unsubstituted $C_1$-$C_{12}$ aliphatic hydrocarbon group;
- $R_7$ is —$R_{11}$-$L_4$-$R_{12}$; $R_{11}$ and $R_{12}$, when present, are each independently a substituted or unsubstituted $C_1$-$C_9$ aliphatic hydrocarbon group, $L_4$ is O or S;
- $R_1$ is —$R_{13}$—OH; $R_{13}$ is a $C_1$-$C_5$ linear alkyl or branched alkyl.

In some specific embodiments of the present disclosure, the cationic lipid compound has one of the structures shown in the following table:

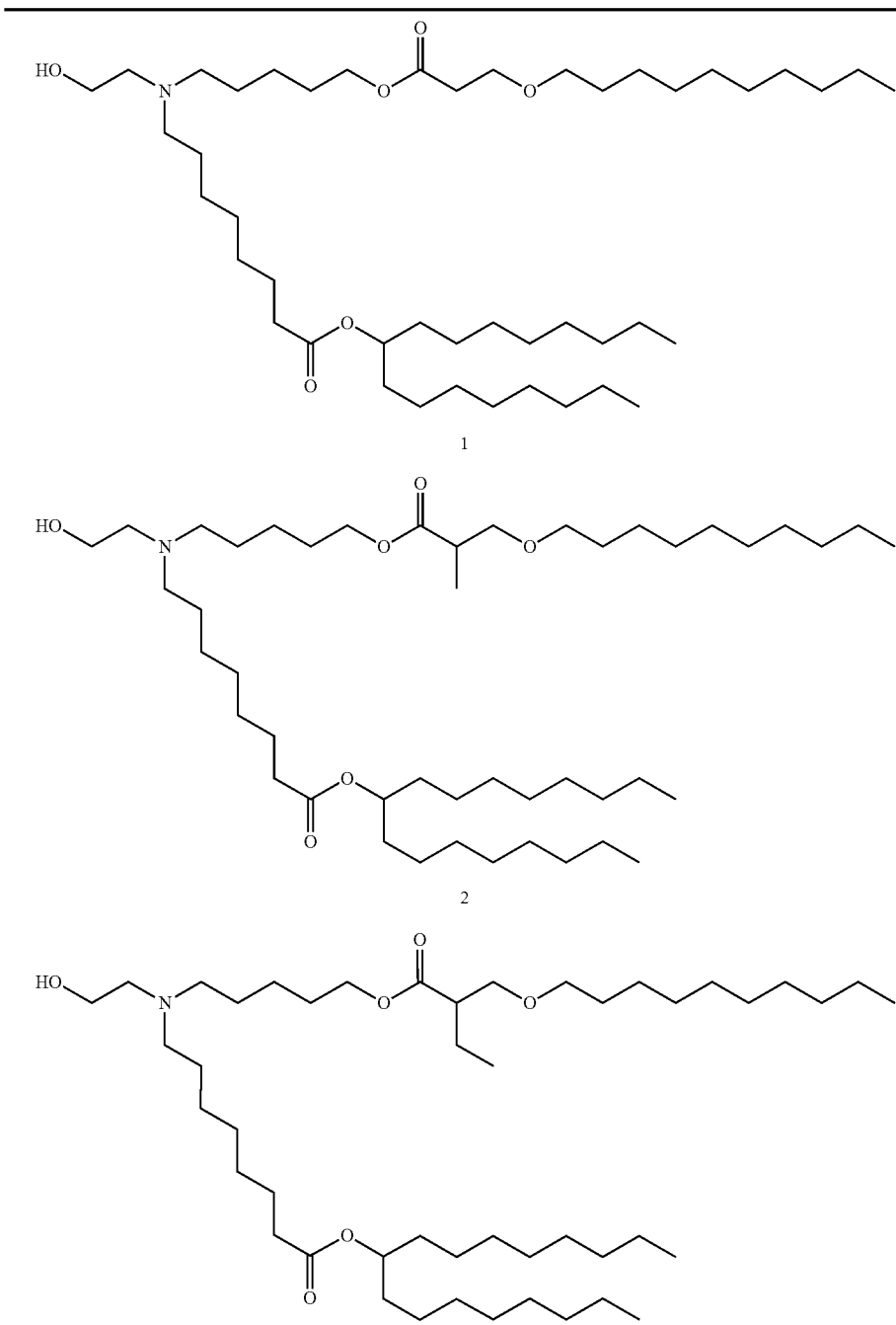

-continued
3
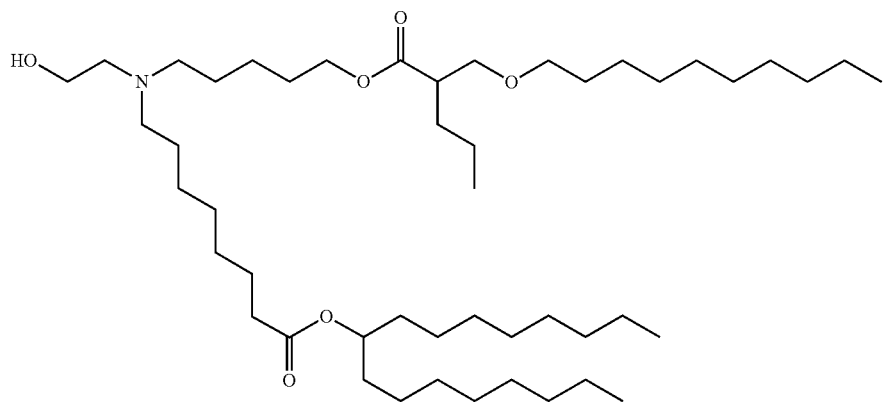 [SMILES: CCCCCCCCCCOCC(CCC)C(=O)OCCCCCN(CCO)CCCCCCCC(=O)OC(CCCCCCCC)CCCCCCCC]
4
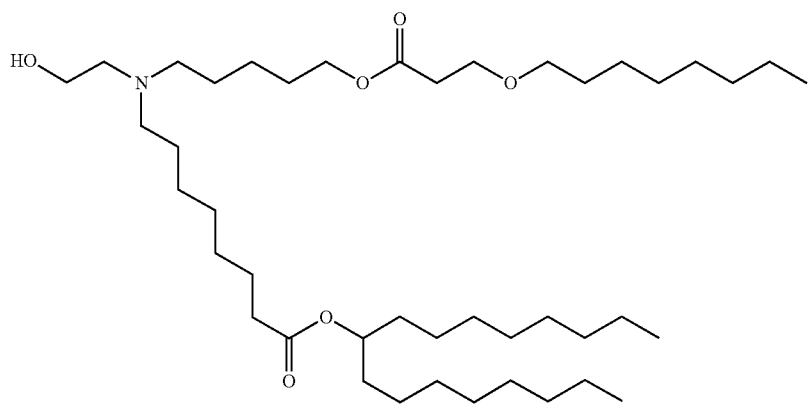 [SMILES: CCCCCCCCOCCC(=O)OCCCCCN(CCO)CCCCCCCC(=O)OC(CCCCCCCC)CCCCCCCC]
5
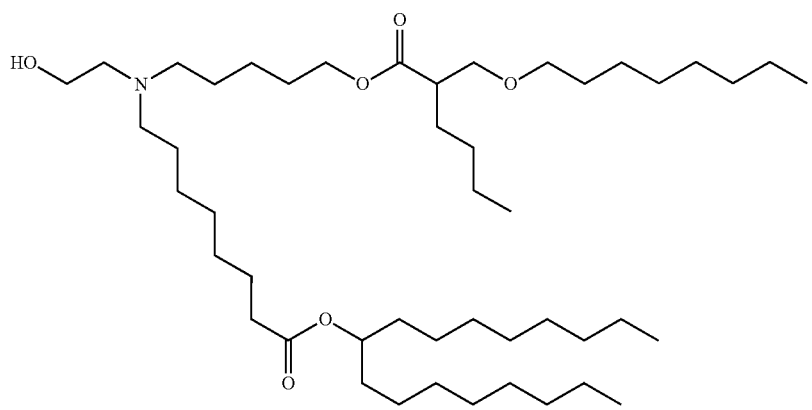
6

-continued
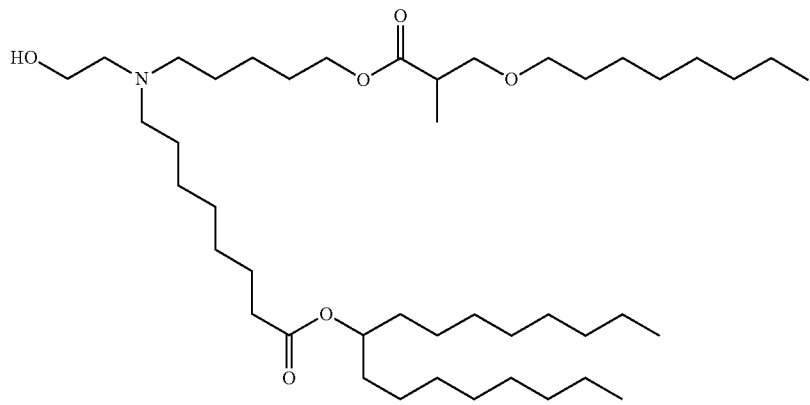 [SMILES: CCCCCCCCOCC(C)C(=O)OCCCCCN(CCO)CCCCCCCC(=O)OC(CCCCCCCC)CCCCCCCC]
7
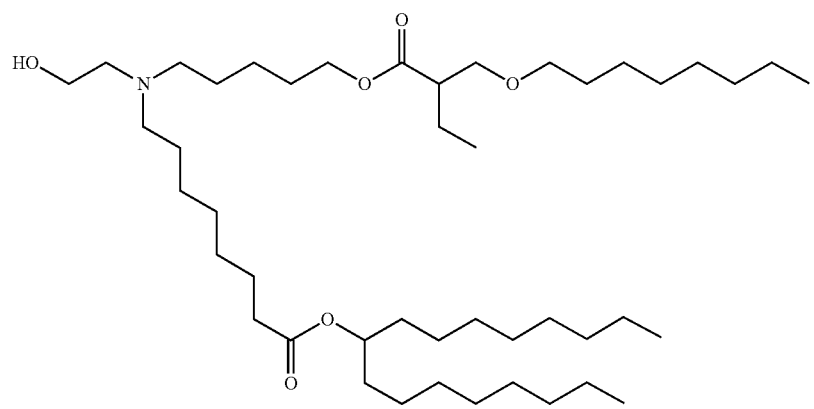 [SMILES: CCCCCCCCOCC(CC)C(=O)OCCCCCN(CCO)CCCCCCCC(=O)OC(CCCCCCCC)CCCCCCCC]
8
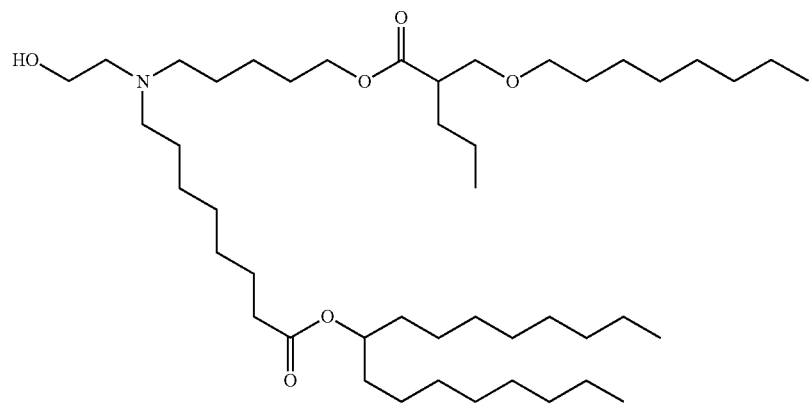 [SMILES: CCCCCCCCOCC(CCC)C(=O)OCCCCCN(CCO)CCCCCCCC(=O)OC(CCCCCCCC)CCCCCCCC]
9

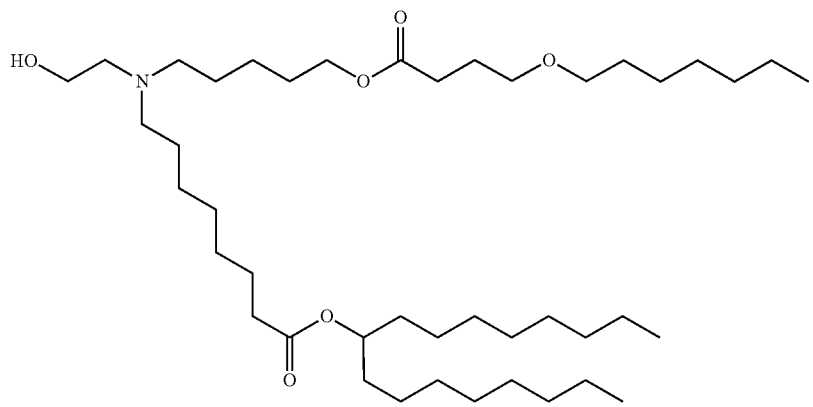 [SMILES: CCCCCCCCC(CCCCCCCC)OC(=O)CCCCCCCN(CCO)CCCCCOC(=O)CCCOCCCCCCC]
10
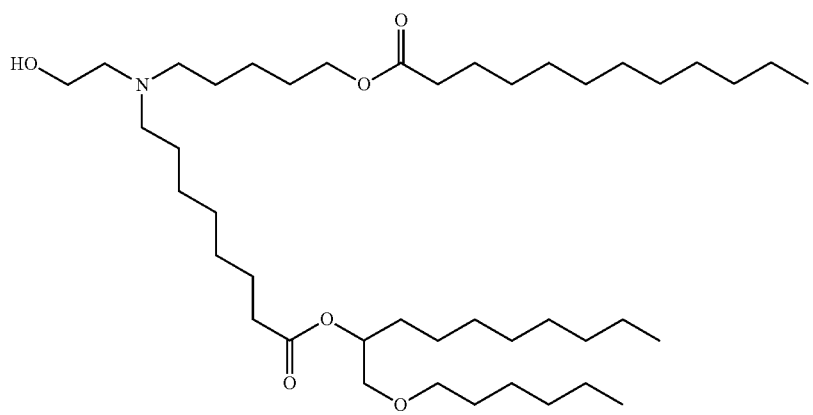 [SMILES: CCCCCCCCCCCC(=O)OCCCCCN(CCO)CCCCCCCC(=O)OC(CCCCCCCC)COCCCCCC]
11
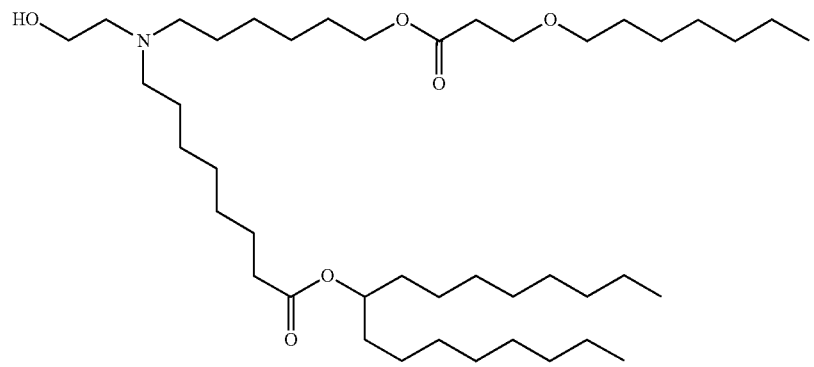 [SMILES: CCCCCCCCC(CCCCCCCC)OC(=O)CCCCCCCN(CCO)CCCCCCOC(=O)CCOCCCCCCC]
12

-continued
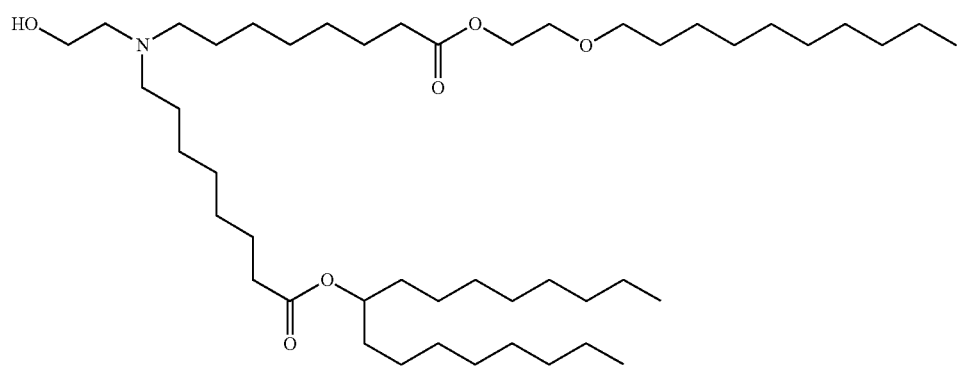 [SMILES: CCCCCCCCCCOCCOC(=O)CCCCCCCN(CCO)CCCCCCCC(=O)OC(CCCCCCCC)CCCCCCCC]
13
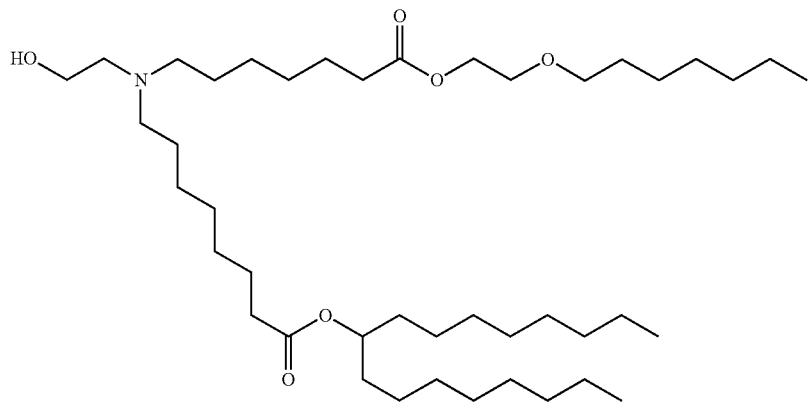 [SMILES: CCCCCCCCC(CCCCCCCC)OC(=O)CCCCCCCN(CCO)CCCCCCC(=O)OCCOCCCCCCC]
14
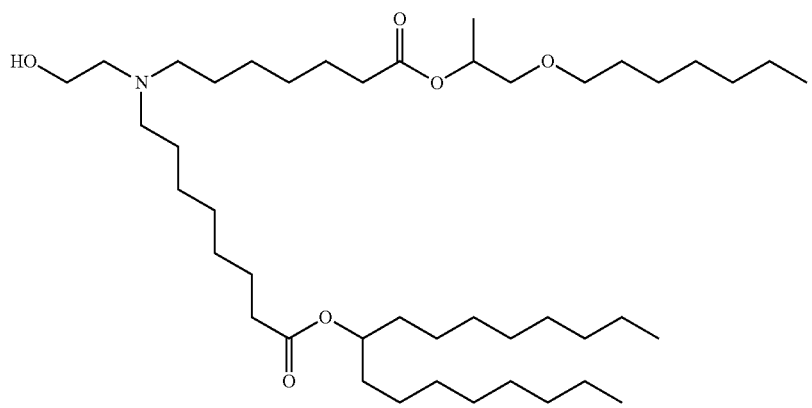
15

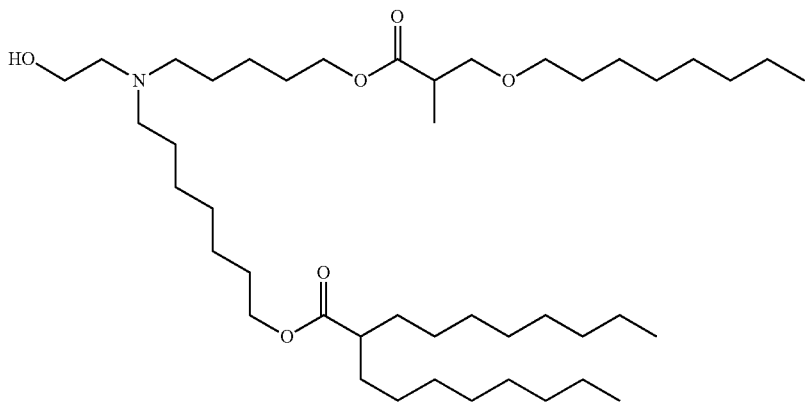 [SMILES: CCCCCCCCOCC(C)C(=O)OCCCCCN(CCO)CCCCCCCOC(=O)C(CCCCCCCC)CCCCCCCC]
16
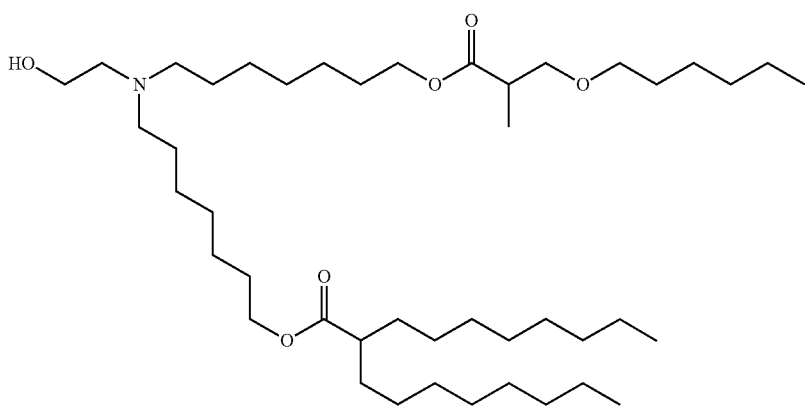 [SMILES: CCCCCCCCC(CCCCCCCC)C(=O)OCCCCCCCN(CCO)CCCCCCCOC(=O)C(C)COCCCCCC]
17
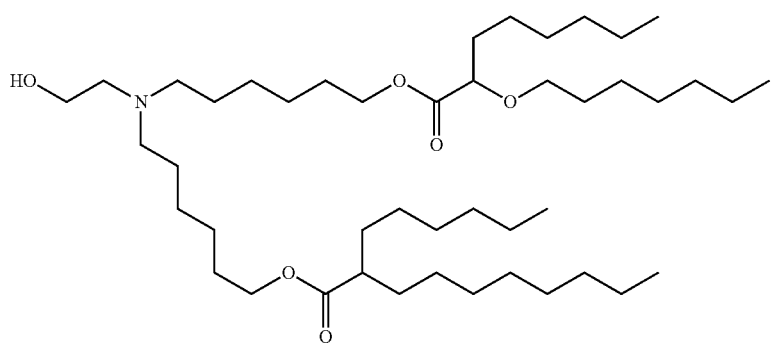 [SMILES: CCCCCCCCC(CCCCCC)C(=O)OCCCCCCN(CCO)CCCCCCOC(=O)C(CCCCCC)OCCCCCCC]
18

-continued
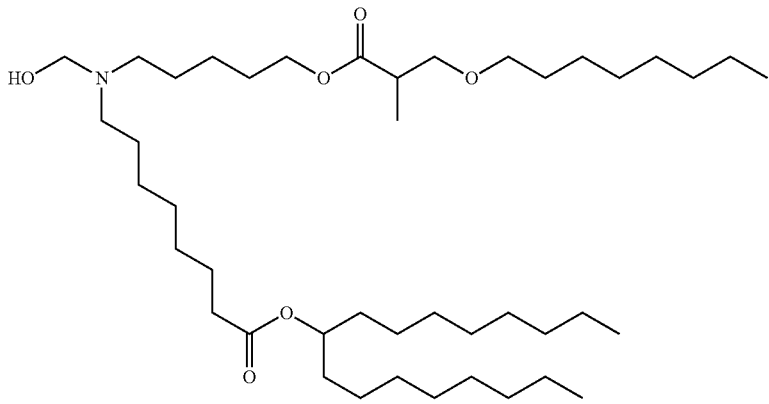
19
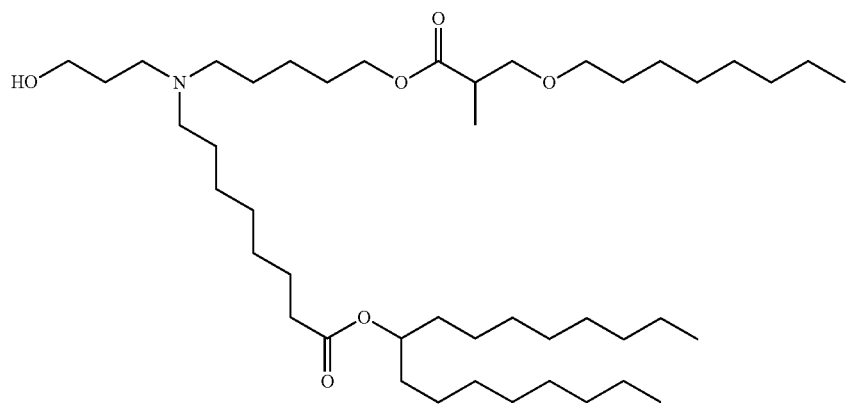
20
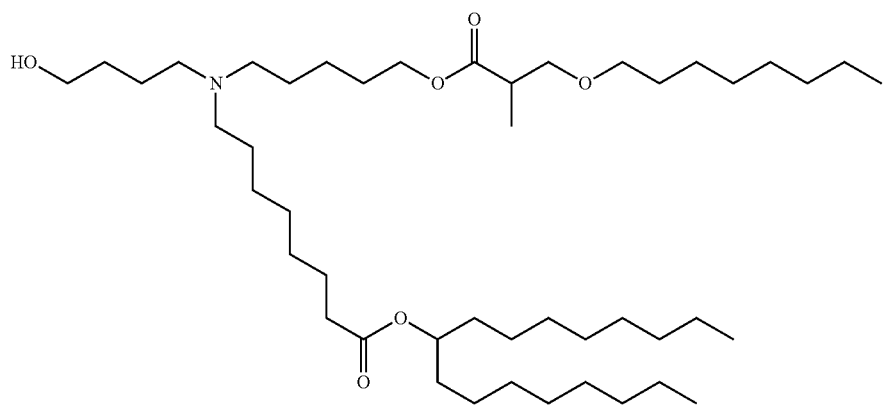 [SMILES: CCCCCCCCOCC(C)C(=O)OCCCCCN(CCCCO)CCCCCCCC(=O)OC(CCCCCCCC)CCCCCCCC]
21

-continued
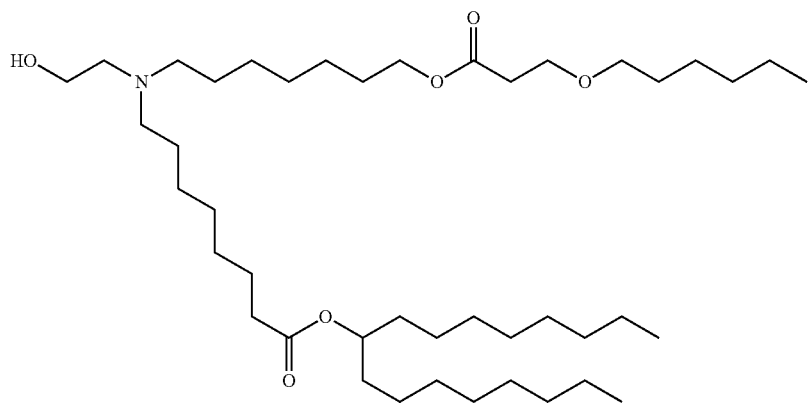 [SMILES: CCCCCCCCC(CCCCCCCC)OC(=O)CCCCCCCN(CCO)CCCCCCCOC(=O)CCOCCCCCC]
22
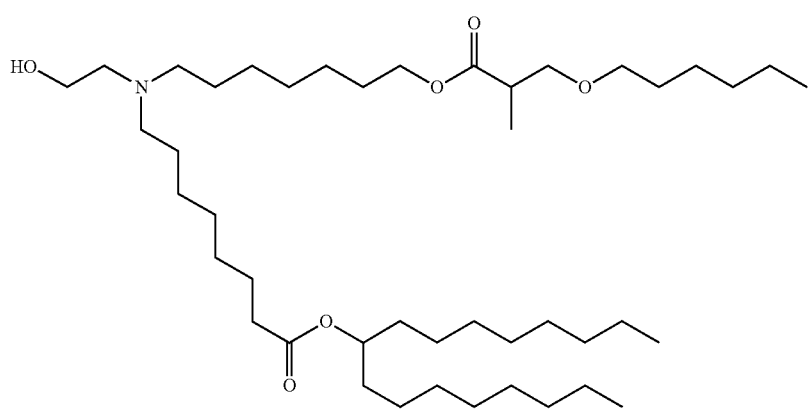
23
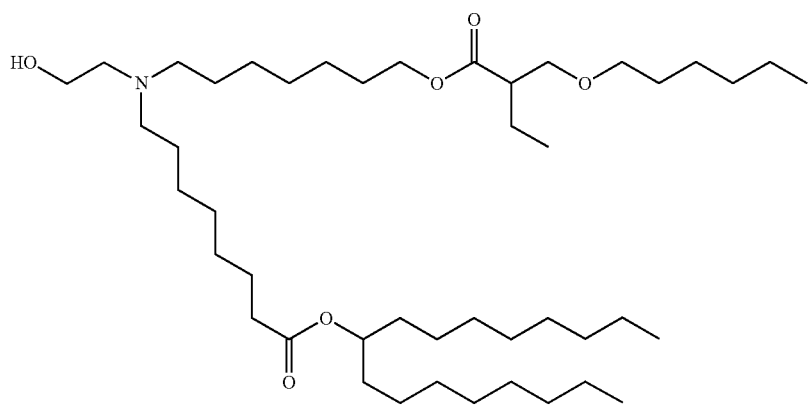
24

-continued
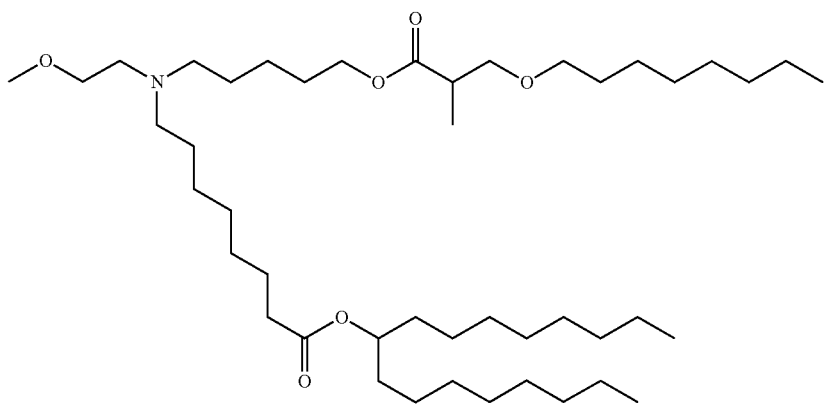
25
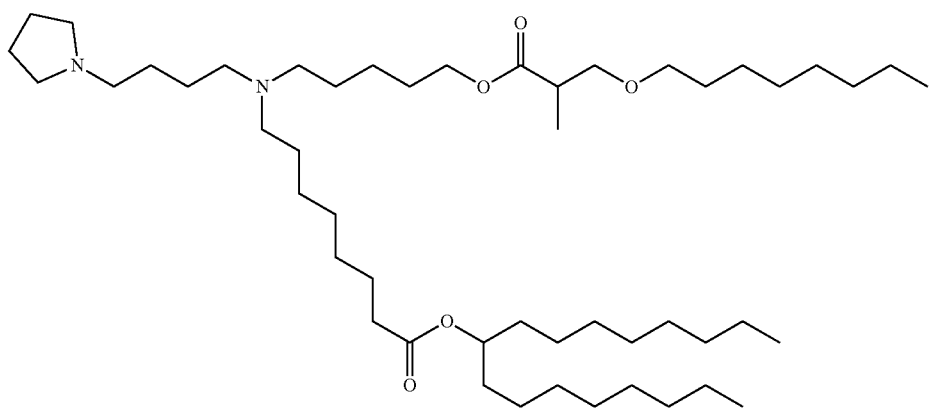 [SMILES: CCCCCCCCOCC(C)C(=O)OCCCCCN(CCCCCCCC(=O)OC(CCCCCCCC)CCCCCCCC)CCCCN1CCCC1]
26
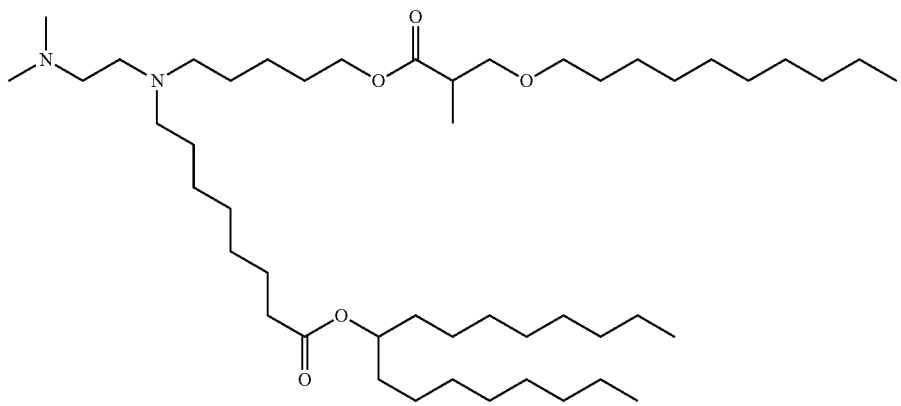
27

-continued
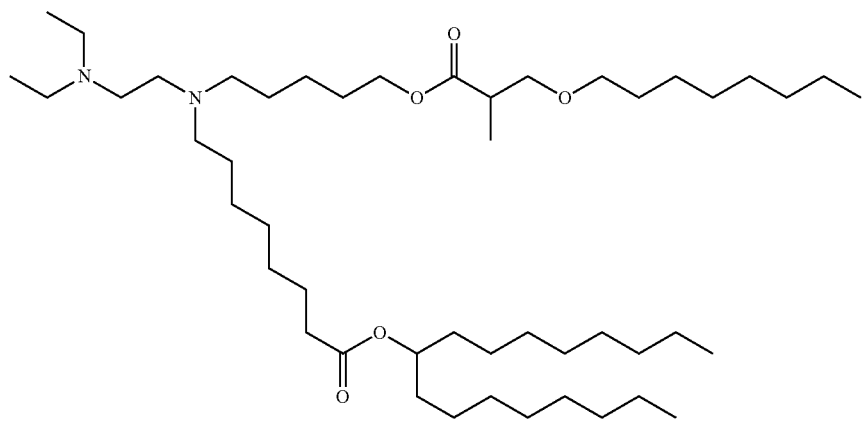 [SMILES: CCCCCCCCOCC(C)C(=O)OCCCCCN(CCCCCCCC(=O)OC(CCCCCCCC)CCCCCCCC)CCN(CC)CC]
28
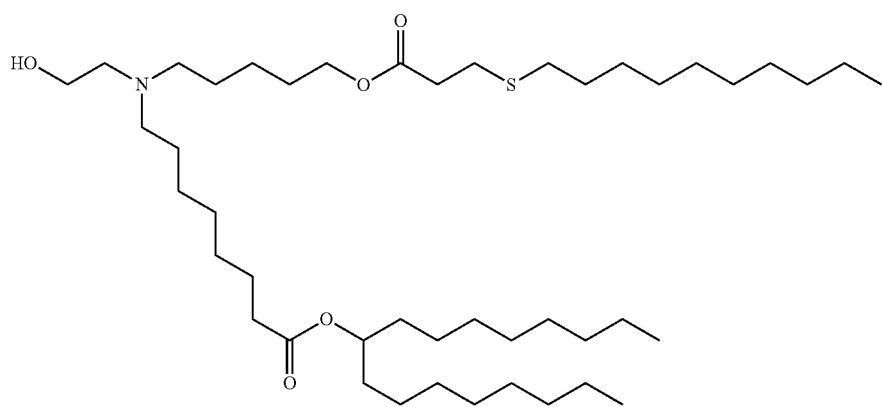 [SMILES: CCCCCCCCCCSCCC(=O)OCCCCCN(CCO)CCCCCCCC(=O)OC(CCCCCCCC)CCCCCCCC]
29
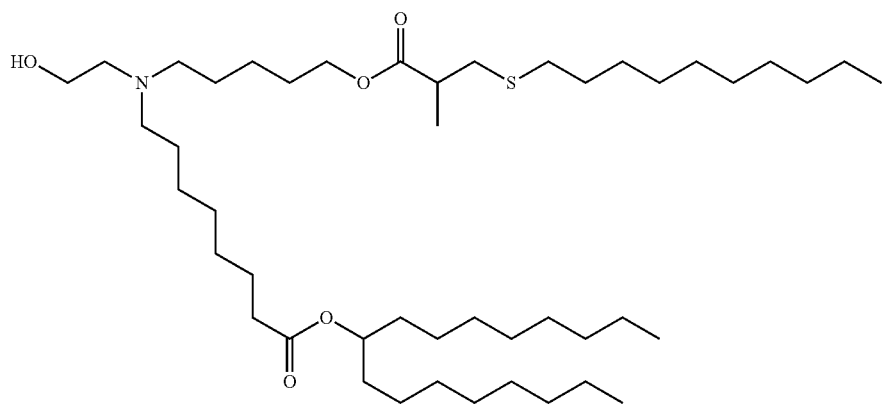 [SMILES: CCCCCCCCCCSCC(C)C(=O)OCCCCCN(CCO)CCCCCCCC(=O)OC(CCCCCCCC)CCCCCCCC]
30

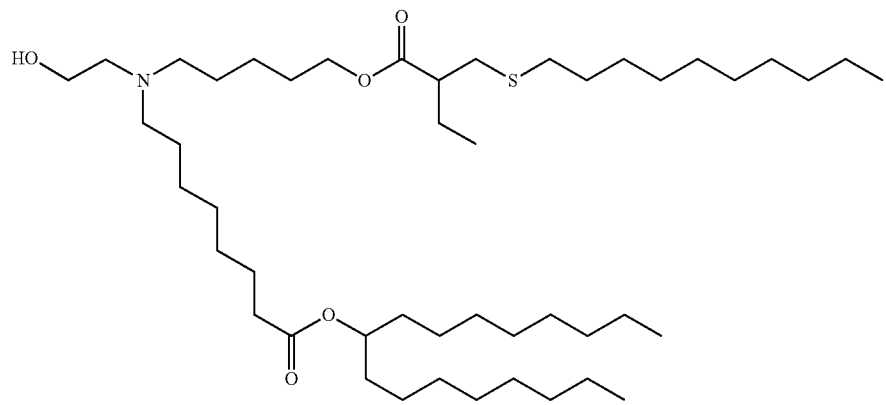 [SMILES: CCCCCCCCCCSCC(CC)C(=O)OCCCCCN(CCO)CCCCCCCC(=O)OC(CCCCCCCC)CCCCCCCC]
31
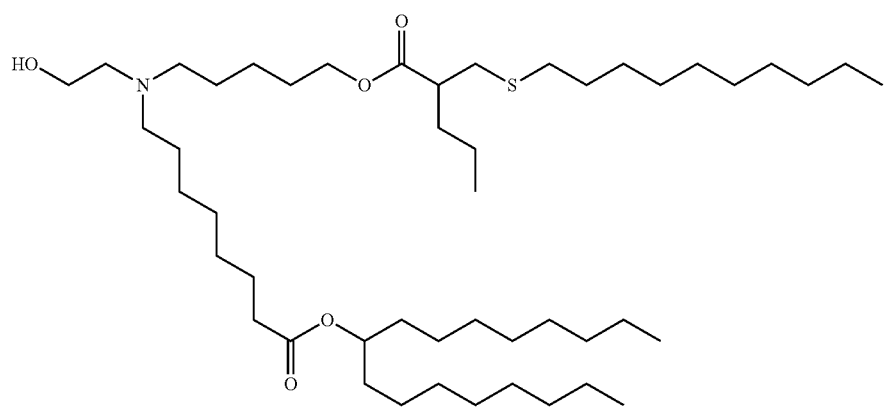 [SMILES: CCCCCCCCCCSCC(CCC)C(=O)OCCCCCN(CCO)CCCCCCCC(=O)OC(CCCCCCCC)CCCCCCCC]
32
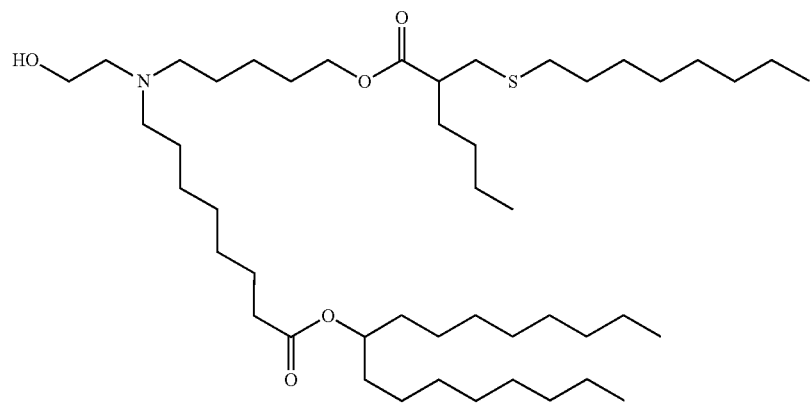 [SMILES: CCCCCCCCSCC(CCCC)C(=O)OCCCCCN(CCO)CCCCCCCC(=O)OC(CCCCCCCC)CCCCCCCC]
33

-continued
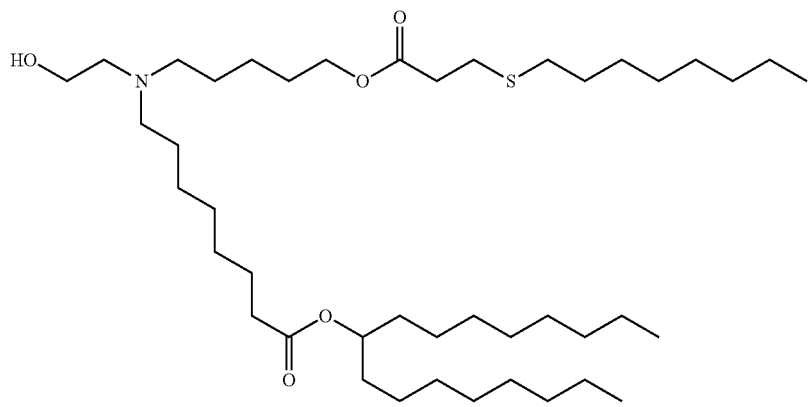
34
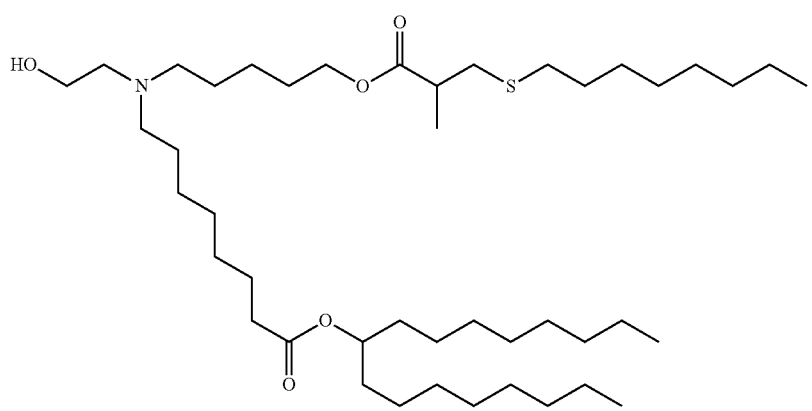 [SMILES: CCCCCCCCSCC(C)C(=O)OCCCCCN(CCO)CCCCCCCC(=O)OC(CCCCCCCC)CCCCCCCC]
35
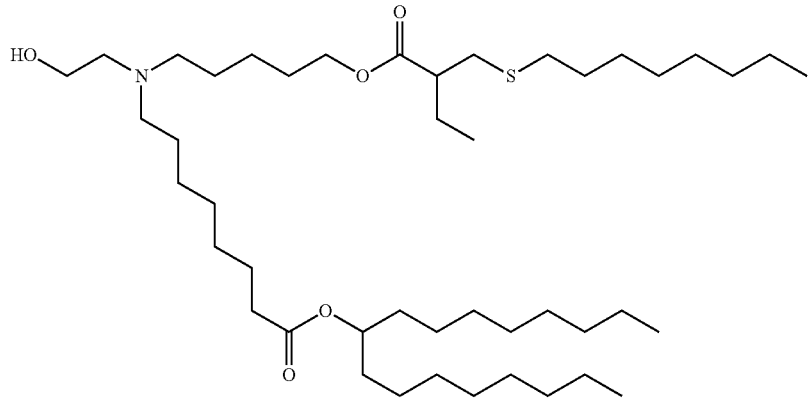
36

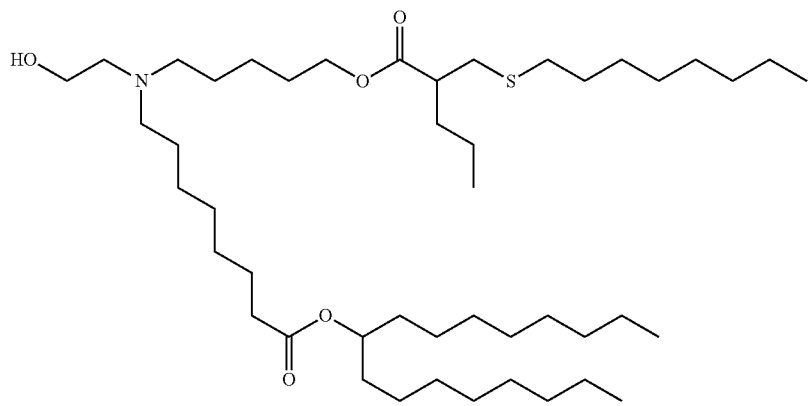
37
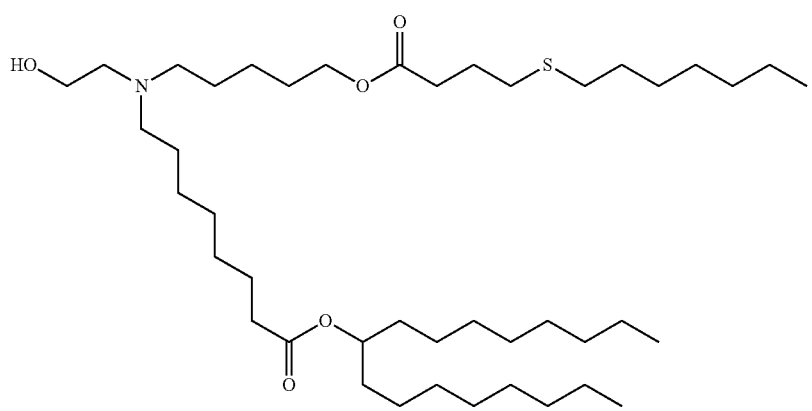
38
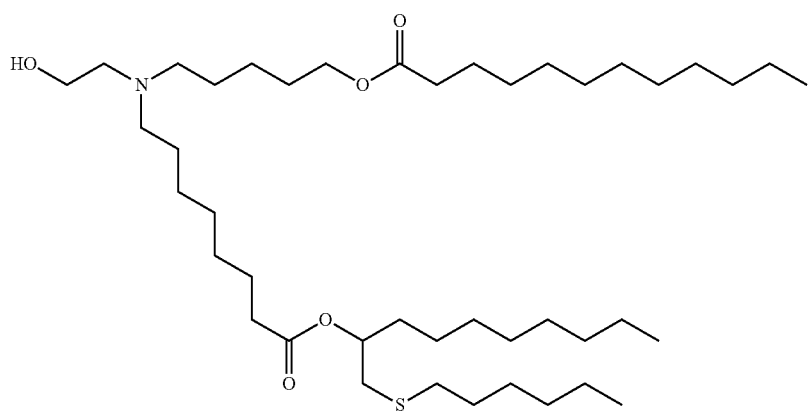
39

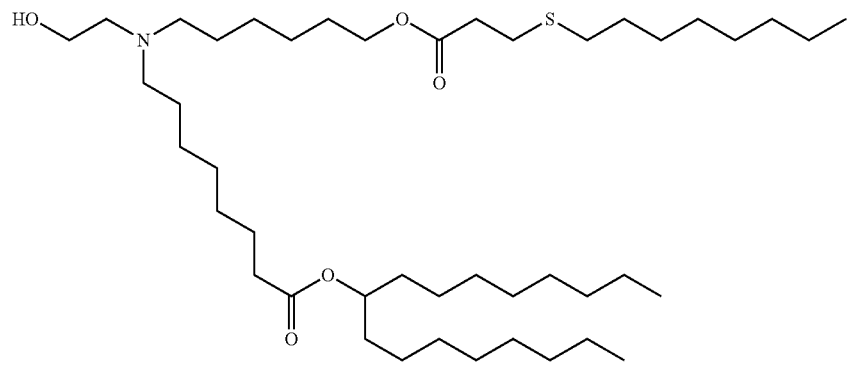 [SMILES: CCCCCCCCSCCC(=O)OCCCCCCN(CCO)CCCCCCCC(=O)OC(CCCCCCCC)CCCCCCCC]
40
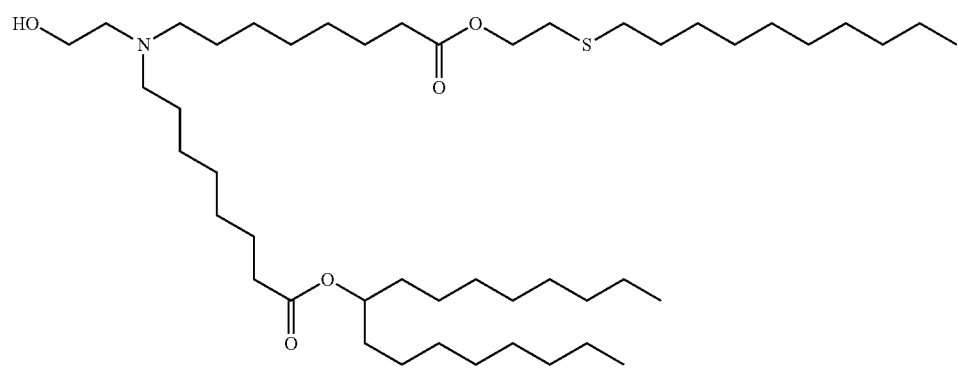 [SMILES: CCCCCCCCCCSCCOC(=O)CCCCCCCN(CCO)CCCCCCCC(=O)OC(CCCCCCCC)CCCCCCCC]
41
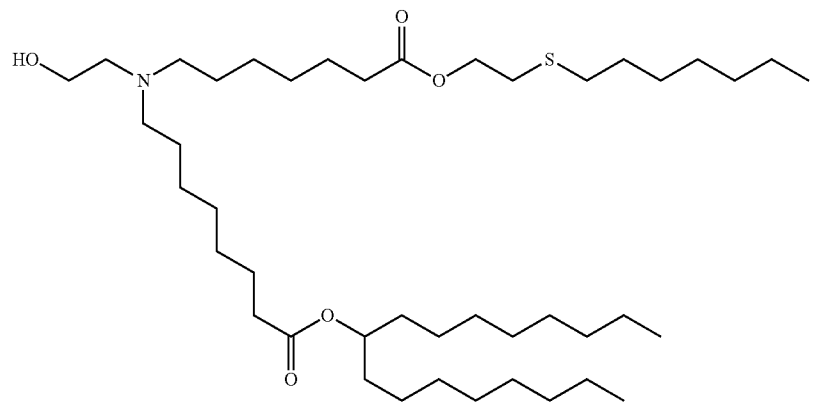 [SMILES: CCCCCCCCC(CCCCCCCC)OC(=O)CCCCCCCN(CCO)CCCCCCC(=O)OCCSCCCCCCC]
42

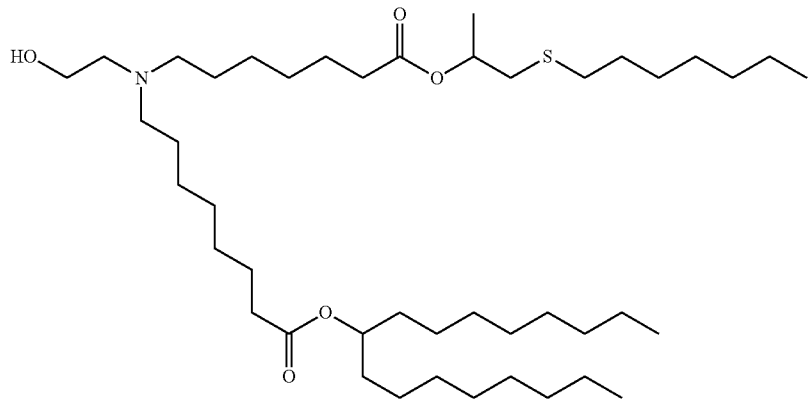 [SMILES: CCCCCCCCC(CCCCCCCC)OC(=O)CCCCCCCN(CCO)CCCCCCC(=O)OC(C)CSCCCCCCC]
43
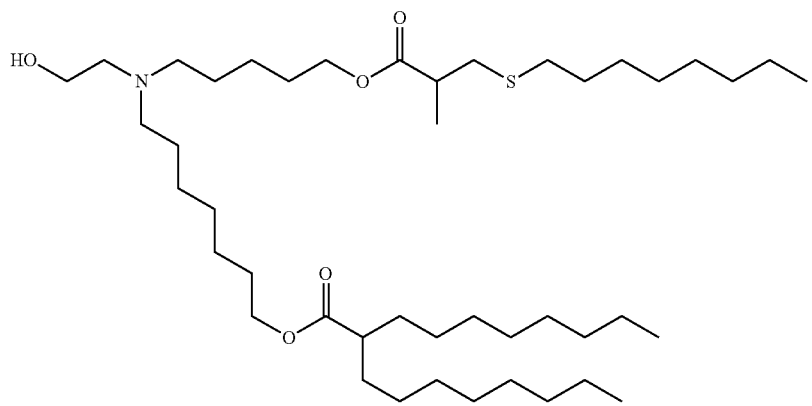
44
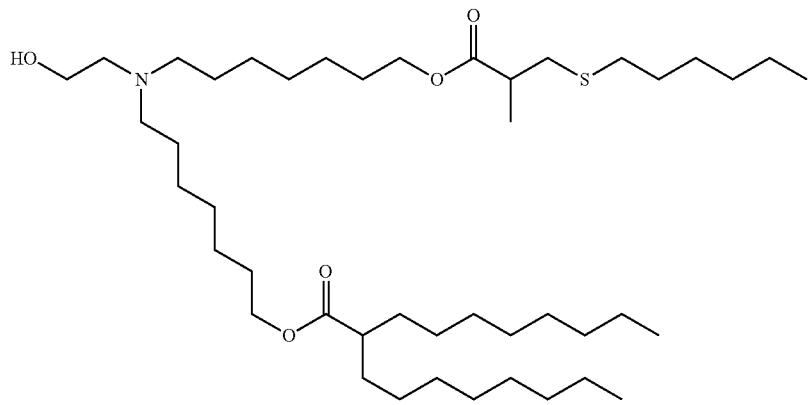 [SMILES: CCCCCCCCC(CCCCCCCC)C(=O)OCCCCCCCN(CCO)CCCCCCCOC(=O)C(C)CSCCCCCC]
45

-continued
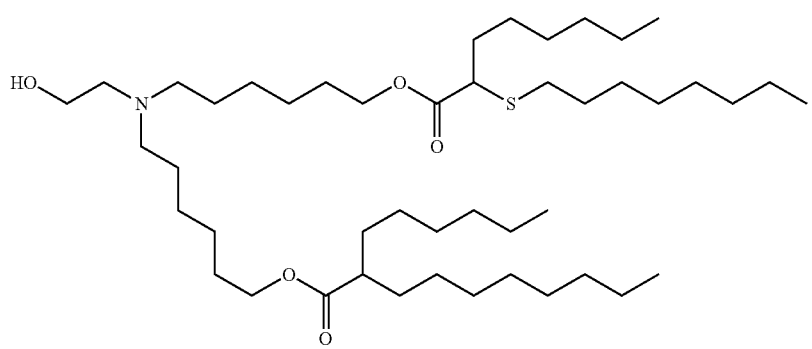 [SMILES: CCCCCCCCSC(CCCCCC)C(=O)OCCCCCCN(CCO)CCCCCCOC(=O)C(CCCCCC)CCCCCCCC]
46
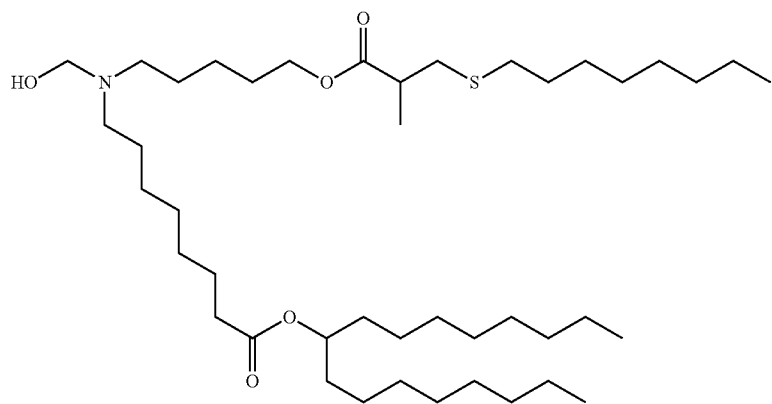 [SMILES: CCCCCCCCSCC(C)C(=O)OCCCCCN(CO)CCCCCCCC(=O)OC(CCCCCCCC)CCCCCCCC]
47
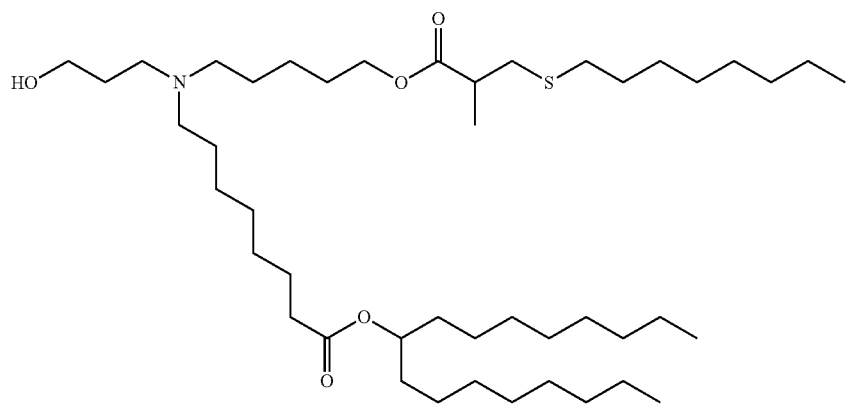 [SMILES: CCCCCCCCSCC(C)C(=O)OCCCCCN(CCCO)CCCCCCCC(=O)OC(CCCCCCCC)CCCCCCCC]
48

-continued
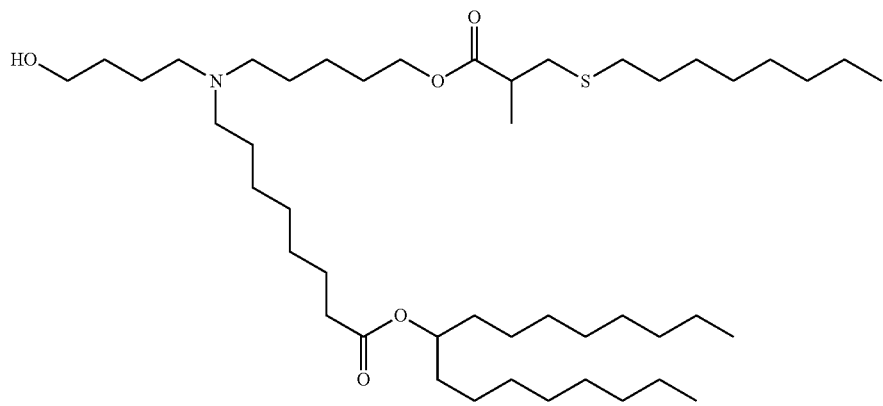
49
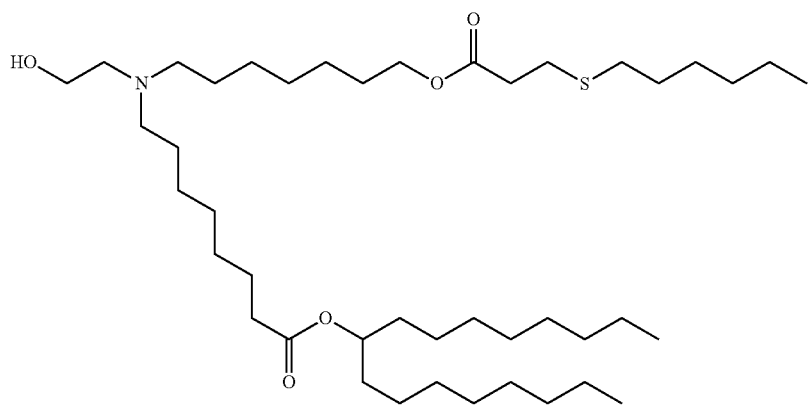
50
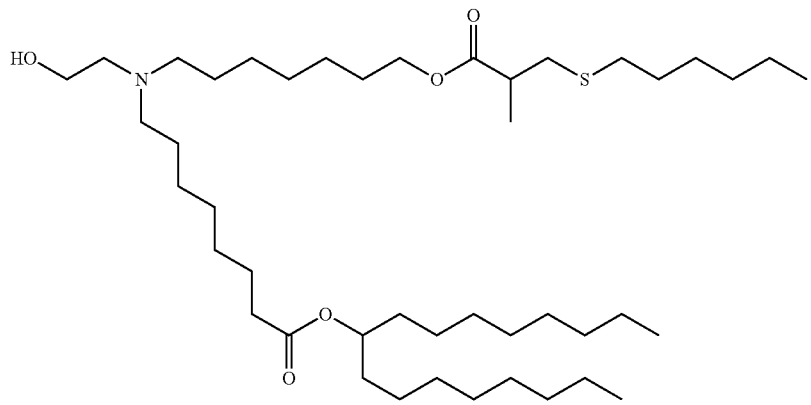 [SMILES: CCCCCCCCC(CCCCCCCC)OC(=O)CCCCCCCN(CCO)CCCCCCCOC(=O)C(C)CSCCCCCC]
51

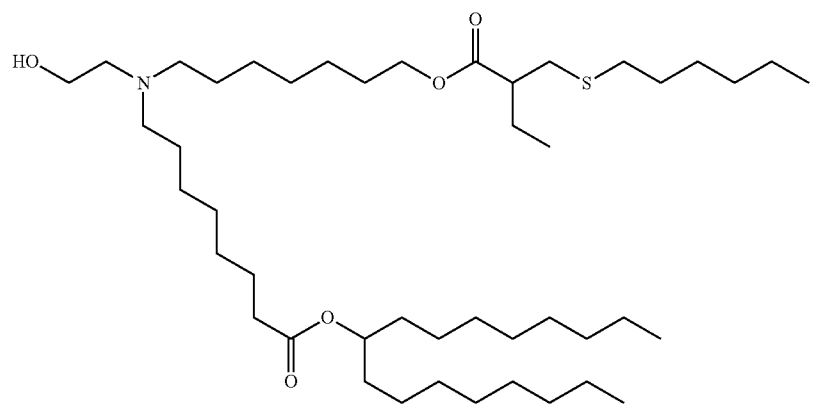 [SMILES: CCCCCCCCC(CCCCCCCC)OC(=O)CCCCCCCN(CCO)CCCCCCCOC(=O)C(CC)CSCCCCCC]
52
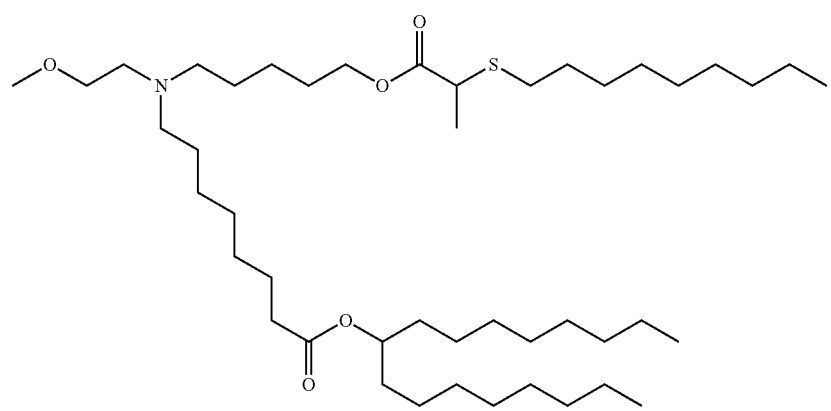 [SMILES: CCCCCCCCCSC(C)C(=O)OCCCCCN(CCCCCCCC(=O)OC(CCCCCCCC)CCCCCCCC)CCOC]
53
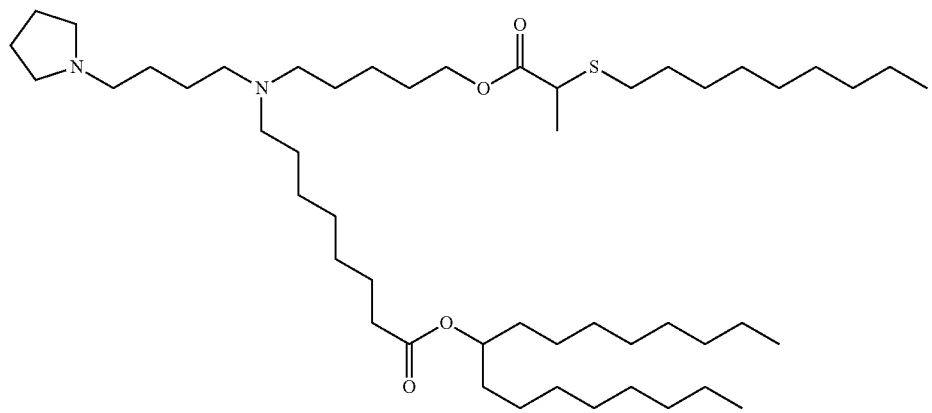 [SMILES: CCCCCCCCCSC(C)C(=O)OCCCCCN(CCCCCCCC(=O)OC(CCCCCCCC)CCCCCCCC)CCCCN1CCCC1]
54

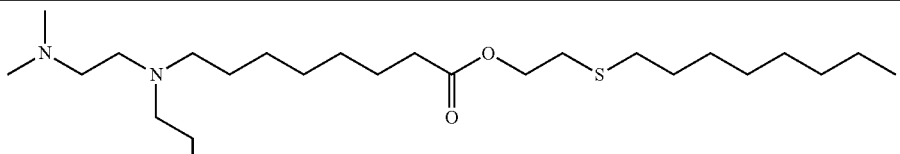

55

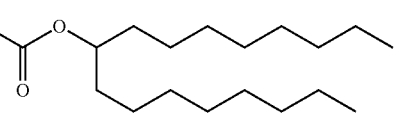

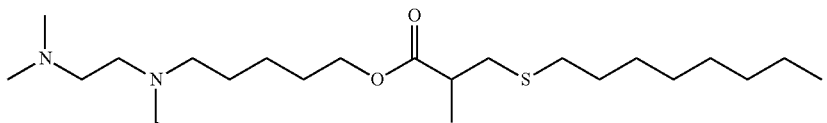

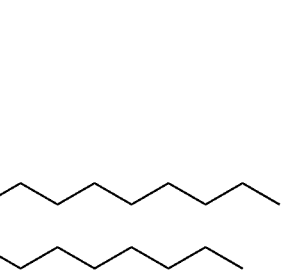

56

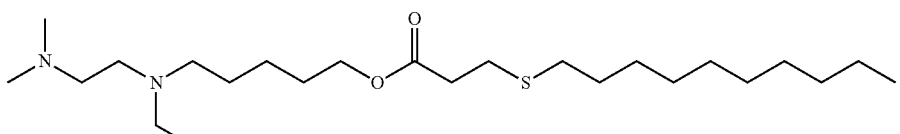

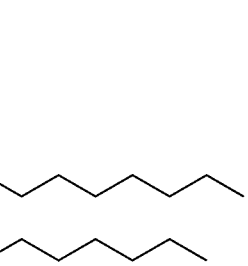

57

The present disclosure also provides a liposomal formulation comprising one or more cationic lipid compounds of the present disclosure and prophylactic or therapeutic nucleic acids, wherein the liposomal formulation is used for prevention or treatment of certain diseases.

The liposomal formulation comprises one or more components selected from neutral lipids, charged lipids, steroids and polymer-conjugated lipids. The therapeutic substances used in the present disclosure are therapeutic nucleic acids comprising plasmid DNA, messenger RNA, antisense oligonucleotide (ASON), micro RNA (miRNA), interfering RNA (micRNA), dicer substrate RNA, complementary DNA (cDNA), preferably plasmid DNA, messenger RNA and antisense oligonucleotides.

In some specific embodiments of the present disclosure, the molar ratio of the nucleic acid to the cationic lipid compound is from 20:1 to 1:1.

In some specific embodiments of the present disclosure, the molar ratio of the nucleic acid to the cationic lipid compound is from 10:1 to 4:1.

In some specific embodiments of the present disclosure, the liposomal formulation has a diameter of 50 nm to 300 nm.

In some specific embodiments of the present disclosure, the liposomal formulation has a diameter of 50 nm to 150 nm, or 150 nm to 200 nm.

In some specific embodiments of the present disclosure, it further comprises one or more other lipid components, including, but not limited to, a neutral lipid, a steroid and a polymer-conjugated lipid.

In some specific embodiments of the present disclosure, the included steroid is cholesterol.

In some specific embodiments of the present disclosure, the molar ratio of the cholesterol to the cationic lipid compound is from (0-1.5):1.

In some specific embodiments of the present disclosure, the polymer in the polymer-conjugated lipid is polyethylene glycol (PEG).

In some specific embodiments of the present disclosure, the molar ratio of the cationic lipid compound to the polyethylene glycol-conjugated lipid is from 100:1 to 20:1.

In some specific embodiments of the present disclosure, the polyethylene glycol-conjugated lipid is PEG-DAG, PEG-PE, PEG-SDAG, PEG-cer, PEG-DMG or ALC-0159.

In some specific embodiments of the present disclosure, the liposomal formulation comprises one or more neutral lipids selected from DSPC, DPPC, DMPC, DOPC, POPC, DOPE and SM.

In some specific embodiments of the present disclosure, the neutral lipid is DSPC or DOPE.

In some specific embodiments of the present disclosure, the molar ratio of the neutral lipid to the cationic lipid compound is from (0-0.5): 1.

In some specific embodiments of the present disclosure, the liposomal formulation comprises a nucleic acid.

In some specific embodiments of the present disclosure, the nucleic acid is selected from antisense RNA and/or messenger RNA.

In some specific embodiments of the present disclosure, the nucleic acid is messenger RNA.

The present disclosure also provides the use of the cationic lipid compound or the liposomal formulation described herein in the preparation of a medicament for inducing protein expression in a subject.

In some specific embodiments of the present disclosure, the subject is a mammal.

In some specific embodiments of the present disclosure, the subject is a non-human primate.

In some specific embodiments of the present disclosure, the subject is a human.

Unless stated to the contrary, terms used in the specification and claims of the present application have the following meanings.

"Alkyl" includes substituted or unsubstituted linear or branched saturated aliphatic hydrocarbon groups, including, but not limited to, alkyl groups of 1 to 20 carbon atoms, alkyl groups of 1 to 8 carbon atoms, alkyl groups of 1 to 6 carbon atoms, and alkyl groups of 1 to 4 carbon atoms. Non-limiting examples include methyl, ethyl, n-propyl, isopropyl, n-butyl, sec-butyl, neo-butyl, tert-butyl, n-pentyl, iso-pentyl, neo-pentyl, n-hexyl, and various branched isomers thereof. Alkyl, as it appears herein, is defined consistent with the definition here.

"Alkylene" includes substituted or unsubstituted linear and branched divalent saturated hydrocarbon groups, including —$(CH_2)_v$— (v is an integer from 1 to 10). Examples of alkylene groups include, but are not limited to, methylene, ethylene, propylene, butylene, and the like.

"Aliphatic hydrocarbon groups" includes saturated or unsaturated, linear or branched, chain or cyclic hydrocarbon groups, and aliphatic hydrocarbon groups with/without heteroatoms. The heteroatoms refer to nitrogen atoms, oxygen atoms, fluorine atoms, phosphorus atoms, sulfur atoms and selenium atoms. The type of aliphatic hydrocarbon groups may be selected from alkyl, alkenyl, alkynyl and the like. As used herein, for example, the term "$C_1$-10 aliphatic hydrocarbon groups" includes methyl, ethyl, n-propyl, isopropyl, n-butyl, isobutyl, tert-butyl, n-pentyl, iso-pentyl, neo-pentyl, n-hexyl, n-heptyl, vinyl, 1-propenyl, 2-propenyl, 1-methyl-vinyl, 1-butenyl, 1-ethylvinyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 1-methyl-2-propynyl, 3-butynyl, 1-pentynyl, 1-hexynyl, cyclopropyl, cyclobutyl, cyclopentyl, cyclohexyl and the like.

"Heterocycloalkyl" includes substituted or unsubstituted saturated cycloalkyl groups containing heteroatoms including, but not limited to, 3 to 10 atoms, or 3 to 8 atoms, and 1 to 3 heteroatoms selected from N, O or S. The selectively substituted N and S in the ring of the heterocycloalkyl group may be oxidized to various oxidation states. The linking site in the heterocycloalkyl group may be at a heteroatom or a carbon atom, the heterocycloalkyl group may be attached to an aromatic ring or a non-aromatic ring, and the heterocycloalkyl group may be attached to a bridging ring or a spiro ring. Non-limiting examples include epoxyethyl, aziridinyl, oxetidinyl, azetidinyl, tetrahydrofuranyl, tetrahydro-2H-pyranyl, dioxolanyl, dioxanyl, pyrrolidinyl, piperidinyl, imidazolidinyl, oxazolidinyl, oxazinanyl, morpholino, hexahydro-pyrimidinyl, piperazinyl.

In summary, the present disclosure provides a cationic lipid compound and liposomal formulation for delivery of nucleic acids and use thereof. The technical solution of the present disclosure has the following advantages: The cationic lipid compound of the present disclosure has an ester bond or thioester bond. The introduction of the ester bond or thioester bond makes the compound more easily degradable and improves the in vivo scavenging rate of the lipid compounds, resulting in lower toxicity and fewer in vivo residues in the carriers comprising the compounds. After structural optimization, the in vivo transfection efficiency of the selected cationic compounds was superior to that of some commercial transfection cationic lipid compounds. Moreover, the method of preparing the amino-lipid compounds described herein has the advantages of easy availability of raw materials, mild reaction conditions, high product yield, low requirements for instrumentation and simple operation.

DETAILED DESCRIPTION OF PREFERRED EMBODIMENTS

Figure 1:
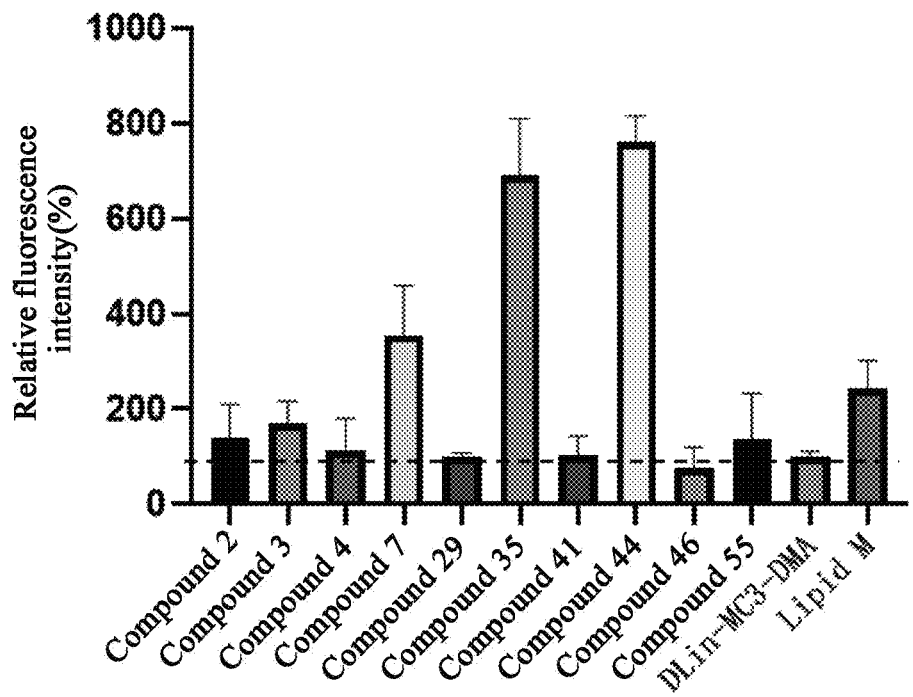
FIG. 1 shows the in vivo imaging relative fluorescence intensity of mice with intramuscular injection of Example 21.

The technical solutions of the present disclosure are described in detail below in conjunction with the accompanying drawings and examples, but the protection scope of the present disclosure includes, but is not limited to, them.

Example 1
Synthesis of Compound 2
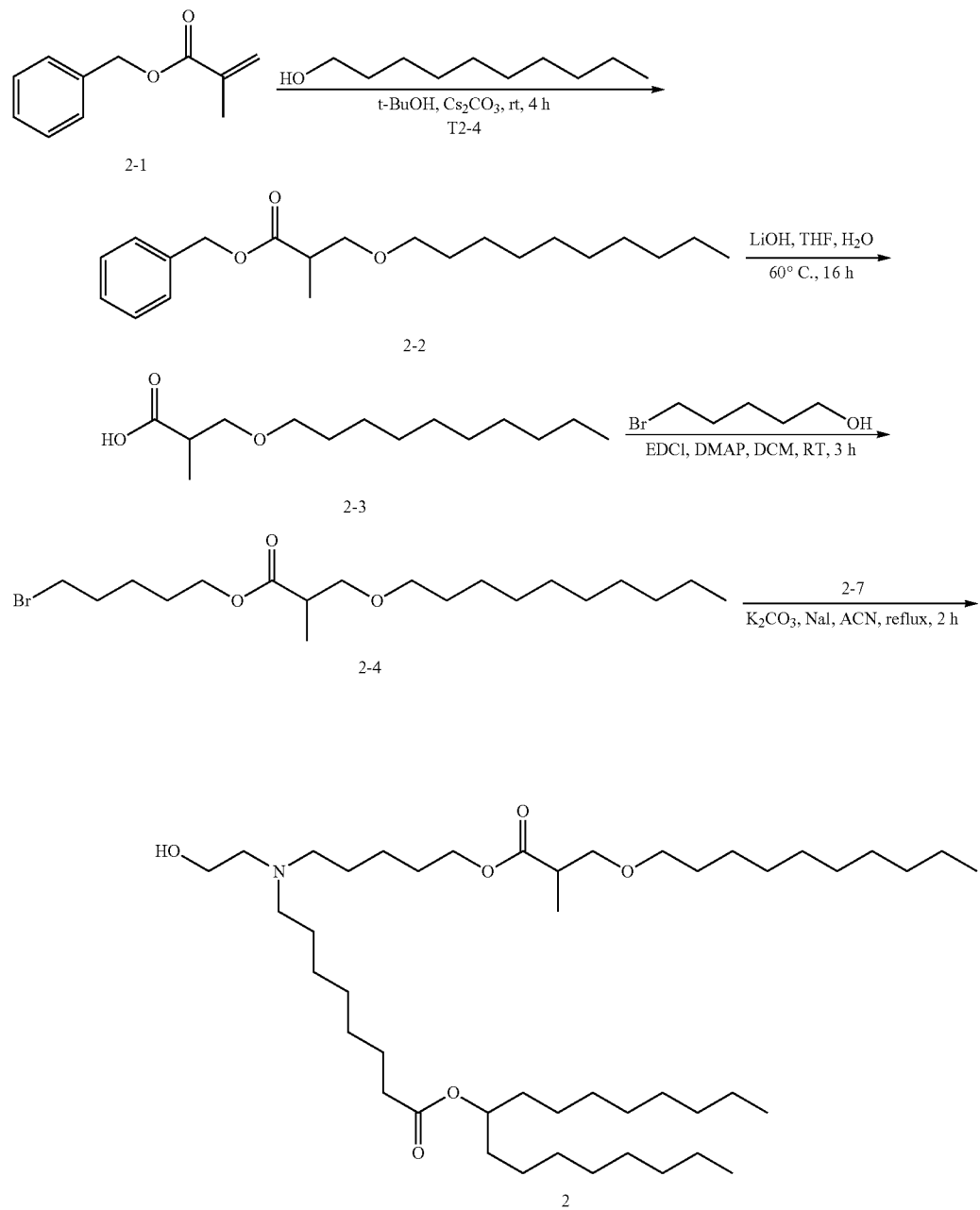
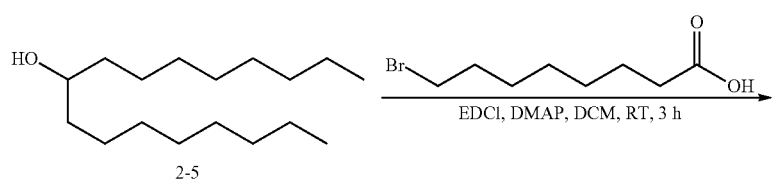

-continued

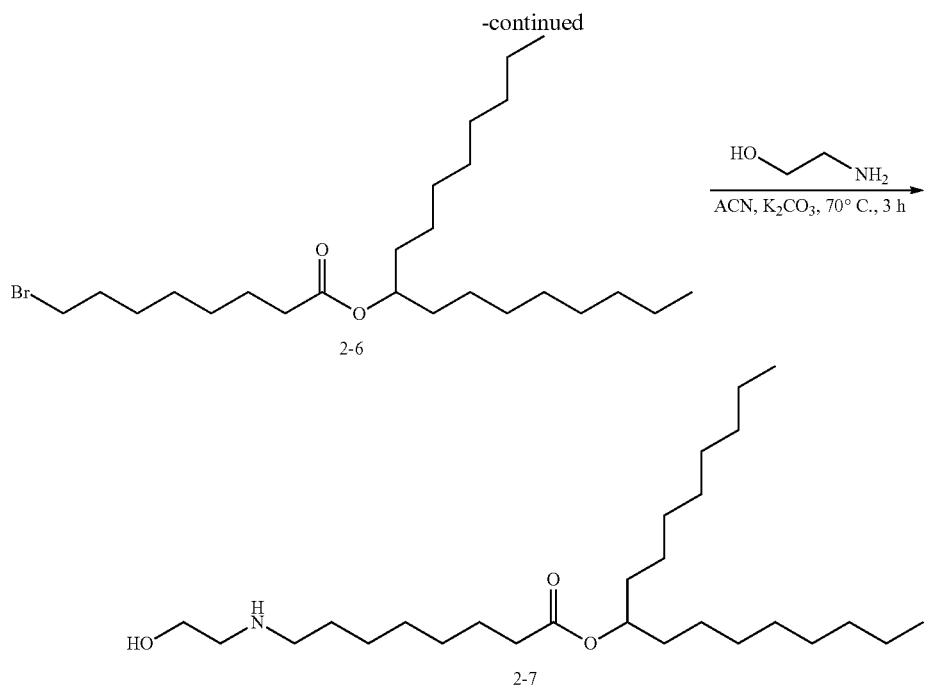

Step 1:
To a solution of compound 2-1 (3.00 g) in tert-butanol (20 mL), 1-decanol (3.23 g) and cesium carbonate (11.1 g) were added sequentially. After the solution was stirred at room temperature for 4 h, the spot plate (petroleum ether:ethyl acetate=10:1) showed the generation of new spots. The reaction solution was filtered. The resulting filtrate was concentrated to obtain a crude product, which was then purified by column chromatography (with a silica gel column and a petroleum ether solution containing 0-10% ethyl acetate (v/v) as the eluent), to give a compound 2-2 (3.93 g, 69% yield).

Step 2:
To a solution of compound 2-2 (3.00 g) in THF (20 mL) and water, lithium hydroxide (860 mg) was added. The mixture was stirred at 60° C. for 16 h. TLC showed generation of a spot with increased polarity. The reaction mixture was concentrated to remove tetrahydrofuran, diluted with water, and extracted once with ethyl acetate (30 mL). The aqueous phase was adjusted to pH=2 with dilute hydrochloric acid and extracted twice with ethyl acetate (30 mL). The organic layers were combined and concentrated to give a compound 2-3 (2.10 g, 95% yield).

Step 3:
Compound 2-3 (2.0 g) was dissolved in DCM (20 ml) and stirred at room temperature. 1-ethyl-(3-dimethylaminopropyl)carbodiimide hydrochloride (EDCI, 2.0 g), 4-dimethylaminopyridine (DMAP, 1.3 g) and 5-bromo-1-pentanol (1.5 g) were weighed sequentially, and added to the reaction system in batches and stirred at room temperature for 3 h. A small amount of the reaction solution was diluted and spotted on the plate in control with a 2-3 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min), to give a colorless oily liquid compound 2-4 (2.8 g, 87% yield).

Step 4:
Compound 2-5 (5.0 g) was dissolved in dichloromethane (70 ml) and stirred at room temperature. 1-ethyl-(3-dimethylaminopropyl)carbodiimide hydrochloride (EDCI, 4.48 g), 4-dimethylaminopyridine (DMAP, 3.57 g) and 8-bromooctanoic acid (4.78 g) were weighed sequentially, and added to the reaction system in batches and stirred at room temperature for 3 h. A small amount of the reaction solution was diluted and spotted on the plate in control with a 2-5 standard sample (PE/EA=10/1, phosphomolybdic acid). New spots with reduced polarity were observed. The reaction solution was evaporated under reduced pressure. It was mixed with appropriate amount of silica gel and DCM, and purified (60 g normal phase column, PE/EA, 0-0% 5 min, 0-5% 20 min, 5-5% 5 min, a flow rate of 30 ml/min), to give a colorless oily liquid compound 2-6 (8.0 g, 88.9% yield). Compound 2-6 of Examples 1-6, 8-10, 11-13 and 16-18 below were synthesized using this method.

Step 5:
To a solution of compound 2-6 (8.0 g) and ethanolamine (1.59 g) in acetonitrile (50 mL), potassium carbonate (7.19 g) was added. The mixture was stirred at 70° C. for 2 h. TLC showed complete disappearance of compound 2-6 and generation of a spot with increased polarity. The reaction solution was filtered. The resulting filtrate was concentrated to obtain a crude product, which was then was mixed with appropriate amount of silica gel and DCM, and purified (25 g normal phase column, PE/EA, 0-0% 5 min, 0-10% 20 min, 10-10% 5 min, a flow rate of 20 ml/min), to give a colorless oily liquid compound 2-7 (4.2 g, 54.9% yield).

Step 6:
Compound 2-4 (500 mg) was dissolved in acetonitrile (10 ml) and stirred at room temperature. Subsequently, NaI (191 mg), $K_2CO_3$ (527 mg) and compound 2-7 (673 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 2 (700 mg, 73% yield).

$^1$H NMR (400 MHz, Chloroform-d) δ 4.80 (s, 1H), 4.16-4.01 (d, J=3.2 Hz, 2H), 3.75-3.45 (m, 6H), 2.78-2.68 (dd, J=8.2, 5.8 Hz, 2H), 2.61-2.51 (m, 2H), 2.50-2.45 (m, 4H), 2.31-2.16 (m, 2H), 1.70-1.69 (s, 1H), 1.68-1.66 (s, 1H), 1.58-1.57 (s, 2H), 1.57-1.55 (d, J=3.4 Hz, 2H), 1.55-1.51 (m, 6H), 1.50-1.48 (s, 2H), 1.38-1.35 (d, J=1.0 Hz, 4H), 1.35-1.30 (m, 20H), 1.30-1.27 (m, 20H), 1.19-1.17 (m, 3H), 0.91-0.88 (m, 9H).

Example 2

Synthesis of Compound 3

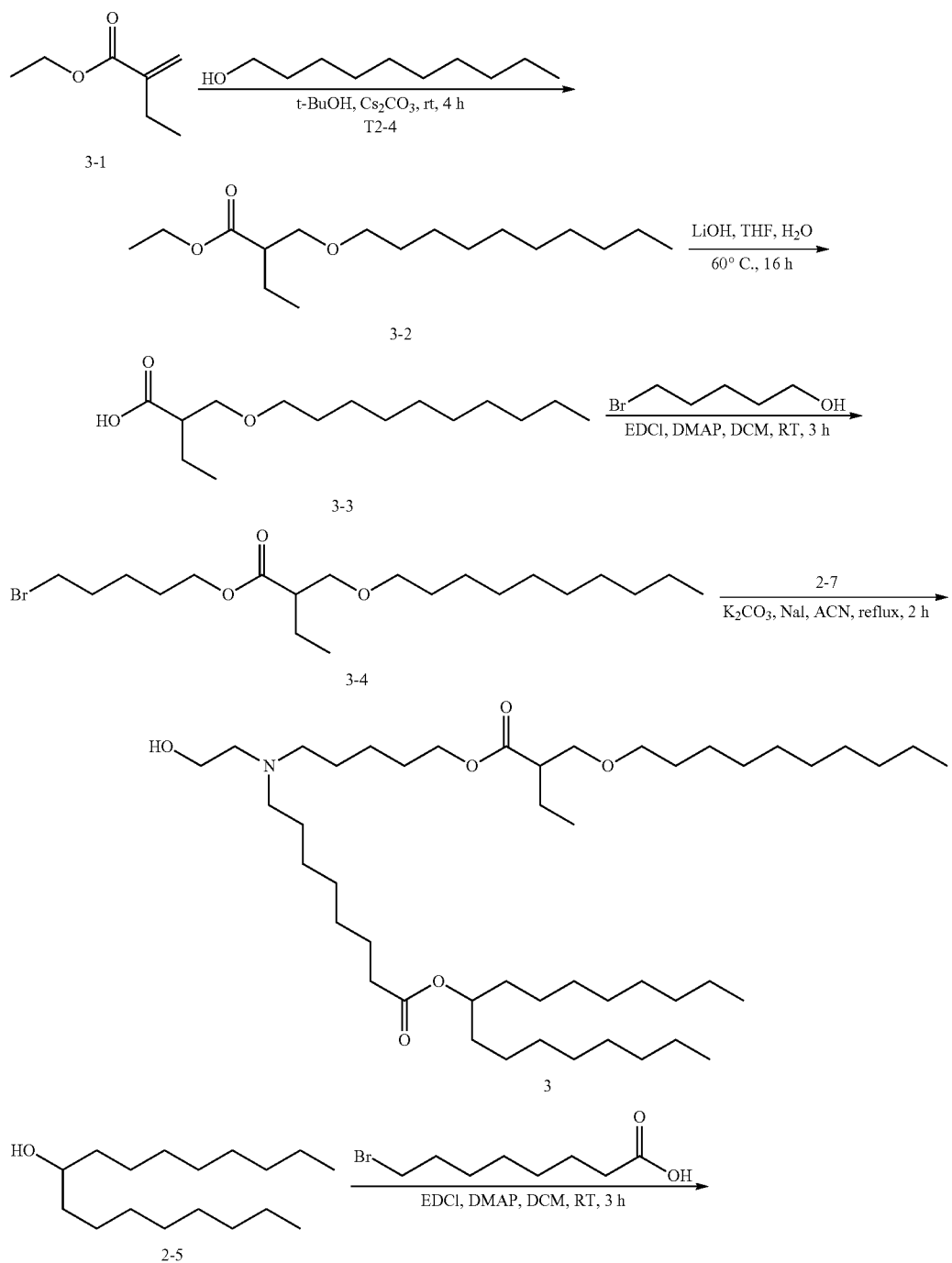

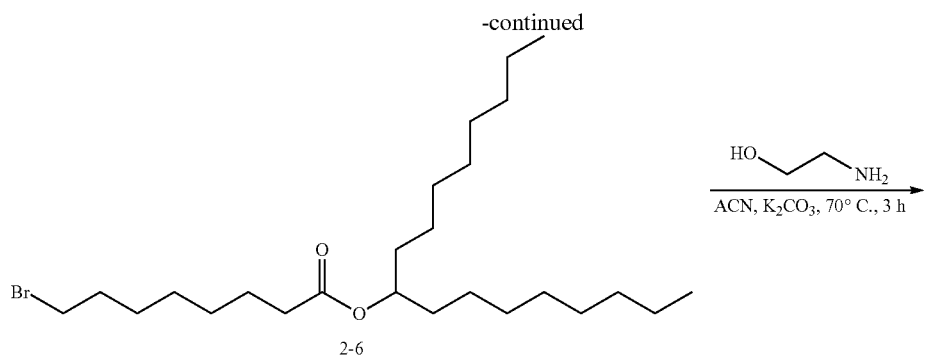

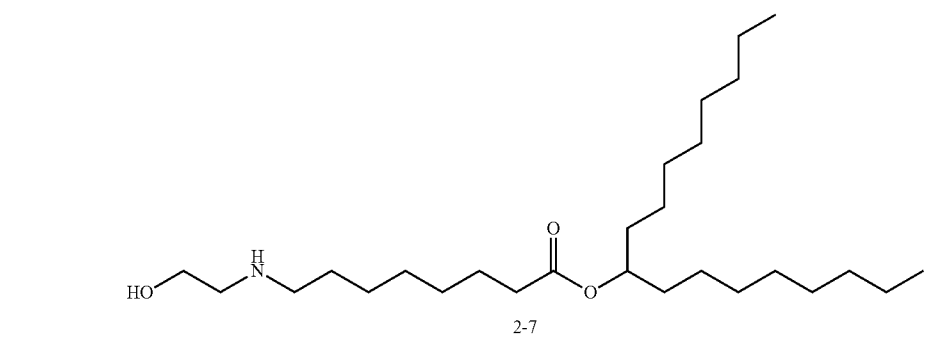

Step 1:

To a solution of compound 3-1 (3.00 g) in tert-butanol (20 mL), 1-decanol (4.45 g) and cesium carbonate (15.3 g) were added sequentially. After the solution was stirred at room temperature for 4 h, the spot plate (petroleum ether:ethyl acetate=10:1) showed the generation of new spots. The reaction solution was filtered. The resulting filtrate was concentrated to obtain a crude product, which was then purified by column chromatography (with a silica gel column and a petroleum ether solution containing 0-10% ethyl acetate (v/v) as the eluent), to give a compound 3-2 (3.1 g, 46% yield).

Step 2:

To a solution of compound 3-2 (3.00 g) in THF (20 mL) and water, lithium hydroxide (860 mg) was added. The mixture was stirred at 60° C. for 16 h. TLC (petroleum ether:ethyl acetate=10:1) showed generation of a spot with increased polarity. The reaction mixture was concentrated to remove tetrahydrofuran, diluted with water, and extracted once with ethyl acetate (30 mL). The aqueous phase was adjusted to pH=2 with dilute hydrochloric acid and extracted twice with ethyl acetate (30 mL). The organic layers were combined and concentrated to give a compound 3-3 (2.50 g, 92% yield).

Step 3:

Compound 3-3 (2.0 g) was dissolved in dichloromethane (20 ml) and stirred at room temperature. 1-ethyl-(3-dimethylaminopropyl)carbodiimide hydrochloride (EDCI, 2.0 g), 4-dimethylaminopyridine (DMAP, 1.3 g) and 5-bromo-1-pentanol (1.5 g) were weighed sequentially, and added to the reaction system in batches and stirred at room temperature for 3 h. A small amount of the reaction solution was diluted and spotted on the plate in control with a 3-3 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min), to give a colorless oily liquid compound 3-4 (2.6 g, 83% yield).

Step 4:

Compound 3-4 (500 mg) was dissolved in acetonitrile (10 ml) and stirred at room temperature. Subsequently, NaI (191 mg), $K_2CO_3$ (527 mg) and compound 2-7 (673 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots with less polarity than that of 2-7 were observed. The reaction solution was cooled to room temperature and then evaporated under reduced pressure. The sample was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 3 (750 mg, 80% yield).

$^1$H NMR (400 MHz, Chloroform-d) δ 4.78 (s, 1H), 4.14-4.02 (d, J=2.6 Hz, 2H), 3.73-3.46 (m, 6H), 2.61 (s, 1H), 2.59-2.50 (m, 2H), 2.49-2.45 (m, 4H), 2.29-2.18 (m, 2H), 1.71-1.63 (m, 4H), 1.60-1.50 (m, 12H), 1.49 (s, 2H), 1.38-1.36 (d, J=0.6 Hz, 4H), 1.35-1.30 (m, 20H), 1.30-1.26 (m, 20H), 0.92 (s, 3H), 0.91-0.87 (s, 9H).

Example 3
Synthesis of Compound 4
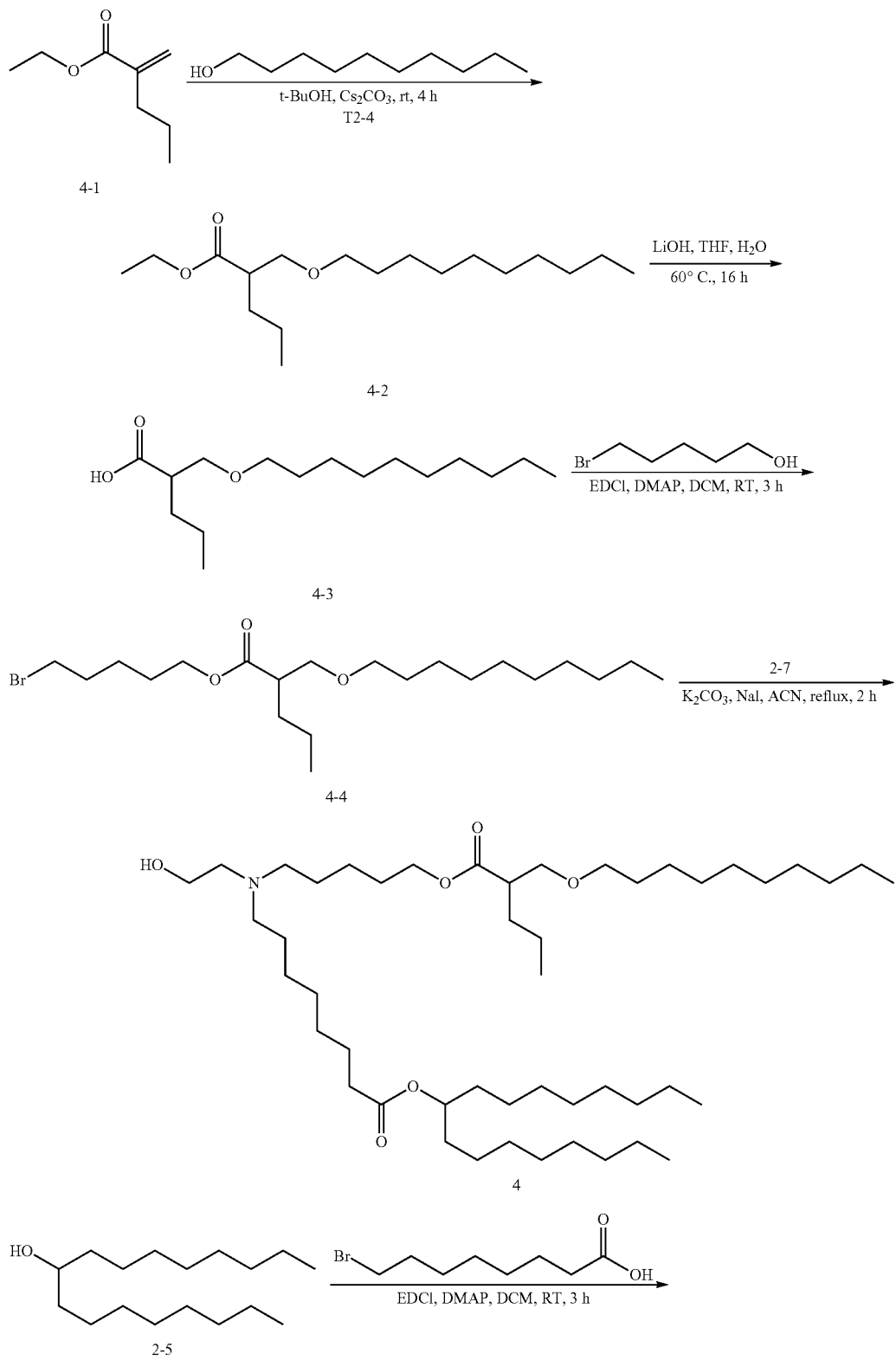

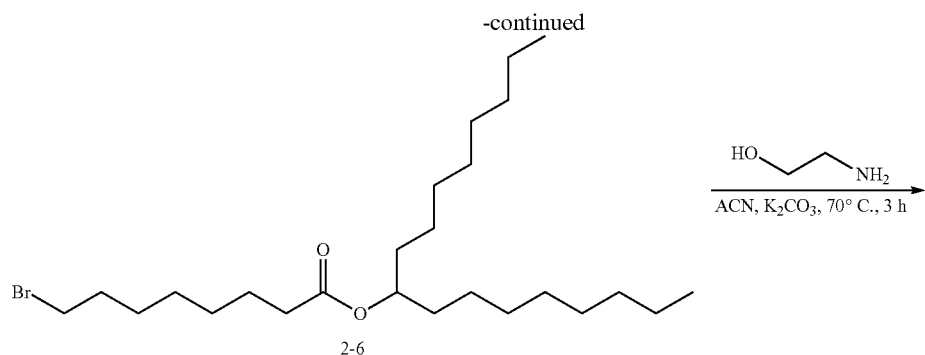

To a solution of compound 4-1 (3.00 g) in tert-butanol (20 mL), 1-decanol (4.6 g) and cesium carbonate (16.1 g) were added sequentially. After the solution was stirred at room temperature for 4 h, the spot plate (petroleum ether:ethyl acetate=10:1) showed the generation of new spots. The reaction solution was filtered. The resulting filtrate was concentrated to obtain a crude product, which was then purified by column chromatography (with a silica gel column and a petroleum ether solution containing 0-10% ethyl acetate (v/v) as the eluent), to give a compound 4-2 (3.0 g, 47.3% yield).

Step 2:

To a solution of compound 4-2 (3.00 g) in THF (20 mL) and water, lithium hydroxide (860 mg) was added. The mixture was stirred at 60° C. for 16 h. TLC (petroleum ether:ethyl acetate=10:1) showed generation of a spot with increased polarity. The reaction mixture was concentrated to remove tetrahydrofuran, diluted with water, and extracted once with ethyl acetate (30 mL). The aqueous phase was adjusted to pH=2 with dilute hydrochloric acid and extracted twice with ethyl acetate (30 mL). The organic layers were combined and concentrated to give a compound 4-3 (2.50 g, 92% yield).

Step 3:

Compound 4-3 (2.0 g) was dissolved in dichloromethane (20 ml) and stirred at room temperature. 1-ethyl-(3-dimethylaminopropyl)carbodiimide hydrochloride (EDCI, 2.1 g), 4-dimethylaminopyridine (DMAP, 1.4 g) and 5-bromo-1-pentanol (1.6 g) were weighed sequentially, and added to the reaction system in batches and stirred at room temperature for 3 h. A small amount of the reaction solution was diluted and spotted on the plate in control with a 3-3 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min), to give a colorless oily liquid compound 4-4 (2.6 g, 84% yield).

Step 4:

Compound 4-4 (500 mg) was dissolved in acetonitrile (10 ml) and stirred at room temperature. Subsequently, NaI (191 mg), $K_2CO_3$ (527 mg) and compound 2-7 (673 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% (volume percent of methanol in DCM/MeOH solution, same as below) 10 min, 0-7.5% 20 min, 7.5-7.5% 5 min, a flow rate of 25 ml/min), and concentrated to give a light yellow oily liquid compound 4 (610 mg, 65.7% yield).

$^1$H NMR (400 MHz, Chloroform-d) δ 4.80-4.74 (s, 1H), 4.15-4.01 (d, J=2.6 Hz, 2H), 3.73-3.44 (m, 6H), 2.56-2.50 (m, 3H), 2.49-2.45 (m, 4H), 2.29-2.18 (m, 2H), 1.71-1.47 (m, 18H), 1.41-1.26 (m, 46H), 0.96-0.92 (m, 3H), 0.99 (s, 9H).

Example 4
Synthesis of Compound 6
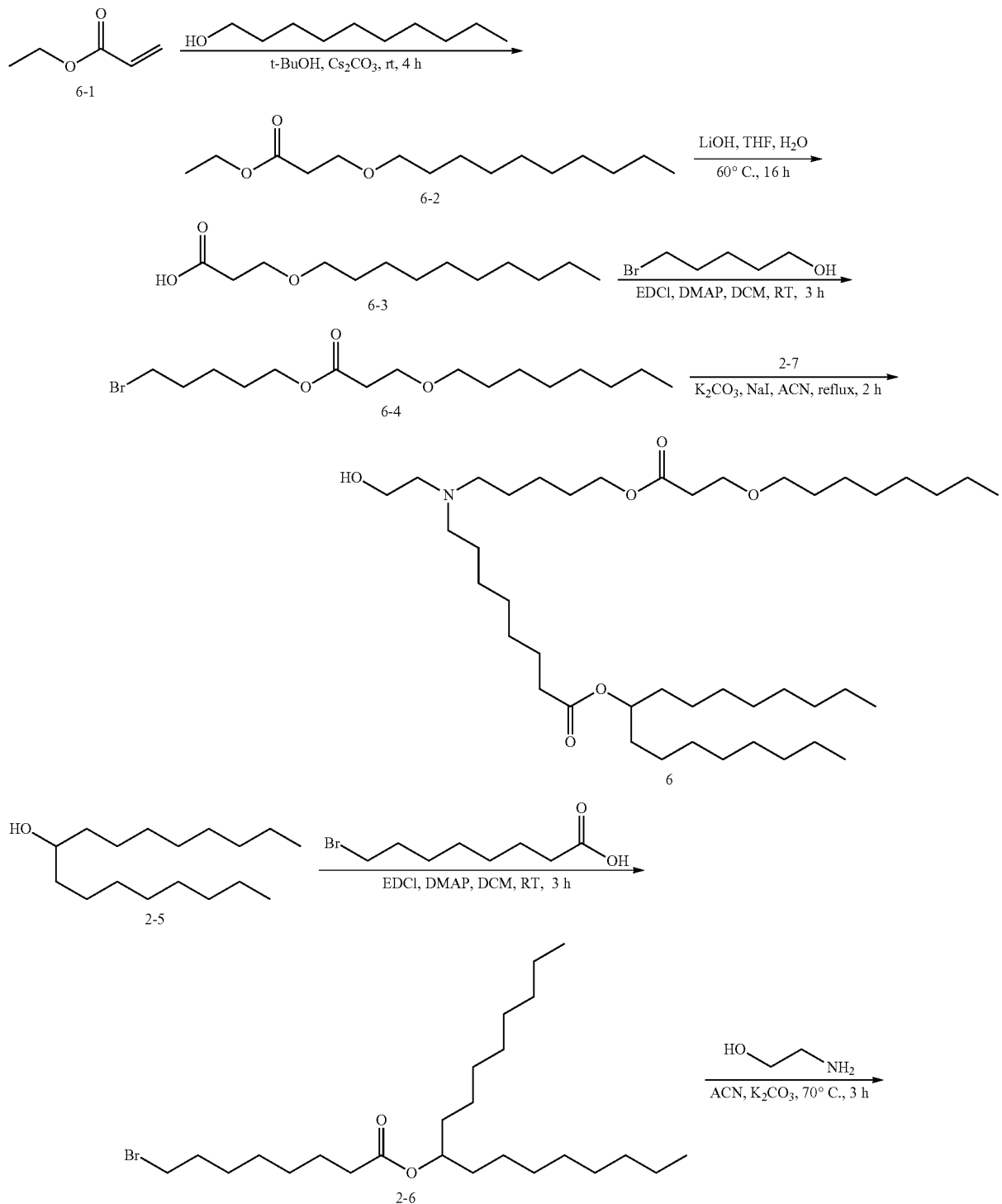

-continued

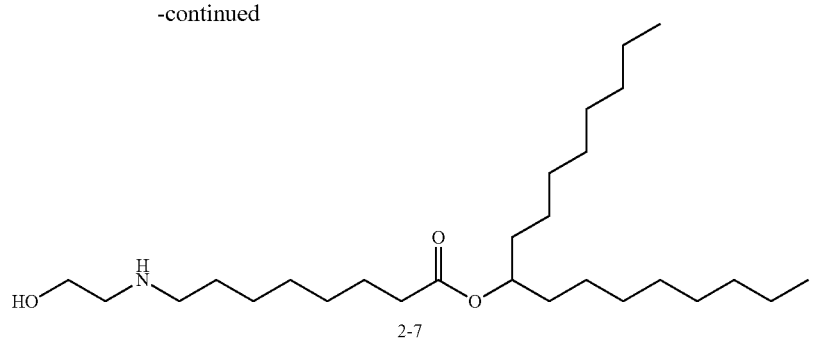

2-7

Step 1:

To a solution of compound 6-1 (19.0 g) in tert-butanol (20 mL), 1-decanol (3.0 g) and cesium carbonate (12.4 g) were added sequentially. After the solution was stirred at room temperature for 4 h, the spot plate (petroleum ether:ethyl acetate=10:1) showed the generation of new spots. The reaction solution was filtered. The resulting filtrate was concentrated to obtain a crude product, which was then purified by column chromatography (with a silica gel column and a petroleum ether solution containing 0-10% ethyl acetate (v/v) as the eluent), to give a compound 6-2 (2.1 g, 43% yield).

Step 2:

To a solution of compound 6-2 (2.1 g) in THE (20 mL) and water (10 mL), lithium hydroxide (584 mg) was added. The mixture was stirred at 60° C. for 16 h. TLC (petroleum ether:ethyl acetate=10:1) showed generation of a spot with increased polarity. The reaction mixture was concentrated to remove tetrahydrofuran, diluted with water, and extracted once with ethyl acetate (30 mL). The aqueous phase was adjusted to pH=2 with dilute hydrochloric acid and extracted twice with ethyl acetate (30 mL). The organic layers were combined and concentrated to give a compound 6-3 (1.6 g, 85% yield).

Step 3:

Compound 6-3 (2.0 g) was dissolved in dichloromethane (20 ml) and stirred at room temperature. 1-ethyl-(3-dimethylaminopropyl)carbodiimide hydrochloride (EDCI, 2.0 g), 4-dimethylaminopyridine (DMAP, 1.3 g) and 5-bromo-1-pentanol (1.5 g) were weighed sequentially, and added to the reaction system in batches and stirred at room temperature for 3 h. A small amount of the reaction solution was diluted and spotted on the plate in control with a 6-3 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min), to give a colorless oily liquid compound 6-4 (2.5 g, 82% yield).

Step 4:

Compound 6-4 (500 mg) was dissolved in acetonitrile (10 ml) and stirred at room temperature. Subsequently, NaI (191 mg), $K_2CO_3$ (527 mg) and compound 2-7 (673 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 6 (742 mg, 75% yield).

$^1$H NMR (400 MHz, Chloroform-d) δ 4.78 (s, 1H), 4.11 (s, 2H), 3.68-3.57 (d, J=5.0 Hz, 4H), 3.55-3.46 (s, 2H), 2.61-2.43 (m, 8H), 2.28-2.17 (s, 2H), 1.73-1.63 (d, J=3.9 Hz, 4H), 1.60-1.46 (m, 12H), 1.39-1.23 (m, 40H), 0.96-0.84 (s, 9H).

Example 5

Synthesis of Compound 7

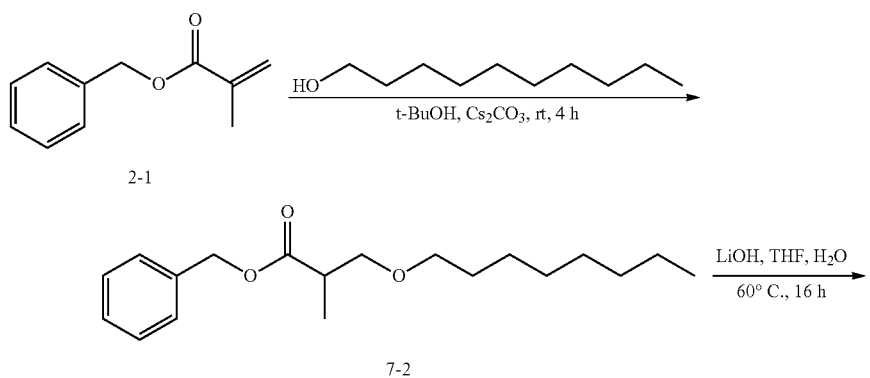

-continued
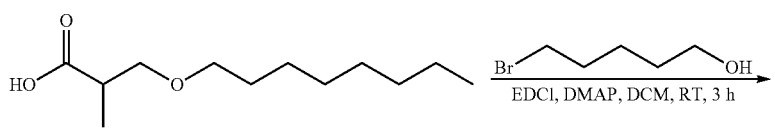
7-3
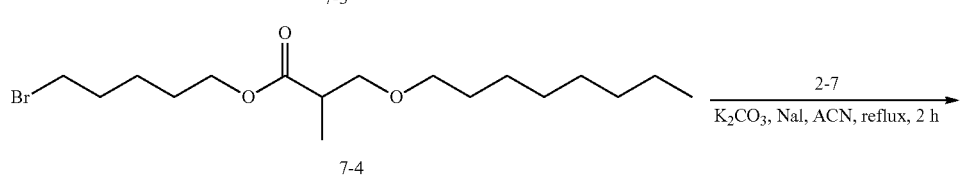
7-4
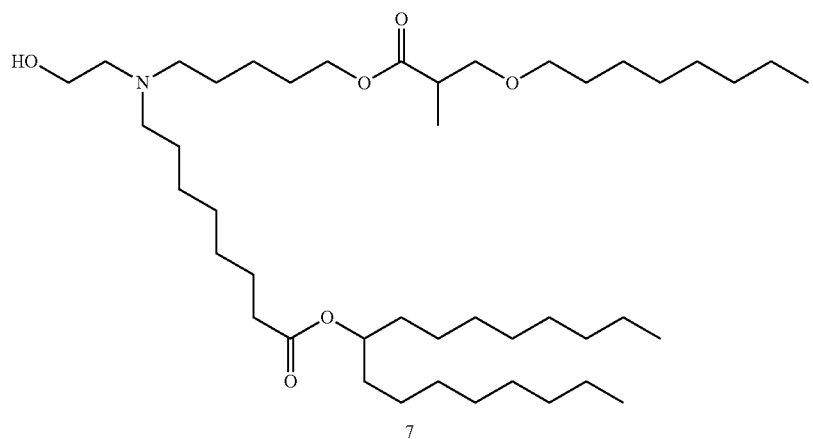
7
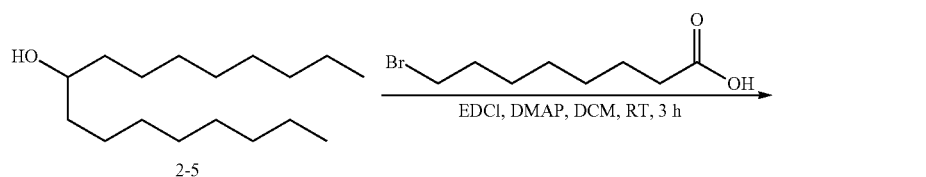
2-5
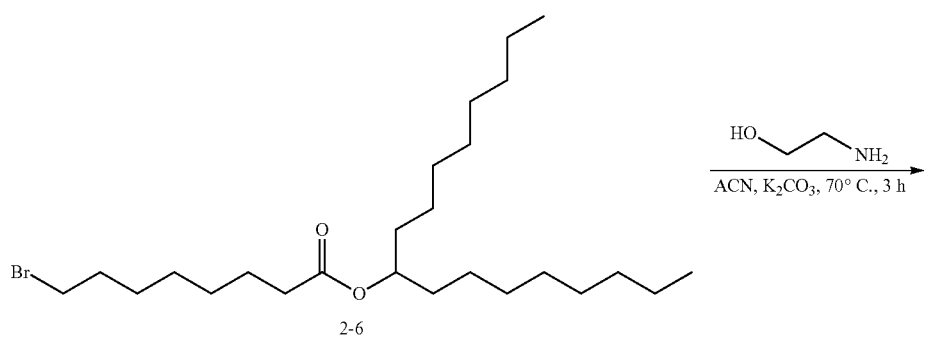
2-6
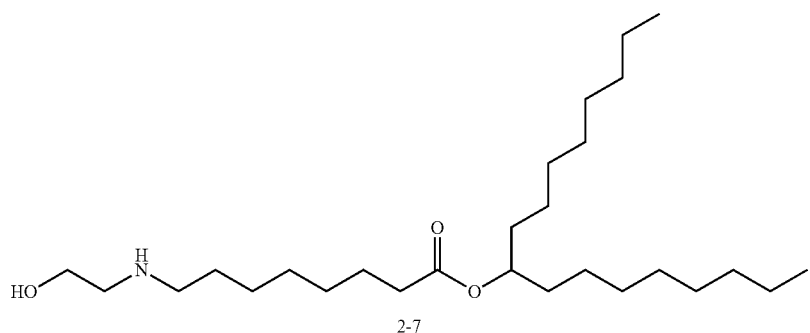
2-7

Step 1:

To a solution of compound 2-1 (3.00 g) in tert-butanol (20 mL), octanol (3.1 g) and cesium carbonate (11.0 g) were added sequentially. After the solution was stirred at room temperature for 4 h, the spot plate (petroleum ether:ethyl acetate=10:1) showed the generation of new spots. The reaction solution was filtered. The resulting filtrate was concentrated to obtain a crude product, which was then purified by column chromatography (with a silica gel column and a petroleum ether solution containing 0-10% ethyl acetate (v/v) as the eluent), to give a compound 7-2 (3.6 g, 69% yield).

Step 2:

To a solution of compound 7-2 (3.00 g) in THF (20 mL) and water, lithium hydroxide (860 mg) was added. The mixture was stirred at 60° C. for 16 h. TLC showed generation of a spot with increased polarity. The reaction mixture was concentrated to remove tetrahydrofuran, diluted with water, and extracted once with ethyl acetate (30 mL). The aqueous phase was adjusted to pH=2 with dilute hydrochloric acid and extracted twice with ethyl acetate (30 mL). The organic layers were combined and concentrated to give a compound 7-3 (2.0 g, 94% yield).

Step 3:

Compound 7-3 (2.0 g) was dissolved in dichloromethane (20 ml) and stirred at room temperature. 1-ethyl-(3-dimethylaminopropyl)carbodiimide hydrochloride (EDCI, 2.0 g), 4-dimethylaminopyridine (DMAP, 1.3 g) and 5-bromo-1-pentanol (1.5 g) were weighed sequentially, and added to the reaction system in batches and stirred at room temperature for 3 h. A small amount of the reaction solution was diluted and spotted on the plate in control with a 7-3 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min), to give a colorless oily liquid compound 7-4 (2.5 g, 74% yield).

Step 4:

Compound 7-4 (500 mg) was dissolved in acetonitrile (10 ml) and stirred at room temperature. Subsequently, NaI (191 mg), $K_2CO_3$ (527 mg) and compound 2-7 (673 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 7 (750 mg, 75% yield).

$^1$H NMR (400 MHz, Chloroform-d) δ 4.78 (s, 1H), 4.09 (d, J=2.2 Hz, 2H), 3.78-3.37 (m, 6H), 2.75 (s, 1H), 2.55 (d, J=3.8 Hz, 2H), 2.49-2.43 (m, 4H), 2.30-2.16 (m, 2H), 1.71-1.65 (m, 2H), 1.64 (s, 2H), 1.60-1.50 (m, 10H), 1.49 (s, 2H), 1.37 (d, J=0.6 Hz, 4H), 1.35-1.30 (m, 20H), 1.30-1.26 (m, 16H), 1.22-1.14 (m, 3H), 0.99 (s, 9H).

Example 6

Synthesis of Compound 6

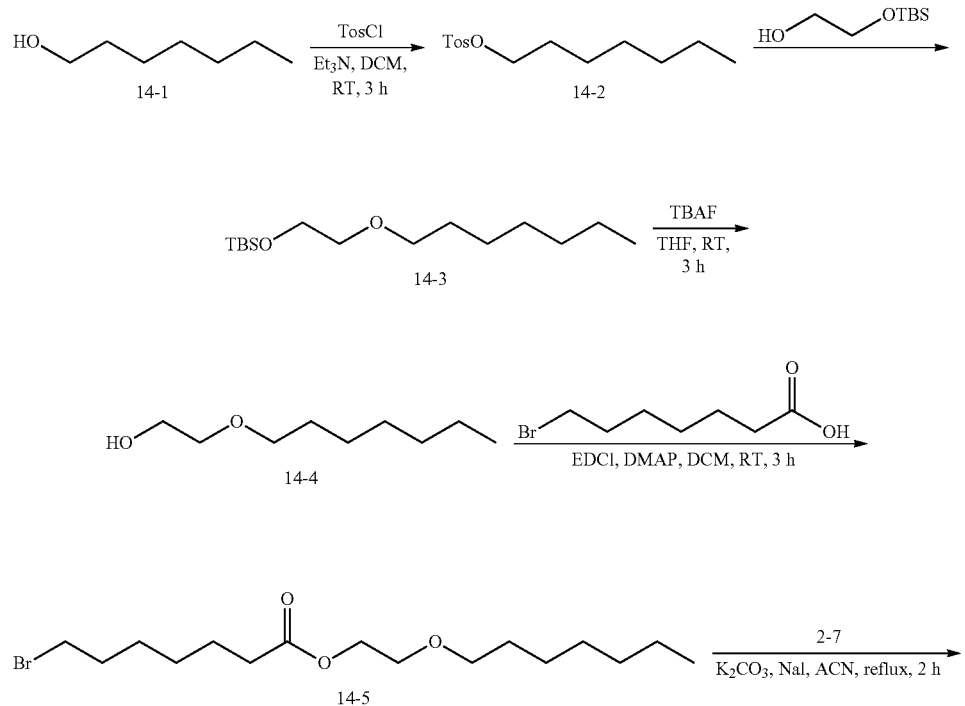

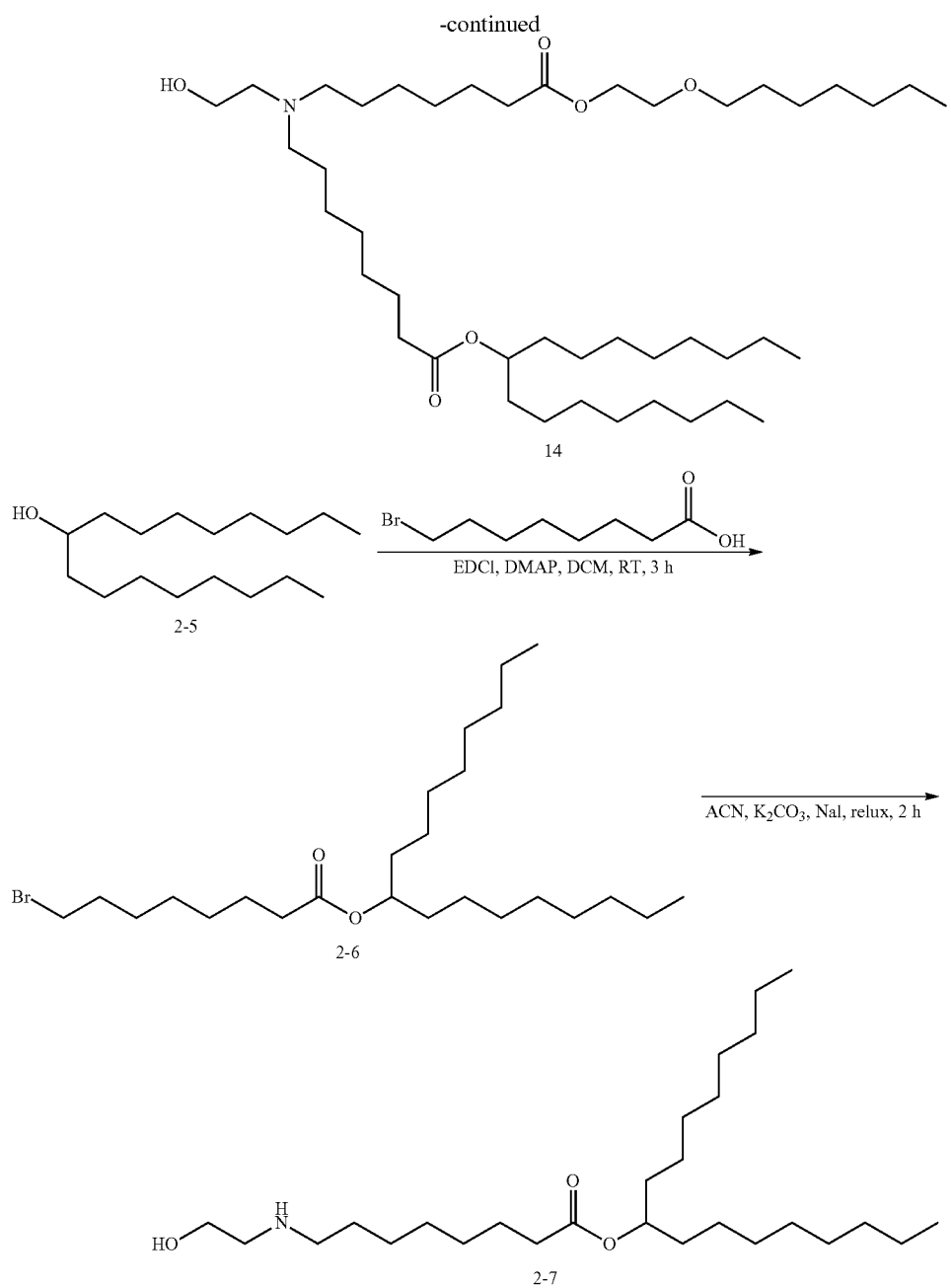

Step 1:

To a solution of compound 14-1 (3.0 g) and triethylamine (5.3 g) in dichloromethane (50 mL), p-toluenesulfonyl chloride (7.4 g) was added under ice bath conditions. The mixture was stirred at room temperature for 3. Then, the reaction mixture was diluted with DCM (30 mL) and washed with dilute hydrochloric acid and brine (100 mL). The organic layers were combined and dried over $Na_2SO_4$, and the solvent was removed in vacuum to give the crude product, which was purified by column chromatography (with a silica gel column and a n-hexane solution containing 0-10% EA (v/v) as the eluent), to give a compound 14-2 (6.0 g, 86% yield).

Step 2:

To a solution of tert-butyl dimethylhydroxyethoxysilane (2.0 g) in DMF (20 mL), NaH (680 mg, 60%) was added under ice bath conditions. The mixture was stirred at 0° C. for half an hour before 14-2 was slowly added to the solution, which was then stirred at 80° C. for 2 h. After the solution was cooled to room temperature, it was quenched by adding saturated ammonium chloride solution and extracted with ethyl acetate. The organic layers were combined and dried over $Na_2SO_4$, and the solvent was removed in vacuum to give the crude product, which was purified by column chromatography (with a silica gel column and a n-hexane solution containing 0-10% EA (v/v) as the eluent), to give a compound 14-3 (2.5 g, 80% yield).

Step 3:

To a solution of compound 14-3 (2.5 g) in anhydrous tetrahydrofuran (20 mL), 1M TBAF solution was added under ice bath conditions. The solution was warmed to room temperature and stirred at room temperature for 2 h, and saturated ammonium chloride solution was then added thereto. After that, the solution was diluted with water and extracted with ethyl acetate. The organic layers were combined and dried over $Na_2SO_4$, and the solvent was removed in vacuum to give the crude product, which was purified by column chromatography (with a silica gel column and a n-hexane solution containing 0-60% EA (v/v) as the eluent), to give a compound 14-4 (1.4 g, 96% yield).

Step 4:

To a solution of compound 14-4 (1.4 g) in DCM (20 mL), 4-dimethylaminopyridine (DMAP, 1.07 g), 7-bromoheptanoic acid (2.01 g) and 1-ethyl-(3-dimethylaminopropyl) (EDCI, 2.01 g) were sequentially added. The reaction mixture was stirred at 25° C. for 12 h. The reaction mixture was diluted with DCM (30 mL) and washed with saturated $NaHCO_3$ (100 mL) and brine (100 mL). The organic layers were combined and dried over $Na_2SO_4$, and the solvent was removed in vacuum to give the crude product, which was purified by column chromatography (with a silica gel column and a n-hexane solution containing 0-1% EA (v/v) as the eluent), and the pure product fraction was evaporated to give a compound 14-5 (2.10 g, 68% yield).

Step 5:

Compound 14-5 (500 mg) was dissolved in acetonitrile (10 ml) and stirred at room temperature. Subsequently, NaI (191 mg), $K_2CO_3$ (527 mg) and compound 2-7 (673 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 14 (820 mg, 81% yield).

$^1$H NMR (400 MHz, Chloroform-d) δ 4.78 (s, 1H), 4.21 (s, 2H), 3.64 (d, J=5.0 Hz, 2H), 3.60 (s, 2H), 3.53 (s, 2H), 2.55 (s, 2H), 2.48 (s, 4H), 2.24 (s, 4H), 1.71-1.65 (m, 4H), 1.58 (d, J=6.4 Hz, 4H), 1.53 (s, 4H), 1.51 (s, 2H), 1.38-1.35 (m, 6H), 1.35-1.33 (m, 8H), 1.32 (d, J=1.0 Hz, 4H), 1.32-1.31 (m, 10H), 1.29 (s, 4H), 1.29 (s, 2H), 1.29-1.27 (m, 8H), 0.97-0.82 (m, 9H).

Example 7

Synthesis of Compound 17

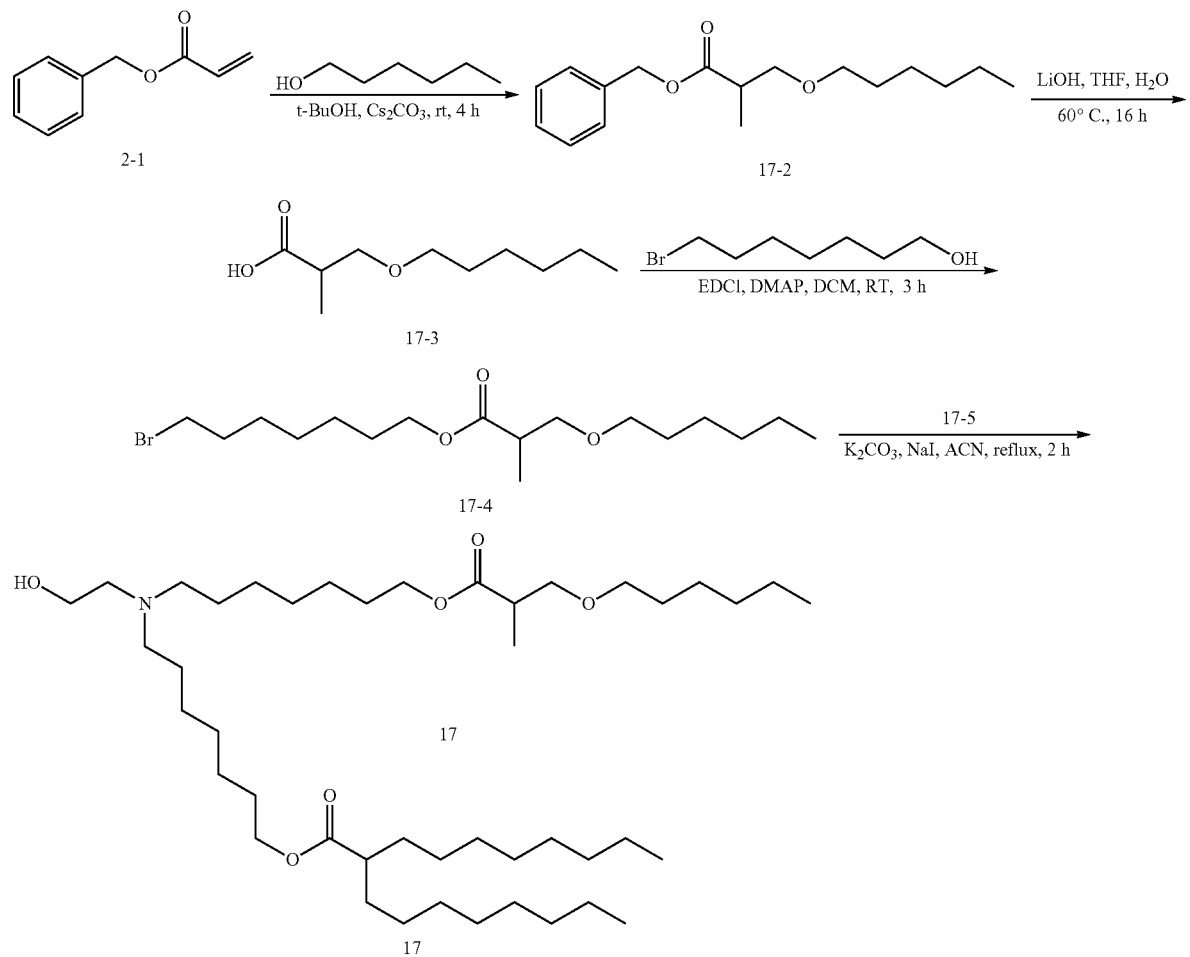

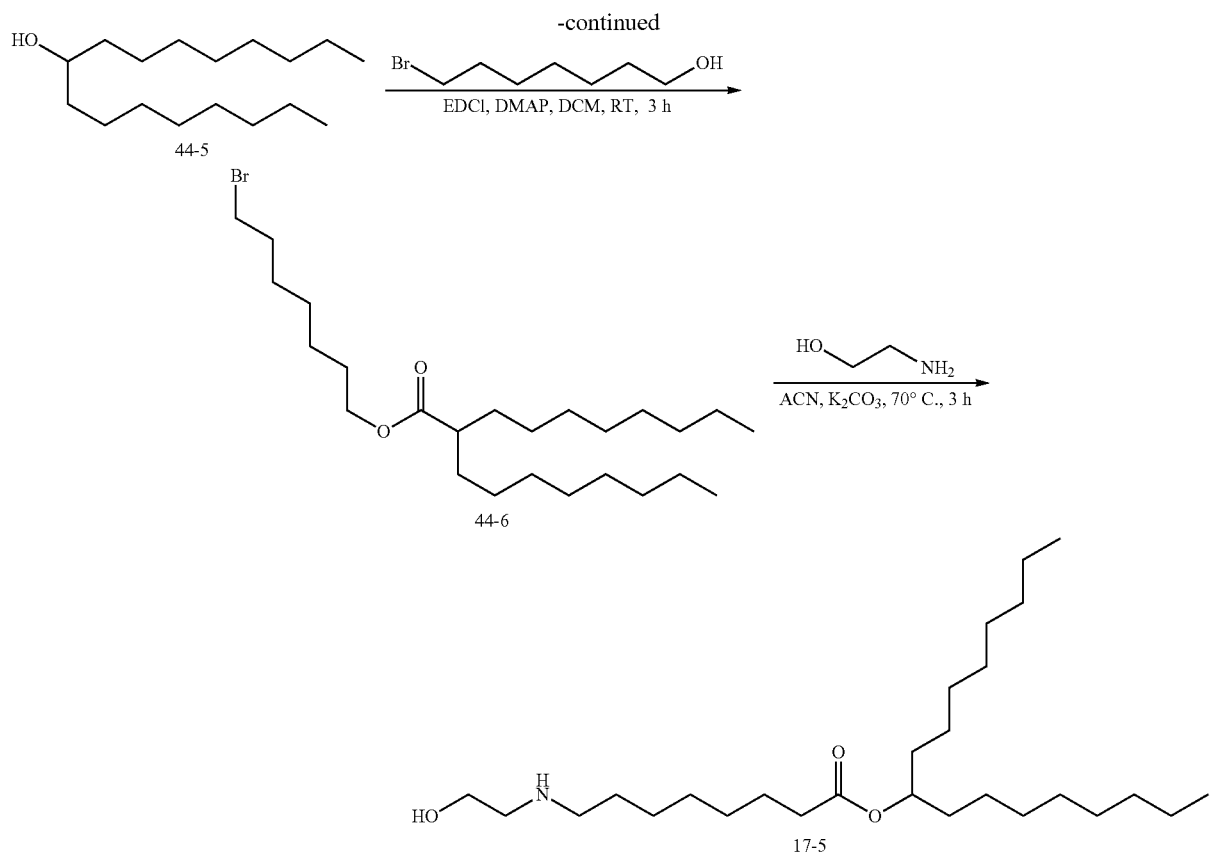

Step 1:

To a solution of compound 2-1 (5.00 g) in tert-butanol (40 mL), n-hexanol (2.90 g) and cesium carbonate (27.8 g) were added sequentially. After the solution was stirred at room temperature for 4 h, the spot plate (petroleum ether:ethyl acetate=10:1) showed the generation of new spots. The reaction solution was filtered. The resulting filtrate was concentrated to obtain a crude product, which was then purified by column chromatography (with a silica gel column and a petroleum ether solution containing 0-10% ethyl acetate (v/v) as the eluent), to give a compound 17-2 (3.14 g, 39.8% yield).

Step 2:

To a solution of compound 17-2 (3.00 g) in THF (20 mL) and water (20 mL), lithium hydroxide (1.03 g) was added. The mixture was stirred at 60° C. for 16 h. TLC showed generation of a spot with increased polarity. The reaction mixture was concentrated to remove tetrahydrofuran, diluted with water, and extracted once with ethyl acetate (30 mL). The aqueous phase was adjusted to pH=2 with dilute hydrochloric acid and extracted twice with ethyl acetate (30 mL). The organic layers were combined and concentrated to give a compound 17-3 (1.80 g, 88.7% yield).

Step 3:

Compound 17-3 (2.0 g) was dissolved in DCM (20 ml) and stirred at room temperature. 1-ethyl-(3-dimethylaminopropyl)carbodiimide hydrochloride (EDCI, 3.1 g), 4-dimethylaminopyridine (DMAP, 2.0 g) and 7-bromo-1-heptanol (2.3 g) were weighed sequentially, and added to the reaction system in batches and stirred at room temperature for 3 h. A small amount of the reaction solution was diluted and spotted on the plate in control with a 2-3 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min), to give a colorless oily liquid compound 17-4 (2.8 g, 74% yield).

Step 4:

To a solution of compound 44-5 (2.00 g) in DCM (15 mL), 4-dimethylaminopyridine (DMAP, 200 mg) and 7-bromo-1-heptanol (1.51 g) were added sequentially, and the mixture was stirred at 25° C. for 5 min. Subsequently, 1-ethyl-(3-dimethylaminopropyl) (EDCI, 1.62 g) was added, and then the reaction mixture was stirred at 25° C. for 1 h. TLC showed complete disappearance of the starting compound 44-5. The reaction mixture was concentrated to obtain a crude product, which was then purified by column chromatography (with a silica gel column and a petroleum ether solution containing 0-1% EA (v/v) as the eluent), and the pure product fraction was evaporated to give a compound 44-6 (2.4 g, 74% yield).

Step 5:

To a solution of compound 44-6 (2.0 g) and ethanolamine (530 mg) in acetonitrile (50 mL), potassium carbonate (1.80 g) was added. The mixture was stirred at 70° C. for 3 h. TLC showed complete disappearance of compound 44-6 and generation of a spot with increased polarity. The reaction solution was filtered. The resulting filtrate was concentrated to obtain a crude product, which was then was mixed with appropriate amount of silica gel and DCM, and purified (25 g normal phase column, PE/EA, 0-0% 5 min, 0-10% 20 min, 10-10% 5 min, a flow rate of 20 ml/min), to give a colorless oily liquid compound 17-5 (1.0 g, 53.8% yield).

Step 6:

Compound 17-4 (500 mg) was dissolved in acetonitrile (10 ml) and stirred at room temperature. Subsequently, NaI (191 mg), K$_2$CO$_3$ (527 mg) and compound 17-5 (673 mg) were weighed sequentially, and added to the reaction system in batches and heated and stirred at 85° C. under reflux for 2 h. A small amount of the reaction solution was diluted and spotted on the plate (DCM/MeOH=10/1, id aqueous ammonia, phosphomolybdic acid). New spots with less polarity than that of 17-5 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 17 (725 mg, 70% yield).

$^1$H NMR (400 MHz, Chloroform-d) δ 4.15-4.03 (m, 4H), 3.56-3.45 (m, 6H), 2.75 (s, 1H), 2.55 (d, J=3.8 Hz, 2H), 2.48 (d, J=1.0 Hz, 4H), 2.29 (s, 1H), 1.65 (s, 4H), 1.50-1.46 (m, 10H), 1.40-1.38 (s, 4H), 1.36 (d, J=0.6 Hz, 2H), 1.34 (d, J=0.6 Hz, 4H), 1.32 (d, J=1.0 Hz, 10H), 1.32-1.30 (m, 10H), 1.28 (d, J=1.2 Hz, 12H), 1.18 (s, 3H), 0.94-0.84 (m, 9H).

Example 8

Synthesis of Compound 28

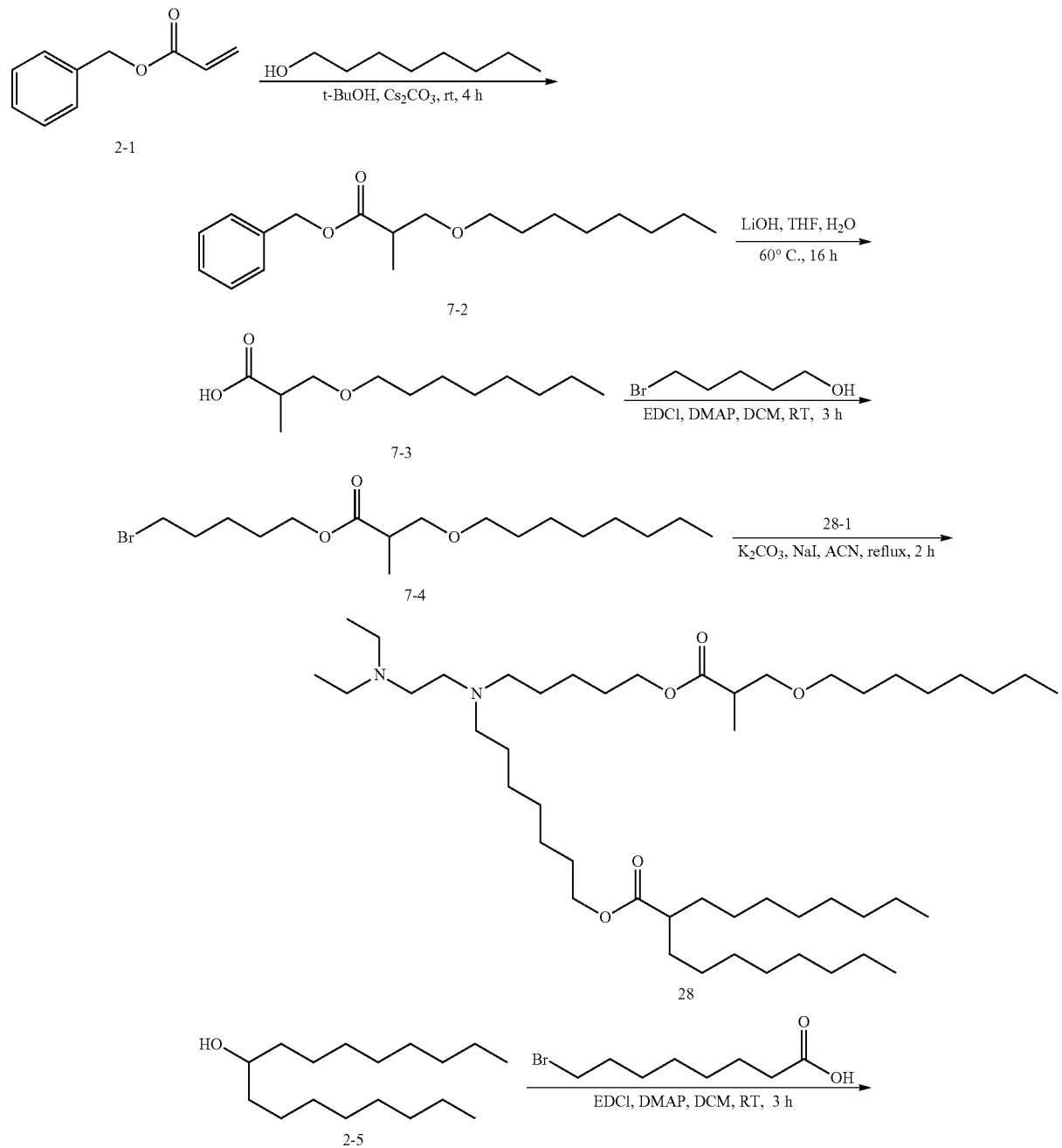

-continued

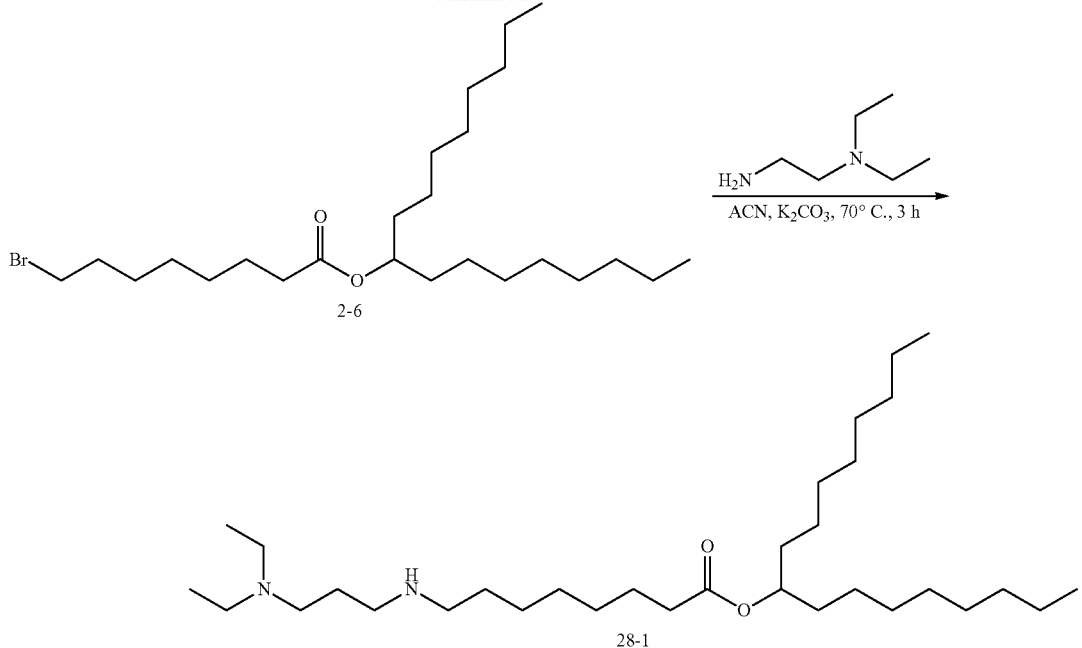

Step 1:

To a solution of compound 2-6 (2.0 g) and N,N-di ethyl ethylenediamine (755 mg) in acetonitrile (50 mL), potassium carbonate (1.2 g) was added. The mixture was stirred at 70° C. for 3 h. A spot with increased polarity was generated. The reaction solution was filtered. The resulting filtrate was concentrated to obtain a crude product, which was then was mixed with appropriate amount of silica gel and DCM, and purified (25 g normal phase column, DCM/MeOH, 0.1% aqueous ammonia, 0-0% 10 min, 0-7.5% 20 min, 7.5-7.5% 5 min, a flow rate of 25 ml/min), to give a colorless oily liquid compound 28-1 (900 mg, 30% yield).

Step 2:

Compound 28-1 (500 mg) was dissolved in acetonitrile (10 ml) and stirred at room temperature. Subsequently, NaI (146 mg), $K_2CO_3$ (406 mg) and compound 7-4 (425 mg) were weighed sequentially, and added to the reaction system in batches and heated and stirred at 85° C. under reflux for 2 h. A small amount of the reaction solution was diluted and spotted on the plate (DCM/MeOH=10/1, id aqueous ammonia, phosphomolybdic acid). New spots were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 7 (94 mg, 11% yield).

$^1$H NMR (400 MHz, Chloroform-d) δ 4.78 (s, 1H), 4.09 (d, J=2.2 Hz, 2H), 3.73-3.60 (m, 4H), 2.75 (s, 1H), 2.69-2.57 (m, 8H), 2.51-2.40 (m, 4H), 2.31-2.17 (m, 2H), 1.72-1.65 (m, 4H), 1.60-1.50 (m, 10H), 1.48 (s, 2H), 1.36 (d, J=0.6 Hz, 4H), 1.35-1.30 (m, 20H), 1.30-1.26 (m, 16H), 1.19 (s, 3H), 1.00 (s, 6H), 0.90 (s, 9H).

Example 9

Synthesis of Compound 29

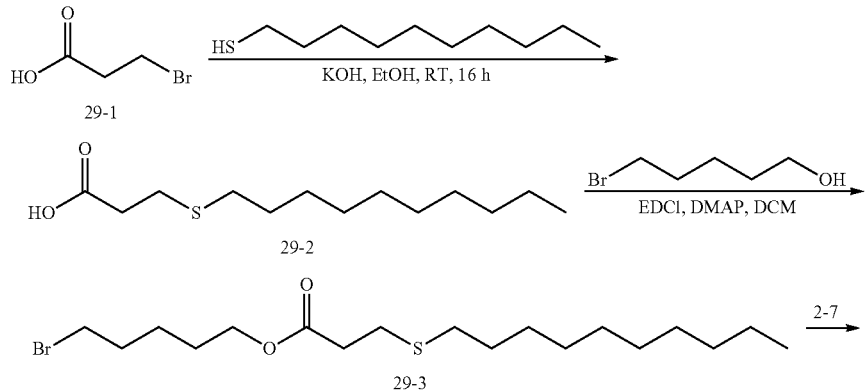

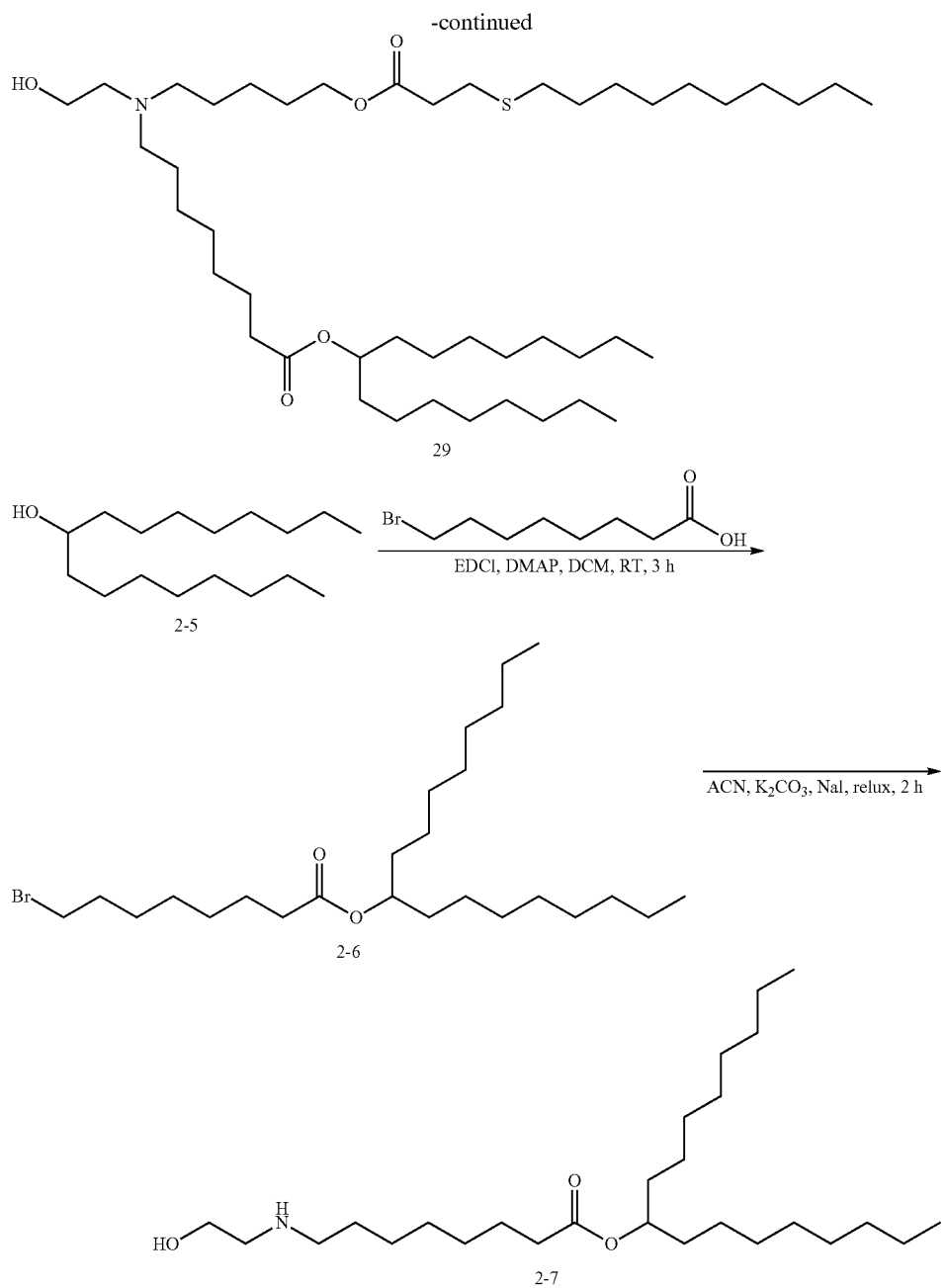

1-decanethiol (2.28 g) and KOH(2.20 g) were dissolved in ethanol (20 ml) and stirred at room temperature. Subsequently, compound 29-1 (2.00 g) was weighed and added to the reaction system in batches. The mixture was stirred at room temperature overnight. TLC (PE/EA=3/1, phosphomolybdic acid) showed generation of new spots. 200 ml of water was added into the reaction mixture, and the pH was adjusted to near 3 by adding concentrated HCl dropwise. The above mixture was extracted with 600 ml of ethyl acetate, and the organic phase was dried over $Na_2SO_4$ and evaporated under reduced pressure. It was mixed with appropriate amount of DCM and silica gel, and purified (30 g normal phase column, PE/EA, 0-0% 10 min, 0-2% 20 min, 2-2% 5 min, a flow rate of 30 ml/min). The spot plate was monitored, and fractions of the pure product were evaporated to give white solid 29-2 (950 mg, 30% yield).

Step 2:

Compound 29-2 (950 mg) was dissolved in DCM (10 ml) and stirred at room temperature. 1-ethyl-(3-dimethylaminopropyl)carbodiimide hydrochloride (EDCI, 924 mg), 4-dimethylaminopyridine (DMAP, 95 mg) and 5-bromo-1-pentanol (708 mg) were weighed sequentially, and added to the reaction system in batches and stirred at room temperature for 3 h. A small amount of the reaction solution was diluted and spotted on the plate in control with a 29-2 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min). The spot plate was monitored, and fractions of the pure product were evaporated to give a colorless oily liquid compound 29-3 (1.45 g, 95% yield).

Step 3:

Compound 29-3 (750 mg) was dissolved in acetonitrile (10 ml) and stirred at room temperature. Subsequently, NaI (170 mg), K$_2$CO$_3$ (350 mg) and compound 2-7 (559 mg) were weighed sequentially, and added to the reaction system in batches and heated and stirred at 85° C. under reflux for 2 h. A small amount of the reaction solution was diluted and spotted on the plate in control with a 2-7 standard sample (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min). The spot plate was monitored, and fractions of the pure product were evaporated to give a light yellow oily liquid compound 29 (850 mg).

$^1$H NMR (400 MHz, cdcl3) δ 4.86 (p, J=6.4 Hz, 1H), 4.09 (t, J=6.8 Hz, 2H), 3.56 (t, J=5.4 Hz, 2H), 2.77 (t, J=7.4 Hz, 2H), 2.61 (dt, J=11.8, 6.4 Hz, 4H), 2.51 (dd, J=14.4, 6.8 Hz, 6H), 2.28 (t, J=7.6 Hz, 2H), 1.70-1.55 (m, 6H), 1.50 (dd, J=16.6, 10.9 Hz, 8H), 1.40-1.21 (m, 46H), 0.88 (t, J=6.8 Hz, 9H).

Example 10

Synthesis of Compound 30

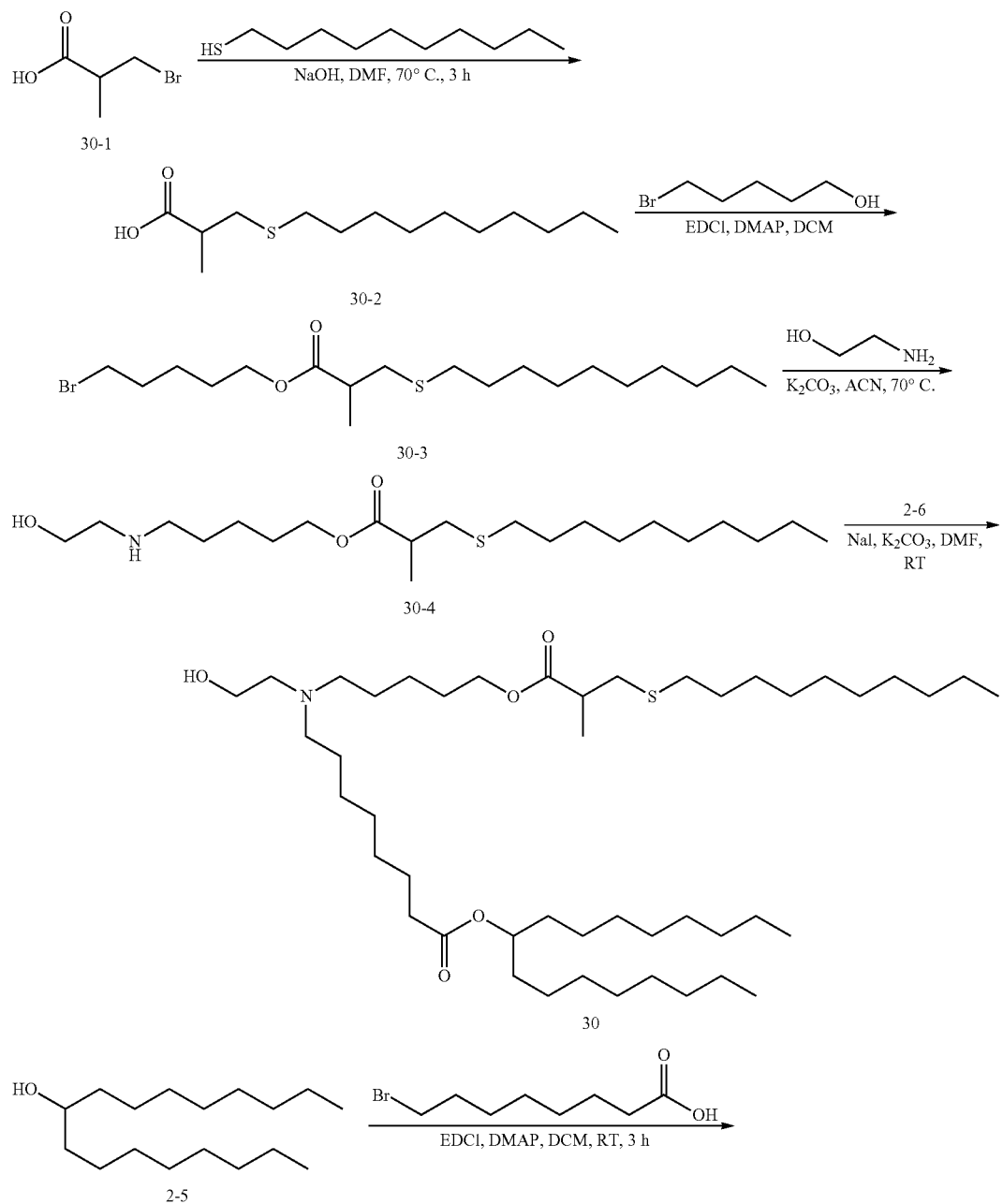

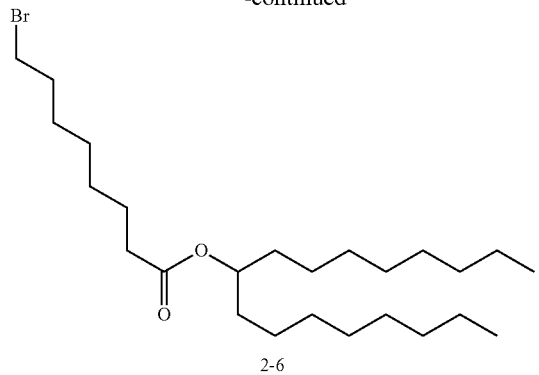

2-6

Step 1:
To a solution of compound 30-1 (2.00 g) in DMF (15 mL), 1-decanethiol (2.10 g) and sodium hydroxide (1.20 g) were added sequentially. The mixture was stirred at 70° C. for 3 h. TLC showed complete disappearance of the starting compound 30-1. The reaction solution was poured into $H_2O$ (50 mL) and extracted once with EA (20 mL). The aqueous phase was adjusted to pH=3 with a 2M dilute hydrochloric acid and extracted twice with EA (20 mL). The organic phases were combined, dried over anhydrous sodium sulfate, filtered under suction, and concentrated to give a compound 30-2 (1.70 g, 54% yield).

Step 2:
To a solution of compound 30-2 (1.70 g) in DCM (15 mL), 4-dimethylaminopyridine (DMAP, 160 mg) and 5-bromopentanol (1.31 g) were added sequentially. After stirring the mixture at 25° C. for 5 h, 1-ethyl-(3-dimethylaminopropyl)(EDCI, 1.56 g) was added, and the reaction mixture was stirred at 25° C. for 2 h. TLC showed complete disappearance of the starting compound 30-2. The reaction mixture was concentrated to obtain a crude product, which was then purified by column chromatography (with a silica gel column and a petroleum ether solution containing 0-1% EA (v/v) as the eluent), and the pure product fraction was evaporated to give a compound 30-3 (1.54 g, 57% yield).

Step 3:
To a solution of compound 30-3 (1.5 g) in ethanol (15 mL), ethanolamine (783 mg) was added. The mixture was stirred at 70° C. for 12 h. TLC showed a small amount of starting compound 30-3 remaining. The reaction mixture was concentrated to obtain a crude product, which was then purified by column chromatography (with a silica gel column and a dichloromethane solution containing 0-10% $CH_3OH$ (v/v) as the eluent, 0.1% aqueous ammonia added in methanol), and the pure product fraction was evaporated to give a compound 30-4 (824 mg, 58% yield).

Step 4:
To a solution of compound 30-4 (724 mg) in DMF (7 mL), heptadecan-9-yl 8-bromooctanoate (1.03 g), NaI (278 mg) and $K_2CO_3$ (770 mg) were added sequentially. The mixture was stirred at 50° C. for 12 h. TLC showed a small amount of starting compound 30-4 remaining. The reaction solution was poured into $H_2O$ (50 mL) and extracted three times with EA (20 mL). The organic phases were combined, washed twice with saturated saline (20 mL), dried over anhydrous sodium sulfate, filtered under suction, and concentrated to obtain a crude product, which was then purified by column chromatography (with a silica gel column and, as the eluent, a dichloromethane solution containing 0-10% $CH_3OH$ (v/v), 1% aqueous ammonia in methanol), and the pure product fraction was evaporated to give a compound 30 (1.02 g, 71% yield).

$^1$H NMR (400 MHz, Chloroform-d) δ 4.86 (dd, J=12.4, 6.0 Hz, 1H), 4.09 (t, J=8.0 Hz, 2H), 3.54 (t, J=6.0 Hz, 2H), 2.83 (d, J=7.0 Hz, 1H), 2.73-2.38 (m, 12H), 2.27 (t, J=7.2 Hz, 3H), 1.68-1.18 (m, 61H), 0.87 (t, J=6.8 Hz, 9H).

Example 11

Synthesis of Compound 35

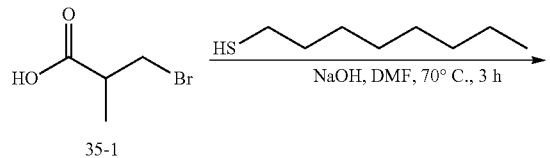

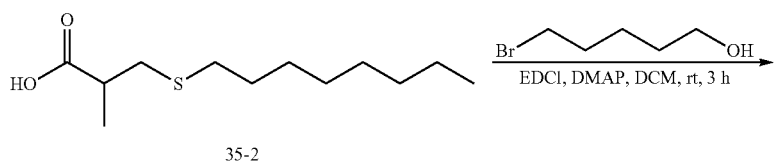

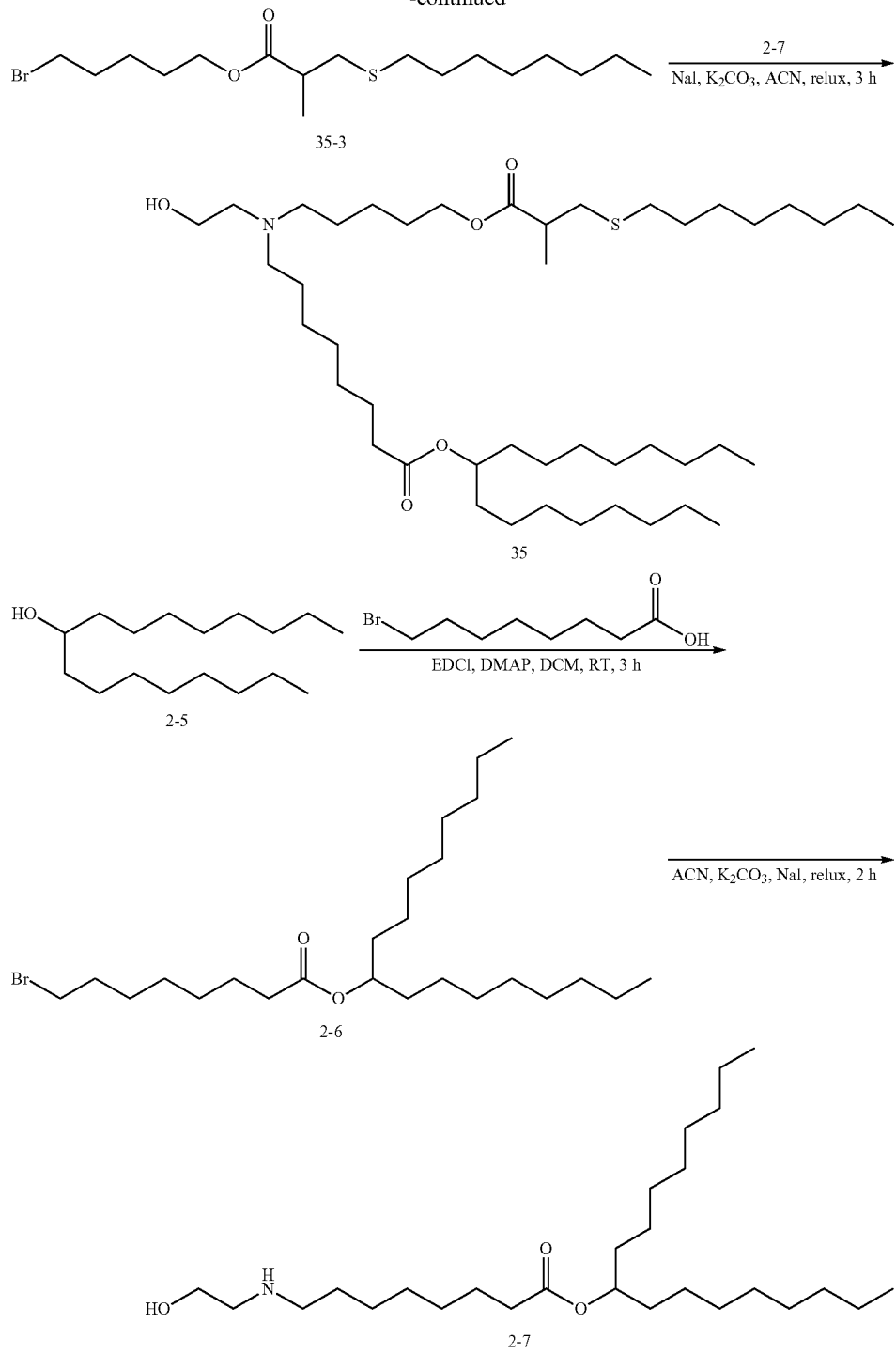

Step 1:

To a solution of compound 35-1 (2.00 g) in DMF (15 mL), 1-octanethiol (2.10 g) and sodium hydroxide (1.20 g) were added sequentially. The mixture was stirred at 70° C. for 3 h. TLC showed complete disappearance of the starting compound 35-1. The reaction solution was poured into $H_2O$ (50 mL) and extracted once with EA (20 mL). The aqueous phase was adjusted to pH=3 with a 2M dilute hydrochloric acid and extracted three times with EA (20 mL). The organic phases were combined, dried over anhydrous sodium sulfate, filtered under suction, and concentrated to give a compound 35-2 (1.80 g, 56.6% yield).

Step 2:

Compound 35-2 (1000 mg) was dissolved in DCM (10 ml) and stirred at room temperature. 1-ethyl-(3-dimethylaminopropyl)carbodiimide hydrochloride (EDCI, 924 mg), 4-dimethylaminopyridine (DMAP, 95 mg) and 5-bromo-1-pentanol (708 mg) were weighed sequentially, and added to the reaction system in batches and stirred at room temperature for 3 h. A small amount of the reaction solution was diluted and spotted on the plate in control with a 35-2 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min). The spot plate was monitored, and fractions of the pure product were evaporated to give a colorless oily liquid compound 35-3 (1.30 g, 79.2% yield).

Step 3:

Compound 35-3 (750 mg) was dissolved in acetonitrile (10 ml) and stirred at room temperature. Subsequently, NaI (170 mg), K₂CO₃ (350 mg) and compound 2-7 (559 mg) were weighed sequentially, and added to the reaction system in batches and heated and stirred at 85° C. under reflux for 3 h. A small amount of the reaction solution was diluted and spotted on the plate in control with a 35-3 standard sample (DCM/MeOH=10/1, id aqueous ammonia, phosphomolybdic acid). New spots with less polarity than that of 35-3 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min). The spot plate was monitored, and fractions of the pure product were evaporated to give a light yellow oily liquid compound 35(830 mg, 56.9% yield).

$^1$H NMR (400 MHz, Chloroform-d) δ 4.86 (dd, J=12.4, 6.0 Hz, 1H), 4.09 (t, J=8.0 Hz, 2H), 3.54 (t, J=6.0 Hz, 2H), 2.83 (d, J=7.0 Hz, 1H), 2.73-2.38 (m, 12H), 2.27 (t, J=7.2 Hz, 3H), 1.68-1.18 (m, 61H), 0.87 (t, J=6.8 Hz, 9H).

Example 12

Synthesis of Compound 36

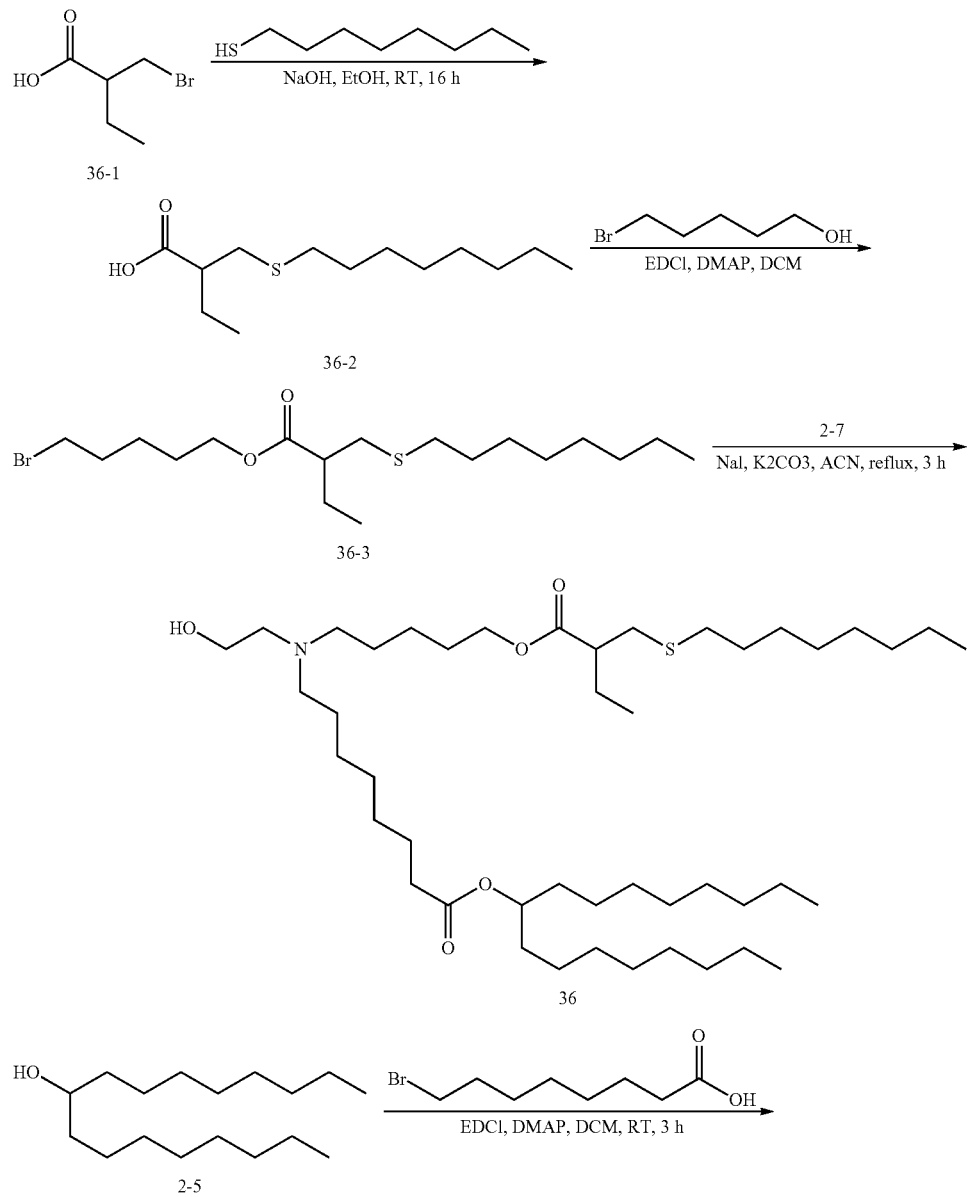

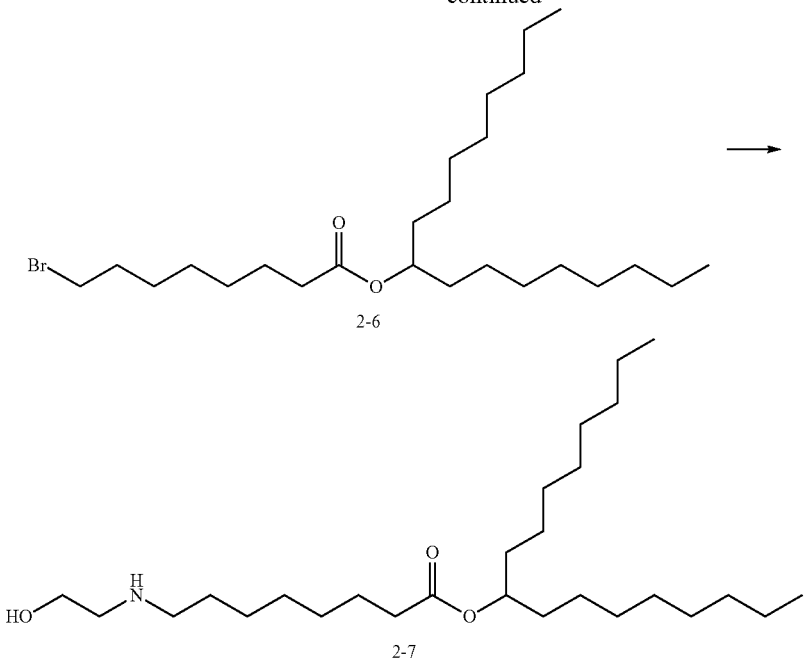

Step 1: 1-octanethiol (2.50 g) and NaOH (2.20 g) were dissolved in ethanol (20 ml) and stirred at room temperature. Subsequently, compound 36-1 (2.00 g) was weighed and added to the reaction system in batches. The mixture was stirred at room temperature overnight. TLC (PE/EA=3/1, phosphomolybdic acid) showed generation of new spots. 200 ml of water was added into the reaction mixture, and the pH was adjusted to near 3 by adding concentrated HCl dropwise. The above mixture was extracted with 600 ml of ethyl acetate, and the organic phase was dried over $Na_2SO_4$ and evaporated under reduced pressure. It was mixed with appropriate amount of DCM and silica gel, and purified (30 g normal phase column, PE/EA, 0-0% 10 min, 0-2% 20 min, 2-2% 5 min, a flow rate of 30 ml/min). The spot plate was monitored, and fractions of the pure product were evaporated to give white solid 36-2 (1.09 g, 40.2% yield).

Step 2:

Compound 36-2 (1000 mg) was dissolved in DCM (10 ml) and stirred at room temperature. 1-ethyl-(3-dimethylaminopropyl)carbodiimide hydrochloride (EDCI, 924 mg), 4-dimethylaminopyridine (DMAP, 95 mg) and 5-bromo-1-pentanol (708 mg) were weighed sequentially, and added to the reaction system in batches and stirred at room temperature for 3 h. A small amount of the reaction solution was diluted and spotted on the plate in control with a 36-2 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min). The spot plate was monitored, and fractions of the pure product were evaporated to give a colorless oily liquid compound 36-3 (1.20 g, 74.7% yield).

Step 3:

Compound 36-3 (750 mg) was dissolved in acetonitrile (10 ml) and stirred at room temperature. Subsequently, NaI (170 mg), $K_2CO_3$ (350 mg) and compound 2-7 (559 mg) were weighed sequentially, and added to the reaction system in batches and heated and stirred at 85° C. under reflux for 3 h. A small amount of the reaction solution was diluted and spotted on the plate in control with a 2-7 standard sample (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min). The spot plate was monitored, and fractions of the pure product were evaporated to give a light yellow oily liquid compound 35 (830 mg, 56.9% yield).

$^1$H NMR (400 MHz, Chloroform-d) δ 4.86 (dd, J=12.4, 6.0 Hz, 1H), 4.09 (t, J=8.0 Hz, 2H), 3.54 (t, J=6.0 Hz, 2H), 2.83 (d, J=7.0 Hz, 1H), 2.73-2.38 (m, 14H), 2.27 (t, J=7.2 Hz, 2H), 1.68-1.18 (m, 57H), 0.87 (t, J=6.8 Hz, 9H).

Example 13

Synthesis of Compound 41

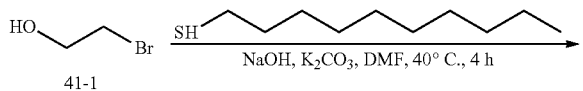

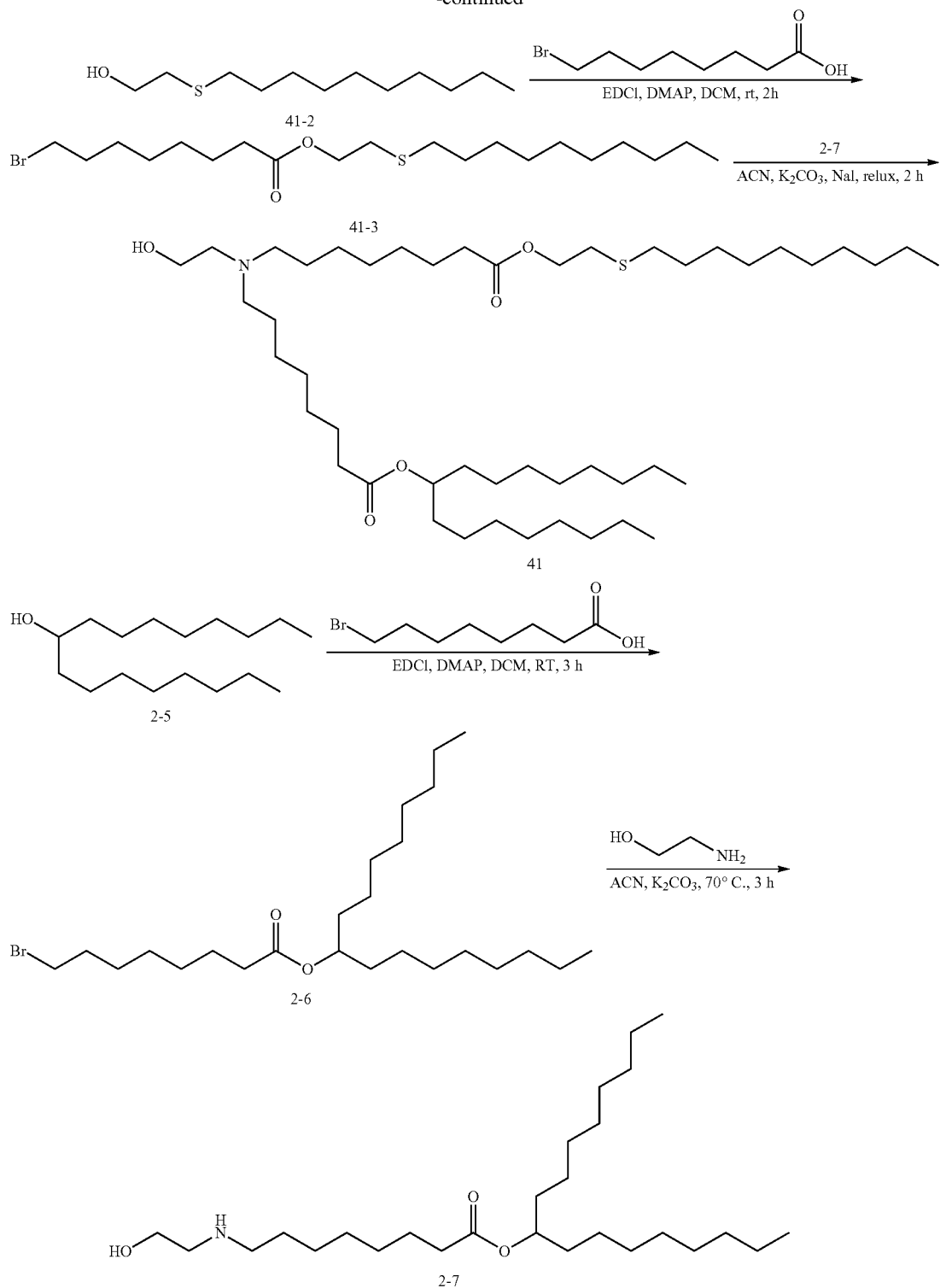

Step 1:

To a solution of compound 41-1 (2.00 g) in DMF (15 mL), 1-decanethiol (2.30 g) and sodium hydroxide (1.20 g) were added sequentially. The mixture was stirred at 40° C. for 4 h. TLC showed complete disappearance of the starting compound 41-1. The reaction solution was poured into H₂O (50 mL) and extracted once with ethyl acetate (20 mL). The aqueous phase was adjusted to pH=3 with a 2M dilute hydrochloric acid and extracted three times with ethyl acetate (20 mL). The organic phases were combined, dried over anhydrous sodium sulfate, filtered under suction, and concentrated to give a compound 41-2 (1.80 g, 56.6% yield).

Step 2:

Compound 41-2 (1000 mg) was dissolved in DCM (10 ml) and stirred at room temperature. 1-ethyl-(3-dimethylaminopropyl)carbodiimide hydrochloride (EDCI, 1.05 g), 4-dimethylaminopyridine (DMAP, 560 mg) and 8-bromooctanoic acid (1.02 g) were weighed sequentially, and added to the reaction system in batches and stirred at room temperature for 2 h. A small amount of the reaction solution was diluted and spotted on the plate in control with a 41-2 standard sample (PE/EA=10/1, phosphomolybdic acid). New spots with reduced polarity were observed. The reaction solution was evaporated under reduced pressure. It was mixed with appropriate amount of silica gel and DCM, and purified (15 g normal phase column, PE/EA, 0-0% 5 min, 0-5% 20 min, 5-5% 5 min, a flow rate of 15 ml/min), to give a colorless oily liquid compound 41-3 (1.5 g, 77% yield).

Step 3:

Compound 41-3 (700 mg) was dissolved in acetonitrile (10 ml) and stirred at room temperature. Subsequently, NaI (170 mg), K$_2$CO$_3$ (350 mg) and compound 2-7 (559 mg) were weighed sequentially, and added to the reaction system in batches and heated and stirred at 85° C. under reflux for 3 h. A small amount of the reaction solution was diluted and spotted on the plate in control with a 2-7 standard sample (DCM/MeOH=10/1, id aqueous ammonia, phosphomolybdic acid). New spots with less polarity than that of 2-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), to give a light yellow oily liquid compound 41 (600 mg, 44.8% yield).

$^1$H NMR (400 MHz, Chloroform-d) δ 4.86 (p, J=6.4 Hz, 1H), 4.09 (t, J=6.8 Hz, 2H), 3.56 (t, J=5.4 Hz, 2H), 2.77 (t, J=7.4 Hz, 2H), 2.61 (dt, J=11.8, 6.4 Hz, 4H), 2.51 (dd, J=14.4, 6.8 Hz, 6H), 2.28 (t, J=7.6 Hz, 2H), 1.70-1.55 (m, 6H), 1.50 (dd, J=16.6, 10.8 Hz, 8H), 1.40-1.21 (m, 50H), 0.88 (t, J=6.8 Hz, 9H).

Example 14

Synthesis of Compound 44

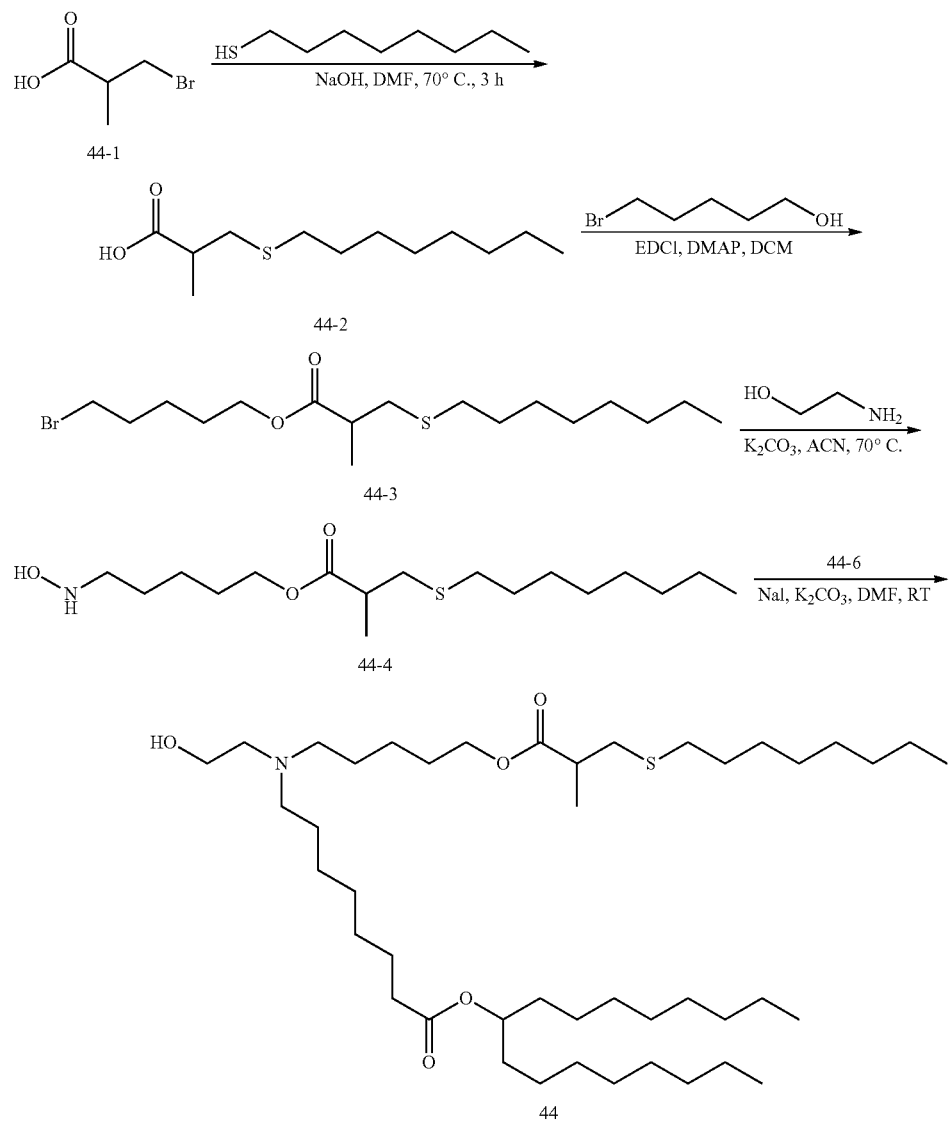

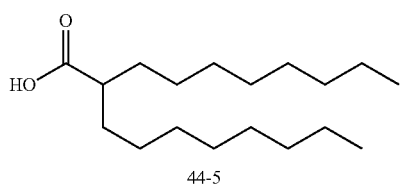

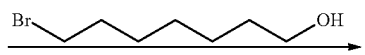

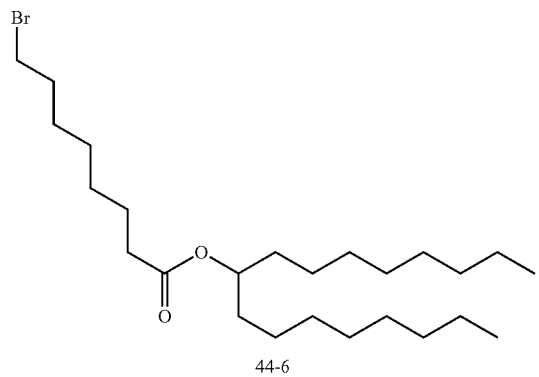

Step 1:

To a solution of compound 44-1 (2.00 g) in DMF (15 mL), 1-octanethiol (2.63 g) and sodium hydroxide (1.44 g) were added sequentially. The mixture was stirred at 70° C. for 3 h. TLC showed complete disappearance of the starting compound 44-1. The reaction solution was poured into $H_2O$ (50 mL) and extracted once with EA (20 mL). The aqueous phase was adjusted to pH=2 with a 2M dilute hydrochloric acid and extracted three times with EA (20 mL). The organic phases were combined, dried over anhydrous sodium sulfate, filtered under suction, and concentrated to give a compound 44-2 (1.63 g, 53% yield).

Step 2:

To a solution of compound 44-2 (1.63 g) in DMF (15 mL), 4-dimethylaminopyridine (DMAP, 172 mg) and 5-bromopentanol (1.41 g) were added sequentially. After stirring the mixture at 25° C. for 5 h, 1-ethyl-(3-dimethylaminopropyl)(EDCI, 1.75 g) was added, and the reaction mixture was stirred at 25° C. for 1 h. TLC showed complete disappearance of the starting compound 44-2. The reaction mixture was concentrated to obtain a crude product, which was then purified by column chromatography (with a silica gel column and a petroleum ether solution containing 0-1% EA (v/v) as the eluent), and the pure product fraction was evaporated to give a compound 44-3 (1.65 g, 62% yield).

Step 3:

To a solution of compound 44-3 (1.5 g) in acetonitrile (15 mL), ethanolamine (960 mg) and potassium carbonate (1.15 g) were added. The solution was stirred at 70° C. for 12 h. TLC showed a small amount of starting compound 44-3 remaining. The reaction mixture was concentrated to obtain a crude product, which was then purified by column chromatography (with a silica gel column and a dichloromethane solution containing 0-10% $CH_3OH$ (v/v) as the eluent, 0.1% aqueous ammonia added in methanol), and the pure product fraction was evaporated to give a compound 44-4(800 mg, 56% yield).

Step 4:

To a solution of compound 44-5 (2.00 g) in DCM (15 mL), 4-dimethylaminopyridine (DMAP, 200 mg) and 7-bromo-1-heptanol (1.51 g) were added sequentially. After stirring the mixture at 25° C. for 5 min, 1-ethyl-(3-dimethylaminopropyl)(EDCI, 1.62 g) was added, and the reaction mixture was stirred at 25° C. for 1 h. TLC showed complete disappearance of the starting compound 44-5. The reaction mixture was concentrated to obtain a crude product, which was then purified by column chromatography (with a silica gel column and a petroleum ether solution containing 0-1% EA (v/v) as the eluent), and the pure product fraction was evaporated to give a compound 44-6(2.40 g, 74% yield).

Step 5:

To a solution of compound 44-4 (800 mg) in DMF (7 mL), compound 44-6 (1.12 g), NaI (332 mg) and $K_2CO_3$ (918 mg) were added sequentially. The mixture was stirred at 50° C. for 12 h. TLC showed a small amount of starting compound 44-4 remaining. The reaction solution was poured into $H_2O$ (50 mL) and extracted three times with EA (20 mL). The organic phases were combined, washed twice with saturated saline (20 mL), dried over anhydrous sodium sulfate, filtered under suction, and concentrated to obtain a crude product, which was then purified by column chromatography (with a silica gel column and, as the eluent, a dichloromethane solution containing 0-10% $CH_3OH$ (v/v), 0.1% aqueous ammonia added in methanol), and the pure product fraction was evaporated to give a compound 44 (950 mg, 58% yield).

$^1$H NMR (400 MHz, Chloroform-d) δ 4.78 (s, 1H), 4.09 (d, J=3.2 Hz, 2H), 3.72-3.55 (m, 2H), 3.05-2.86 (m, 2H), 2.84 (s, 1H), 2.59-2.41 (m, 8H), 2.31-2.17 (m, 2H), 1.72-1.64 (m, 4H), 1.62-1.60 (s, 2H), 1.59-1.51 (m, 8H), 1.55 (s, 2H), 1.39-1.35 (m, 6H), 1.33 (d, J=3.0 Hz, 6H), 1.31 (d, J=3.0 Hz, 12H), 1.31-1.28 (m, 4H), 1.30-1.26 (m, 12H), 1.24 (s, 3H), 0.94-0.82 (m, 9H).

Example 15
Synthesis of Compound 46
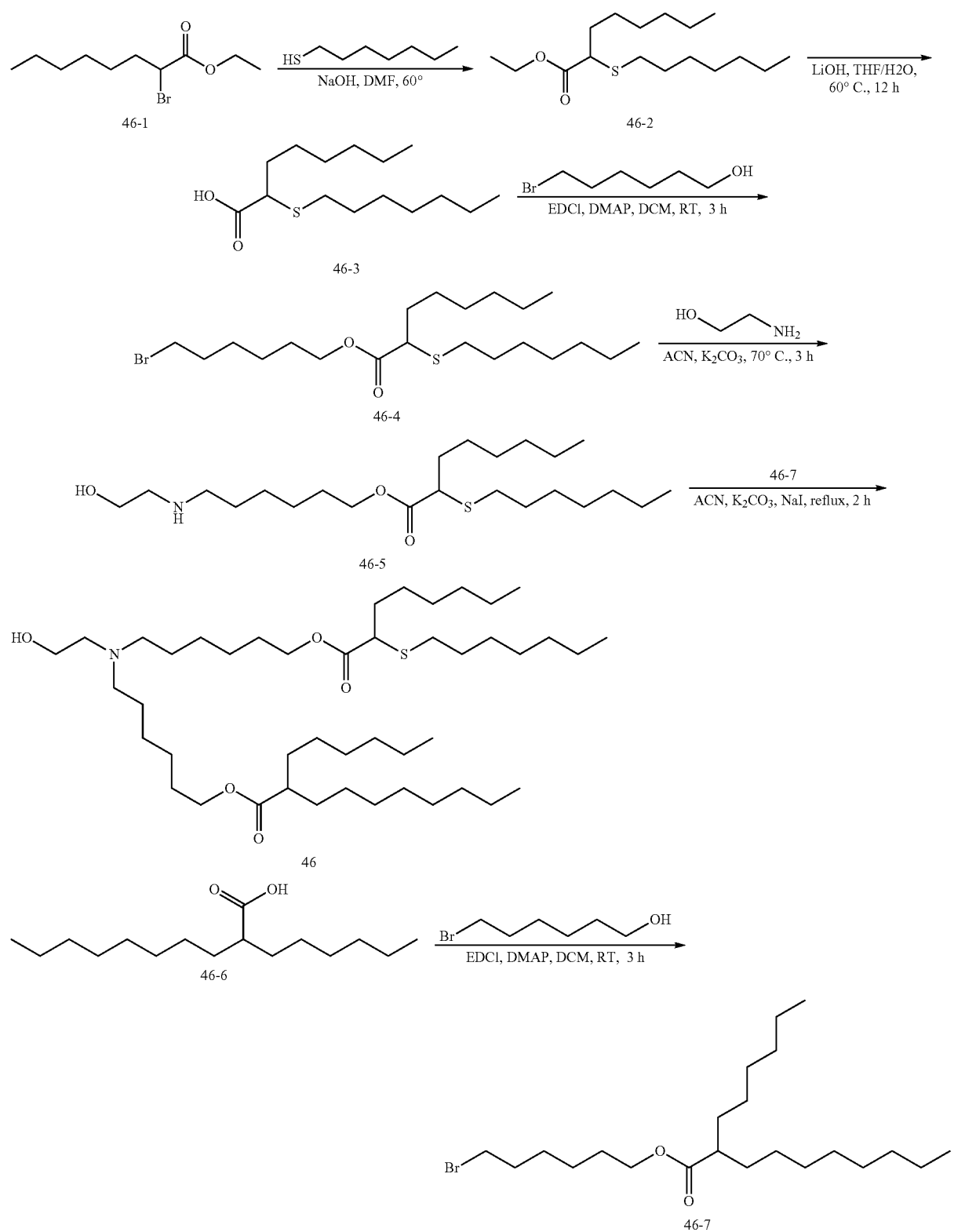

Step 1:

1-heptanethiol (2.1 g) and NaOH (1.0 g) were dissolved in DMF (20 ml) and stirred at room temperature. Subsequently, compound 46-1 (2.00 g) was weighed and added to the reaction system in batches. The mixture was stirred at 60° C. overnight. TLC (PE/EA=3/1, phosphomolybdic acid) showed generation of new spots. 200 ml of water was added into the reaction mixture, and the pH was adjusted to near 3 by adding concentrated HCl dropwise. The above mixture was extracted with 600 ml of ethyl acetate, and the organic phase was dried over $Na_2SO_4$ and evaporated under reduced pressure. It was mixed with appropriate amount of DCM and silica gel, and purified (30 g normal phase column, PE/EA, 0-0% 10 min, 0-2% 20 min, 2-2% 5 min, a flow rate of 30 ml/min). The spot plate was monitored, and fractions of the pure product were evaporated to give colorless oily liquid 46-2 (1.5 g, 62% yield).

Step 2:

To a solution of compound 46-2 (1.5 g) in THF (20 mL) and water, lithium hydroxide (360 mg) was added. The mixture was stirred at 60° C. for 16 h. TLC showed generation of a spot with increased polarity. The reaction mixture was concentrated to remove tetrahydrofuran, diluted with water, and extracted once with ethyl acetate (30 mL). The aqueous phase was adjusted to pH=2 with dilute hydrochloric acid and extracted twice with ethyl acetate (30 mL). The organic layers were combined and concentrated to give a compound 46-3 (1.2 g, 88% yield).

Step 3:

Compound 46-3 (1.2 g) was dissolved in DCM (10 ml) and stirred at room temperature. 1-ethyl-(3-dimethylaminopropyl)carbodiimide hydrochloride (EDCI, 1.01 g), 4-dimethylaminopyridine (DMAP, 534 mg) and 6-bromo-n-hexanol (792 mg) were weighed sequentially, and added to the reaction system in batches and stirred at room temperature for 3 h. A small amount of the reaction solution was diluted and spotted on the plate in control with a 46-3 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min). The spot plate was monitored, and fractions of the pure product were evaporated to give a colorless oily liquid compound 46-4 (1.6 g, 84% yield).

Step 4:

To a solution of compound 46-4 (1.6 g) and ethanolamine (447 mg) in acetonitrile (50 mL), potassium carbonate (1.52 g) was added. The mixture was reflux at 85° C. for 2 h. TLC showed complete disappearance of compound 46-4 and generation of a spot with increased polarity. The reaction solution was filtered. The resulting filtrate was concentrated to obtain a crude product, which was then was mixed with appropriate amount of silica gel and DCM, and purified (25 g normal phase column, PE/EA, 0-0% 5 min, 0-10% 20 min, 10-10% 5 min, a flow rate of 20 ml/min), to give a colorless oily liquid compound 46-5 (870 mg, 57% yield).

Step 5:

Compound 46-6 (2.0 g) was dissolved in DCM (10 ml) and stirred at room temperature. 1-ethyl-(3-dimethylaminopropyl)carbodiimide hydrochloride (EDCI, 1.79 g), 4-dimethylaminopyridine (DMAP, 950 mg) and 6-bromo-1-n-hexanol (1.41 mg) were weighed sequentially, and added to the reaction system and stirred at room temperature for 3 h. A small amount of the reaction solution was diluted and spotted on the plate in control with a 46-6 standard sample (PE/EA=10/1, phosphomolybdic acid). New spots with reduced polarity were observed. The reaction solution was evaporated under reduced pressure. It was mixed with appropriate amount of silica gel and DCM, and purified (25 g normal phase column, PE/EA, 0-0% 5 min, 0-5% 20 min, 5-5% 5 min, a flow rate of 15 ml/min). The spot plate was monitored, and fractions of the pure product were evaporated to give a colorless oily liquid compound 46-7 (2.8 g, 86% yield).

Step 6:

Compound 46-5 (500 mg) was dissolved in acetonitrile (10 ml) and stirred at room temperature. Subsequently, NaI (180 mg), $K_2CO_3$ (497 mg) and compound 46-7 (502 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots with less polarity than that of 46-7 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 46(700 mg, 77% yield).

$^1$H NMR (400 MHz, Chloroform-d) δ 4.10 (m, 4H), 3.64 (m, 3H), 2.61-2.42 (m, 8H), 2.29 (s, 1H), 1.98-1.90 (m, 2H), 1.67-1.61 (m, 6H), 1.59-1.45 (m, 8H), 1.43 (s, 4H), 1.41-1.37 (m, 4H), 1.37-1.33 (m, 10H), 1.33-1.30 (m, 14H), 1.30-1.26 (m, 12H), 0.95-0.83 (m, 12H).

Example 16

Synthesis of Compound 48

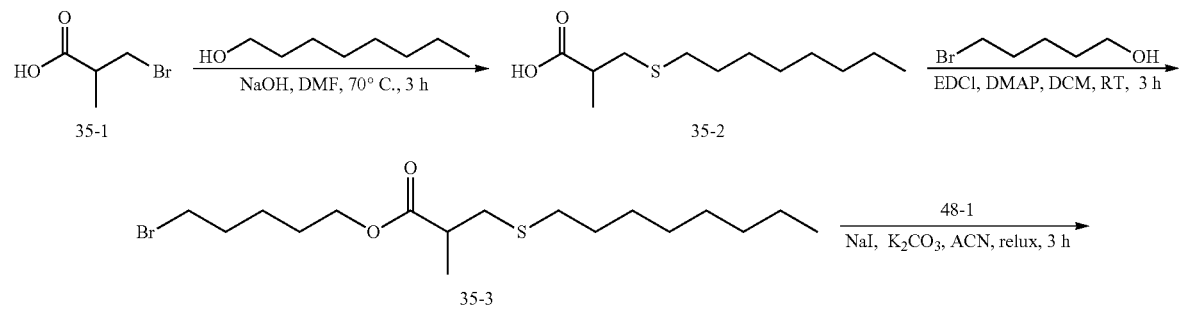

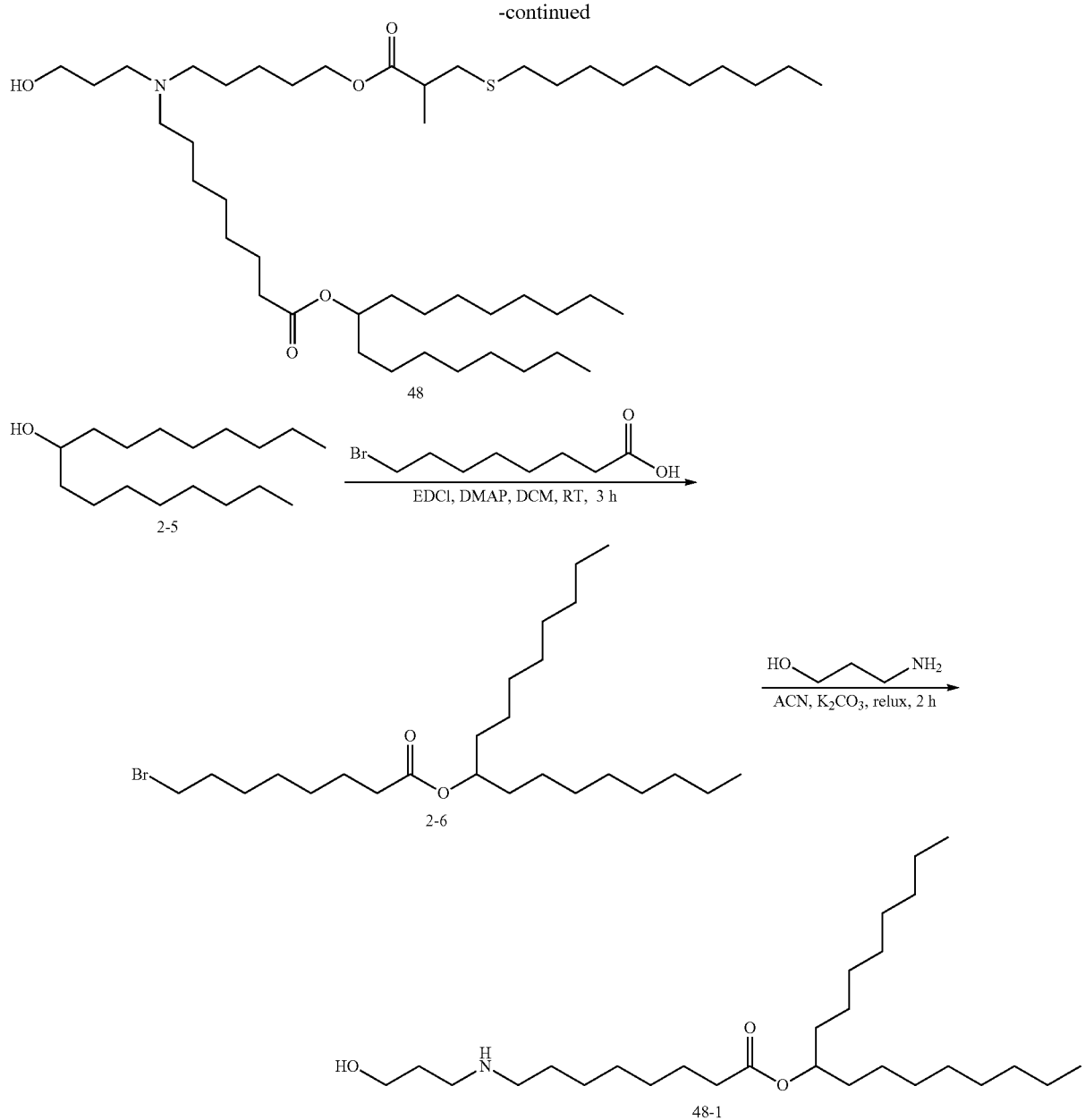

Step 1:

To a solution of compound 2-6 (8.0 g) and propanolamine (1.9 g) in acetonitrile (50 mL), potassium carbonate (7.19 g) was added. The mixture was reflux at 85° C. for 2 h. TLC showed complete disappearance of compound 2-6 and generation of a spot with increased polarity. The reaction solution was filtered. The resulting filtrate was concentrated to obtain a crude product, which was then was mixed with appropriate amount of silica gel and DCM, and purified (40 g normal phase column, PE/EA, 0-0% 5 min, 0-10% 20 min, 10-10% 5 min, a flow rate of 20 ml/min), to give a colorless oily liquid compound 48-1 (5.0 g, 63.3% yield).

Step 2:

Compound 35-3 (750 mg) was dissolved in acetonitrile (10 ml) and stirred at room temperature. Subsequently, NaI (170 mg), $K_2CO_3$ (350 mg) and compound 48-1 (620 mg) were weighed sequentially, and added to the reaction system in batches and heated and stirred at 85° C. under reflux for 3 h. A small amount of the reaction solution was diluted and spotted on the plate in control with a 48-1 standard sample (DCM/MeOH=10/1, id aqueous ammonia, phosphomolybdic acid). New spots with less polarity than that of 48-1 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min). The spot plate was monitored, and fractions of the pure product were evaporated to give a light yellow oily liquid compound 48 (650 mg, 69% yield).

$^1$H NMR (400 MHz, Chloroform-d) δ 4.78 (s, 1H), 4.09 (d, J=3.2 Hz, 2H), 3.65-3.56 (m, 2H), 3.00-2.88 (m, 3H), 2.56-2.40 (m, 8H), 2.31-2.17 (m, 2H), 1.73-1.63 (m, 6H), 1.62 (d, J=1.0 Hz, 2H), 1.59-1.50 (m, 8H), 1.58 (s, 2H), 1.40-1.35 (m, 6H), 1.34-1.30 (m, 18H), 1.30-1.27 (m, 16H), 1.24 (s, 3H), 0.95-0.82 (m, 9H).

Example 17
Synthesis of Compound 55
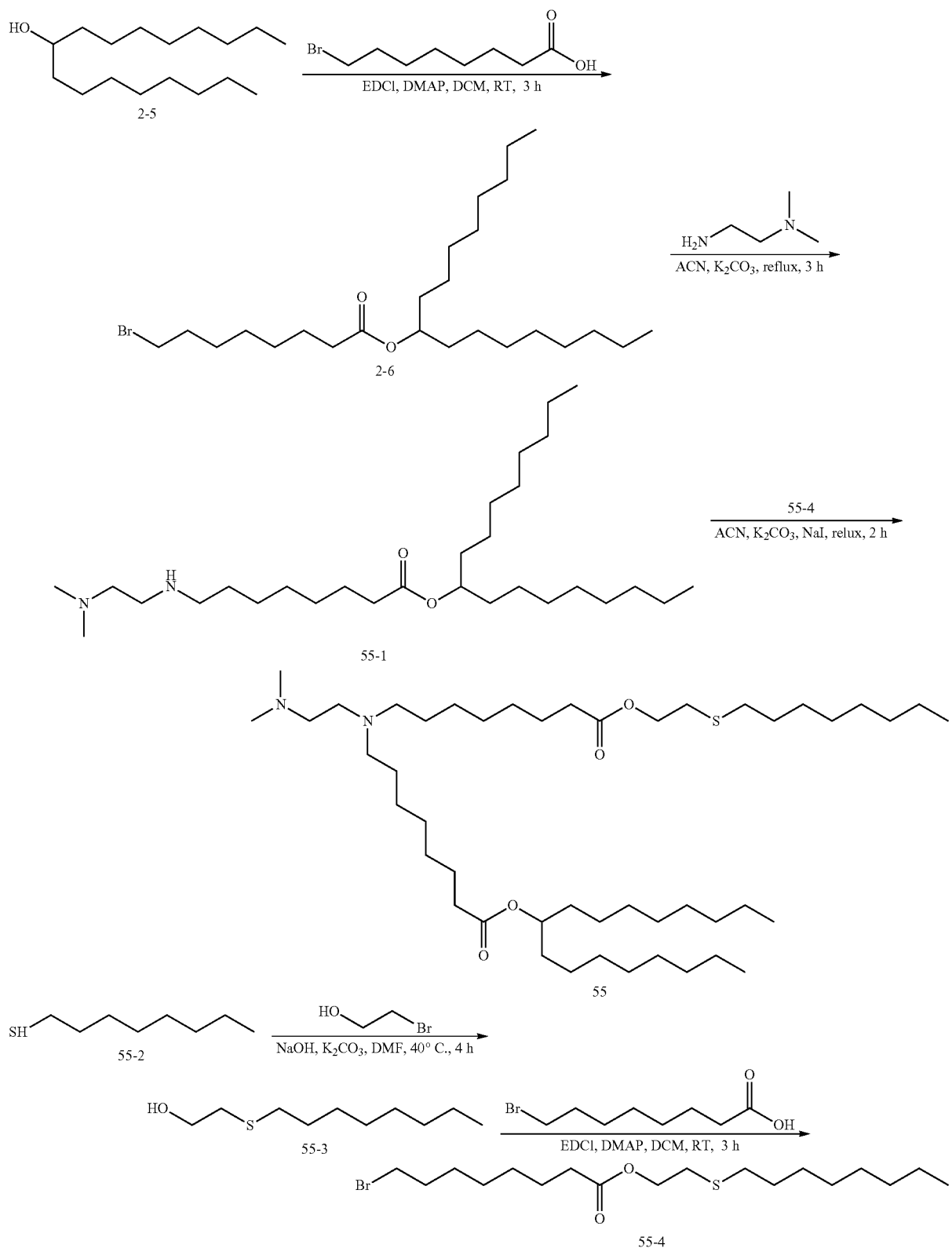

Step 1:

To a solution of compound 2-6 (4.0 g) and N,N-dimethylethylenediamine (1.53 g) in acetonitrile (50 mL), potassium carbonate (3.59 g) was added. The mixture was reflux at 85° C. for 3 h. TLC showed complete disappearance of compound 2-6 and generation of a spot with increased polarity. The reaction solution was filtered. The resulting filtrate was concentrated to obtain a crude product, which was then was mixed with appropriate amount of silica gel and DCM, and purified (25 g normal phase column, 0.1% $NH_3H_2O$, MeOH/DCM, 0-0% 5 min, 0-10% 20 min, 10-10% 5 min, a flow rate of 20 ml/min), to give a colorless oily liquid compound 55-1 (1.3 g, 32% yield).

Step 2:

To a solution of bromoethanol (2.00 g) in DMF (15 mL), compound 55-2 (1.93 g) and sodium hydroxide (1.20 g) were added sequentially. The mixture was stirred at 40° C. for 4 h. TLC showed complete disappearance of the starting compound 55-2. The reaction solution was poured into $H_2O$ (50 mL) and extracted once with ethyl acetate (20 mL). The aqueous phase was adjusted to pH=3 with a 2M dilute hydrochloric acid and extracted three times with ethyl acetate (20 mL). The organic phases were combined, dried over anhydrous sodium sulfate, filtered under suction, and concentrated to give a compound 55-3 (1.56 g, 62.3% yield).

Step 3:

Compound 55-3 (872 mg) was dissolved in DCM (10 ml) and stirred at room temperature. 1-ethyl-(3-dimethylaminopropyl)carbodiimide hydrochloride (EDCI, 1.05 g), 4-dimethylaminopyridine (DMAP, 560 mg) and 8-bromooctanoic acid (1.02 g) were weighed sequentially, and added to the reaction system in batches and stirred at room temperature for 2 h. A small amount of the reaction solution was diluted and spotted on the plate in control with a 55-3 standard sample (PE/EA=10/1, phosphomolybdic acid). New spots with reduced polarity were observed. The reaction solution was evaporated under reduced pressure. It was mixed with appropriate amount of silica gel and DCM, and purified (15 g normal phase column, PE/EA, 0-0% 5 min, 0-5% 20 min, 5-5% 5 min, a flow rate of 15 ml/min), to give a colorless oily liquid compound 55-4 (1.27 g, 70% yield).

Step 4:

Compound 55-1 (500 mg) was dissolved in acetonitrile (10 ml) and stirred at room temperature. Subsequently, NaI (146 mg), $K_2CO_3$ (406 mg) and compound 55-4 (393 mg) were weighed sequentially, and added to the reaction system in batches and heated and stirred at 85° C. under reflux for 3 h. A small amount of the reaction solution was diluted and spotted on the plate (DCM/MeOH=10/1, id aqueous ammonia, phosphomolybdic acid). New spots were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 55 (108 mg, 14% yield).

$^1$H NMR (400 MHz, Chloroform-d) δ 4.78 (s, 1H), 4.23 (s, 2H), 2.80 (s, 2H), 2.60 (s, 2H), 2.57 (s, 2H), 2.52 (s, 2H), 2.45 (s, 4H), 2.30 (s, 6H), 2.27 (s, 2H), 2.24 (s, 2H), 1.71-1.66 (m, 2H), 1.62 (s, 2H), 1.58-1.57 (d, J=6.8 Hz, 4H), 1.54 (d, J=6.8 Hz, 2H), 1.53-1.50 (m, 4H), 1.37 (d, J=1.0 Hz, 6H), 1.35-1.30 (m, 24H), 1.30-1.25 (m, 16H), 0.96-0.81 (m, 9H).

Example 18

Synthesis of Compound 57

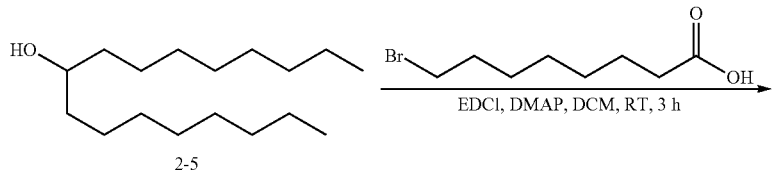

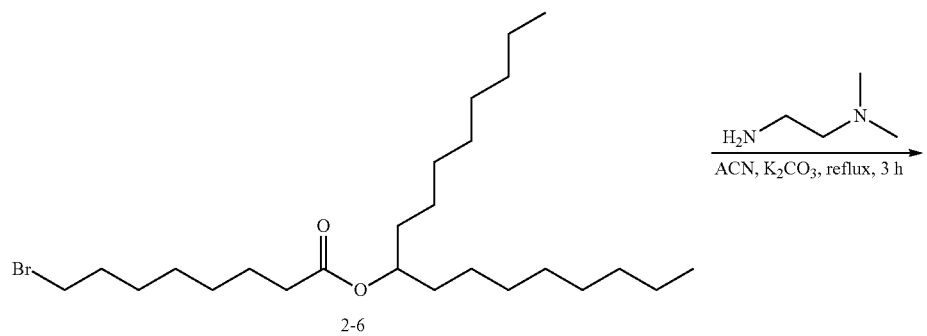

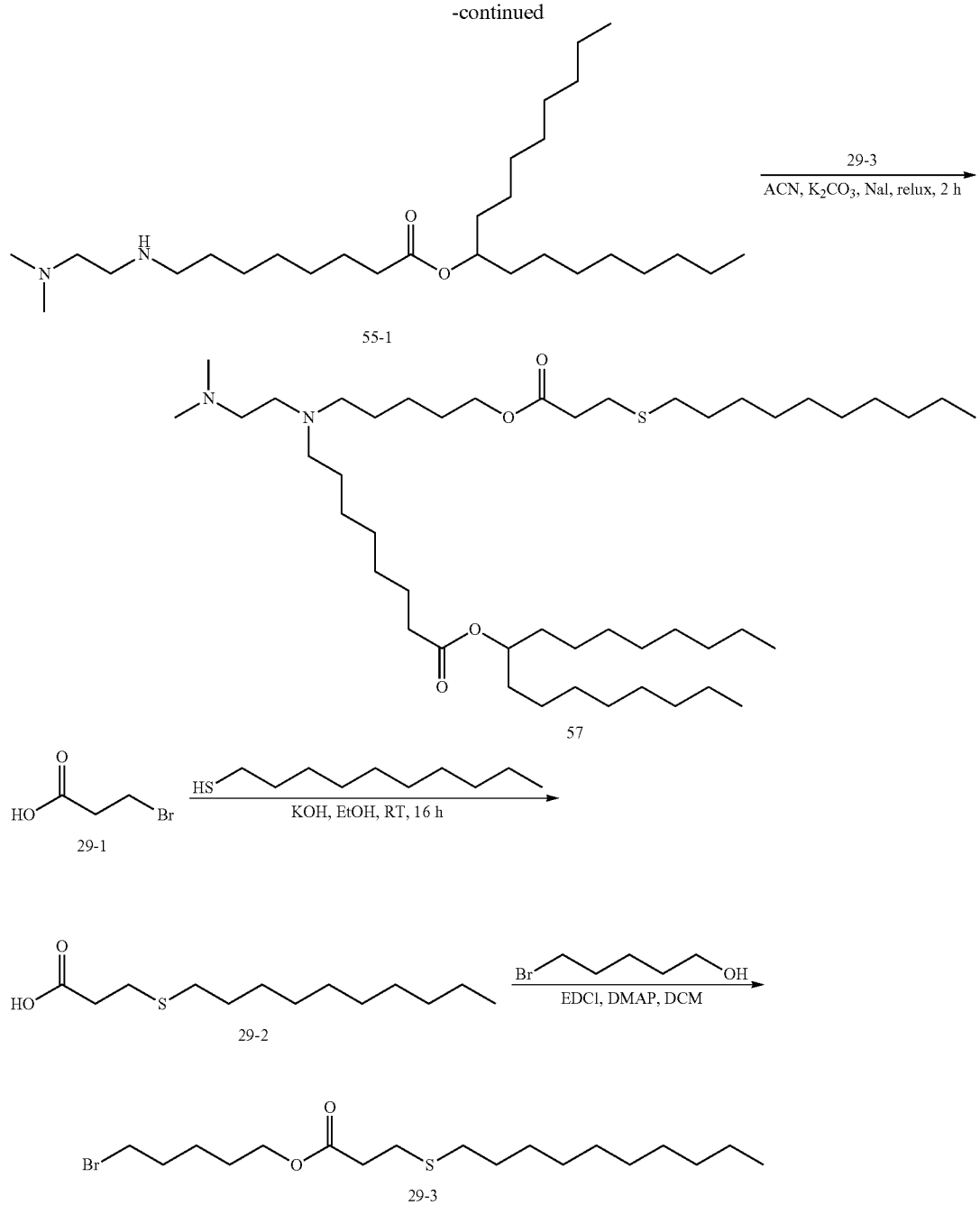

Step 1:

Compound 55-1 (500 mg) was dissolved in acetonitrile (10 ml) and stirred at room temperature. Subsequently, NaI (146 mg), $K_2CO_3$ (406 mg) and compound 29-3 (422 mg) were weighed sequentially, and added to the reaction system in batches and heated and stirred at 85° C. under reflux for 2 h. A small amount of the reaction solution was diluted and spotted on the plate (DCM/MeOH=10/1, id aqueous ammonia, phosphomolybdic acid). New spots were observed. The reaction solution was cooled to room temperature and then evaporated under reduced pressure. The sample was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min), and concentrated to give a light yellow oily liquid compound 57 (103 mg, 12% yield).

$^1$H NMR (400 MHz, Chloroform-d) δ 4.78 (s, 1H), 4.12 (s, 2H), 2.96-2.77 (m, 2H), 2.62-2.56 (m, 6H), 2.50 (s, 2H), 2.45 (d, J=2.2 Hz, 4H), 2.30 (s, 6H), 2.24 (s, 2H), 1.71-1.66 (m, 2H), 1.65 (s, 2H), 1.62 (s, 2H), 1.58 (s, 2H), 1.57-1.50 (m, 6H), 1.49 (s, 2H), 1.38 (d, J=0.8 Hz, 6H), 1.34-1.30 (m, 18H), 1.30-1.26 (m, 20H), 0.94-0.82 (m, 9H).

Example 19

Synthesis of Compound 51

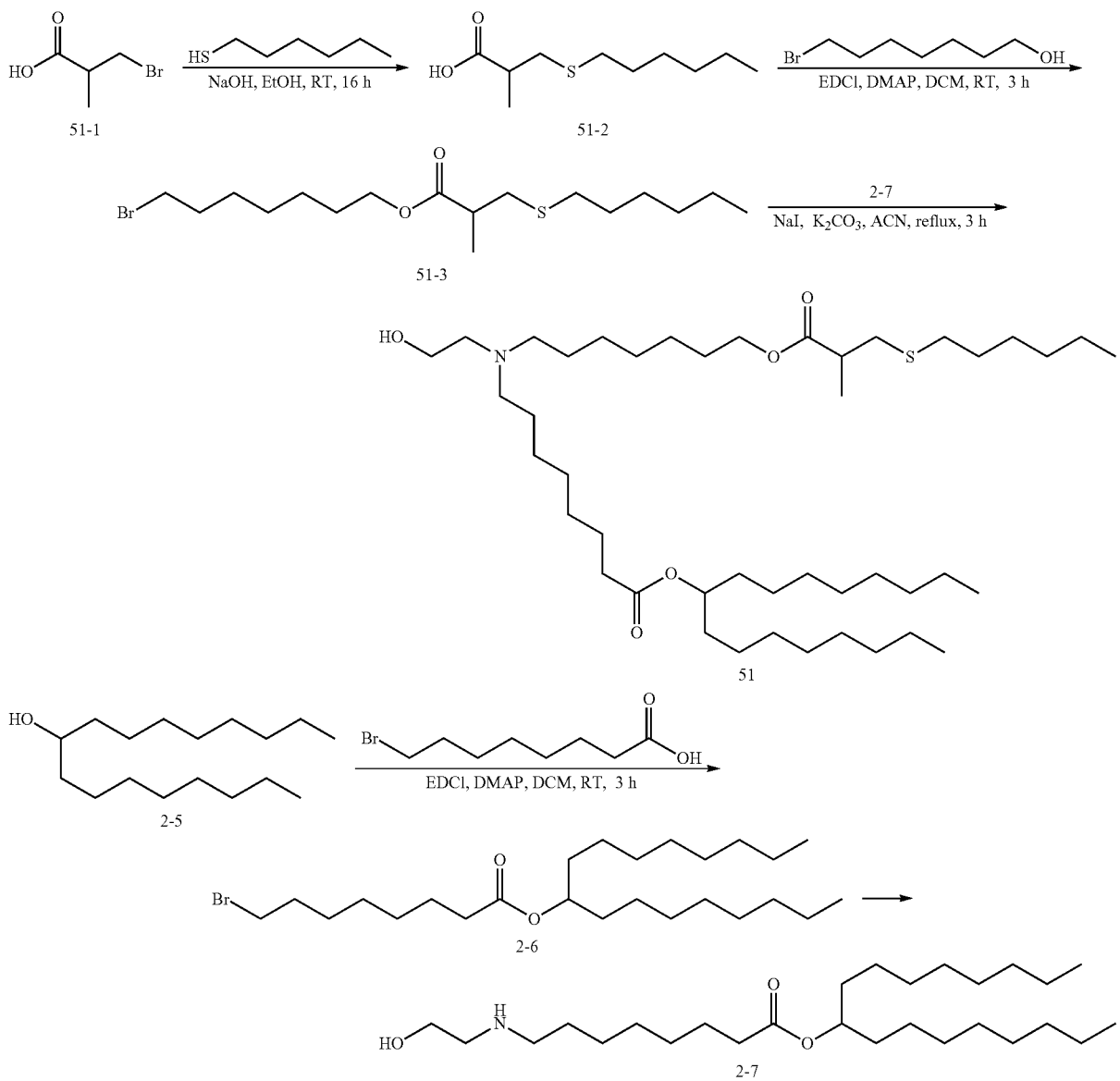

Step 1:

1-hexanethiol (2.10 g) and NaOH (2.40 g) were dissolved in ethanol (20 ml) and stirred at room temperature. Subsequently, compound 51-1 (2.00 g) was weighed and added to the reaction system in batches. The mixture was stirred overnight. TLC (PE/EA=3/1, phosphomolybdic acid) showed generation of new spots. 200 ml of water was added into the reaction mixture, and the pH was adjusted to near 3 by adding concentrated HCl dropwise. The above mixture was extracted with 600 ml of ethyl acetate, and the organic phase was dried over $Na_2SO_4$ and evaporated under reduced pressure. It was mixed with appropriate amount of DCM and silica gel, and purified (30 g normal phase column, PE/EA, 0-0% 10 min, 0-2% 20 min, 2-2% 5 min, a flow rate of 30 ml/min). The spot plate of TLC was monitored, and fractions of the pure product were evaporated to give white solid 51-2 (2.10 g, 85.8% yield).

Step 2:

Compound 51-2 (1000 mg) was dissolved in DCM (10 ml) and stirred at room temperature. 1-ethyl-(3-dimethylaminopropyl)carbodiimide hydrochloride (EDCI, 986 mg), 4-dimethylaminopyridine (DMAP, 105 mg) and 7-bromo-1-heptanol (1050 mg) were weighed sequentially, and added to the reaction system in batches and stirred at room temperature for 3 h. A small amount of the reaction solution was diluted and spotted on the plate in control with a 51-2 standard sample (PE/EA=10/1, phosphomolybdic acid). New spots with reduced polarity were observed. The reaction solution was evaporated under reduced pressure. It was mixed with appropriate amount of silica gel and DCM, and purified (10 g normal phase column, PE/EA, 0-0% 5 min, 0-5% 20 min, 5-5% 5 min, a flow rate of 15 ml/min). The spot plate of TLC was monitored, and fractions of the pure product were evaporated to give a colorless oily liquid compound 51-3 (1.40 g, 75.0% yield).

Step 3:

Compound 51-3 (750 mg) was dissolved in acetonitrile (10 ml) and stirred at room temperature. Subsequently, NaI (170 mg), K$_2$CO$_3$ (350 mg) and compound 2-7 (559 mg) were weighed sequentially, and added to the reaction system in batches and heated and stirred at 85° C. under reflux for 3 h. A small amount of the reaction solution was diluted and spotted on the plate in control with a 51-3 standard sample (DCM/MeOH=10/1, id aqueous ammonia, phosphomolybdic acid). New spots with less polarity than that of 51-3 were observed. The reaction solution was cooled to room temperature and then evaporated under reduced pressure. It was mixed with appropriate amount of DCM and silica gel, purified (25 g normal phase column, DCM/MeOH, 0.1% aqueous ammonia, 0-0% 10 min, 0-7.5% 20 min, 7.5-7.5% 5 min, a flow rate of 25 ml/min). The spot plate of TLC was monitored, and fractions of the pure product were evaporated to give a light yellow oily liquid compound 51 (740 mg, 50.7% yield).

$^1$H NMR (400 MHz, Chloroform-d) δ 4.86 (p, J=6.3 Hz, 1H), 4.09 (t, J=6.6 Hz, 2H), 3.51 (t, J=5.4 Hz, 2H), 2.82 (dd, J=12.7, 7.0 Hz, 1H), 2.65 (h, J=6.9 Hz, 1H), 2.58-2.54 (m, 3H), 2.53-2.47 (m, 2H), 2.43 (q, J=7.0 Hz, 4H), 2.27 (t, J=7.5 Hz, 2H), 1.82-1.18 (m, 53H), 0.87 (t, J=6.6 Hz, 7H).

Example 20

Luciferase mRNA was diluted in 10-100 mM citrate buffer at pH 4.0; the lipid components (cationic lipids shown in the present disclosure: DSPC:cholesterol:PEG lipids (DMG-PEG2000)) were dissolved in ethanol at a molar ratio of 50:10:38.5:1.5.

3 mL of a mRNA buffer and 1 mL of a lipid solution were loaded into two 5 mL syringes respectively, and the syringes were installed on a microfluidic syringe pump. Chips were connected to the syringes and syringe pump flow rate was set. Clicking the start button of the syringe pump caused injection into the chip at a flow rate ratio of 3:1. Under observation of the color of the product at the exit of the chip, after discarding the first 5 milky white droplets (about 100 μL), the back-end sample was collected into an EP tube. The collected product was placed in a dialysis bag and dialyzed for 6 h (MWCO: 100 KDa) in 10 mM PBS (pH 7.4) intervals. Subsequently, after being concentrated by ultrafiltration to the desired concentration, the lipid nanoparticles were filtered through a 0.22 μm sterile filter and then stored at 4° C.

Tests were performed to calculate the encapsulation rate of the products according to the instructions of Ribogreen kit. Particle size and polydispersity index (PDI) detection as well as zeta potential analysis was performed on a Malvern Zetasizer nano instrument using standard assays.

The results of particle size, PDI and encapsulation rate of LNP loaded with mRNA prepared in this example are shown in Table 1. The results indicate that the nanoparticles formed by lipids and mRNA under this formulation had a high encapsulation rate and a uniform particle size of about 100 nm, which conformed to the basic characteristics of carriers for delivering nucleic acids.

TABLE 1

Characterization results of nanoparticles prepared from different cationic lipids

| No. | Cationic lipid | Encapsulation rate (%) | Particle size (nm) | PDI | Zeta potential (mV) |
|---|---|---|---|---|---|
| 1 | Compound 2 | 87.8 | 97.3 | 0.12 | 0.49 |
| 2 | Compound 3 | 87.5 | 113.9 | 0.10 | 1.95 |
| 3 | Compound 4 | 83.7 | 94.4 | 0.21 | 0.39 |
| 4 | Compound 6 | 63.9 | 95.6 | 0.17 | 0.79 |
| 5 | Compound 7 | 96.1 | 78.9 | 0.17 | −3.77 |
| 6 | Compound 14 | 95.7 | 119.0 | 0.22 | −3.27 |
| 7 | Compound 17 | 92.5 | 90.9 | 0.10 | −0.15 |
| 8 | Compound 28 | 95.9 | 127.6 | 0.04 | 5.29 |
| 9 | Compound 29 | 95.6 | 105.5 | 0.03 | −1.31 |
| 10 | Compound 30 | 95.7 | 121.2 | 0.11 | −0.26 |
| 11 | Compound 35 | 90.4 | 104.5 | 0.11 | −2.10 |
| 12 | Compound 36 | 93.9 | 98.4 | 0.11 | 0.55 |
| 13 | Compound 41 | 94.9 | 123.4 | 0.17 | −7.02 |
| 14 | Compound 44 | 96.4 | 104.1 | 0.21 | −2.82 |
| 15 | Compound 46 | 95.6 | 101.3 | 0.11 | −4.12 |
| 16 | Compound 48 | 92.5 | 94.2 | 0.10 | −0.14 |
| 17 | Compound 55 | 91.1 | 102.3 | 0.13 | 7.37 |
| 18 | Compound 57 | 94.1 | 122.8 | 0.24 | 7.09 |
| 19 | DLin-MC3-DMA* | 87.6 | 102.3 | 0.19 | −0.03 |
| 20 | Lipid M** | 98.5 | 145.3 | 0.14 | −0.53 |

*DLin-MC3-DMA is a cationic lipid for the commercial nucleic acid delivery system Onpattro.
**Lipid M in Table 1 is from "Optimization of Lipid Nanoparticles for Intramuscular Administration of mRNA Vaccines", Mol Ther Nucleic Acids 2019 Vol. 15 Pages 1-11, and is the same type of lipid as SM-102.

Example 21—Determination of the Effect of Delivering Luciferase mRNA for In Vivo Expression by Tail Intravenous Injection Using Nano-Lipid Particle Compositions LUC-mRNA-lipid nanoparticles containing 5 μg mRNA (see SEQ ID NO: 1 in the Patent Application Publication CN114380724A for the corresponding nucleotide sequence of LUC-mRNA) were injected via tail intravenous injection in 6-8 week old female BALB/c mice, prepared as in Example 19. 100 μg of D-Luciferin Potassium Salt was injected via tail intravenous injection into the mice at specific time points and assayed using the PerkinElmer Small Animal Imaging System. Fluc is commonly used in mammalian cell cultures to measure gene expression and cell viability, and it emits biological fluorescent light in the presence of the substrate fluorescein. The basic characteristics of the mRNA used include ARCA cap structure, polyA tail length of 120 nt, and complete substitution of pseudouridine. The results of the assay are shown in FIG. 1, wherein most of nano-lipid particle compositions comprising compounds designed in the present disclosure deliver mRNA to the liver at levels equivalent or superior to DLin-MC3-DMA, while some compounds are superior to Lipid M.

Figure 2:
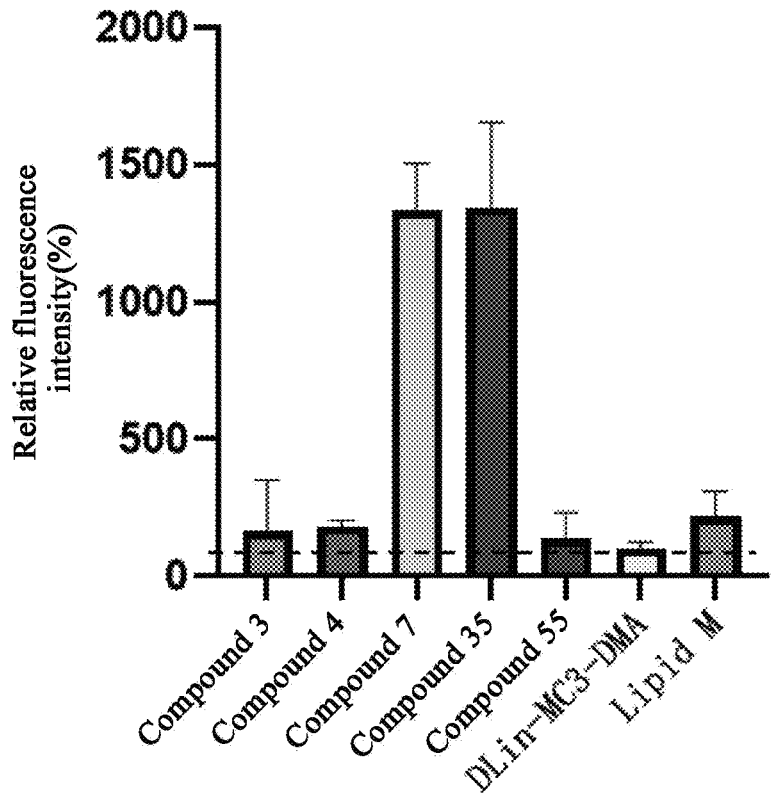
FIG. 2 shows the in vivo imaging relative fluorescence intensity of mice with lung nebulized delivery of Example 22.

Example 22—Determination of the Effect of Delivering Luciferase mRNA for In Vivo Expression by Lung Nebulization Using Nano-Lipid Particle Compositions LUC-mRNA-lipid nanoparticles containing 5 μg mRNA were administrated via lung nebulization in 6-8 week old BALB/c mice, prepared as in Example 19. 100 μg of D-Luciferin Potassium Salt was injected via tail intravenous injection into the mice at specific time points and assayed using the PerkinElmer Small Animal Imaging System. The results of the assay are shown in FIG. 2, wherein nano-lipid particle compositions comprising Compounds 7 and 35 deliver mRNA for expression at fluorescent levels superior to Lipid M and SM-102.

Figure 3:
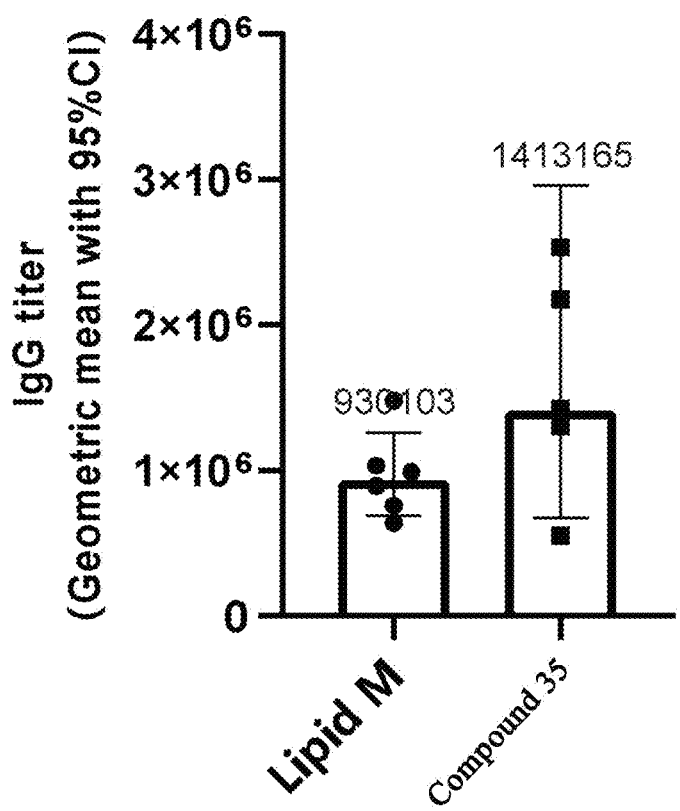
FIG. 3 shows the binding antibody titer of Example 23.

Example 23—Delivery of Novel Coronavirus mRNA Vaccines Using Nano-Lipid Particle Compositions In 6-week BALB/c mice, mRNA neocoronavirus vaccines (Omicron antigen mRNA, see SEQ ID NO:6 in Patent Publication CN114380724A for corresponding nucleotide sequences) delivered by various nano-lipid particle compositions were injected intramuscularly for immunization on days 0 and 14. Blood samples were collected on day 28 (day 14 after the secondary immunization) and the binding antibody titer was measured by enzyme-linked immunosorbent assay to evaluate the protective effect of the mRNA neocoronavirus vaccine delivered by various nano-lipid particle compositions against infection by SARS-CoV-2 strains. The results are shown in FIG. 3. From the results, it can be seen that the binding antibody titer induced by the nano-lipid particle compositions comprising Compound 35 delivering the neocoronavirus mRNA was 1.4 million, while that of Lipid M was about 930 thousand.

Figure 4:
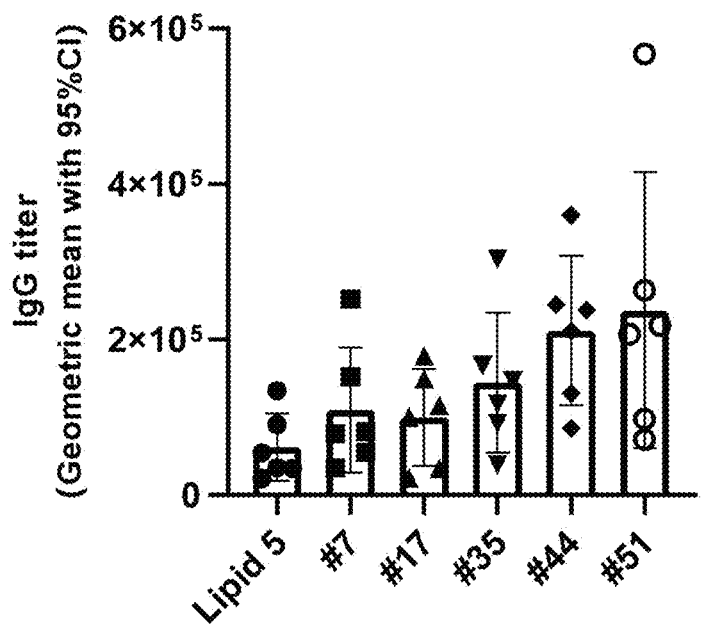
FIG. 4 shows the binding antibody titer of Example 24.

Example 24—Pulmonary Delivery of Novel Coronavirus mRNA Vaccines Using Nano-Lipid Particle Compositions Additional lipid nanoparticles were prepared in accordance with Example 20 to validate their immunization effect of the novel coronavirus mRNA vaccines via pulmonary delivery. Using 8-week BALB/c mice, mRNA neocoronavirus vaccines (Omicron antigen mRNA, see SEQ ID NO:6 in Patent Publication CN114380724A for corresponding nucleotide sequences) delivered by various nano-lipid particle compositions were nebulized to lung for immunization on day 0. Blood samples were collected on day 14 and the binding antibody titer was measured by enzyme-linked immunosorbent assay to evaluate the protective effect of the mRNA neocoronavirus vaccine delivered by various nano-lipid particle compositions against infection by SARS-CoV-2 strains (the results are shown in FIG. 4). From the results, it can be seen that the compounds of the present application caused a rise in binding antibody titer superior to that of Lipid 5.

Example 25—Characterization of Nano-Lipid Particle Compositions with Various Lipid Components and Ratios An experimental design was developed for Compound 35 to investigate the druggability with various auxiliary lipids and in various lipid ratios. Attempts were made to prepare nanoparticles by mixing lipid mixtures of various structural lipids (DOPE, DSPC), various lipid ratios (cation 45-55%, PEG lipids 1.5-2.5%, structural lipids 8-22%, cholesterol 20.5-45.5%) and various nitrogen-phosphorus ratios (5-10) with Luc mRNA by microfluidization (same method as Example 19). The results are shown in Table 2.

TABLE 2

Characterization results of nanoparticles prepared with various lipid ratios (molar ratios)

| No. | Compound 35 | DMG-PEG2000 | DSPC | cholesterol | N/P | Particle size(nm) | PDI | Encapsulation rate (%) |
|---|---|---|---|---|---|---|---|---|
| 1 | 55 | 2.5 | 22 | 20.5 | 5 | 100.5 | 0.193 | 85.78 |
| 2 | 45 | 1.5 | 22 | 31.5 | 10 | 98.13 | 0.121 | 96.98 |
| 3 | 45 | 2.5 | 8 | 44.5 | 5 | 70.02 | 0.138 | 97.38 |
| 4 | 45 | 1.5 | 8 | 45.5 | 10 | 98.19 | 0.121 | 96.70 |
| 5 | 50 | 1.5 | 15 | 33.5 | 7.5 | 85.09 | 0.051 | 96.10 |
| 6 | 55 | 1.5 | 15 | 28.5 | 10 | 93.83 | 0.122 | 94.46 |

| No. | Compound 35 | DMG-PEG2000 | DOPE | cholesterol | N/P | Particle size(nm) | PDI | Encapsulation rate (%) |
|---|---|---|---|---|---|---|---|---|
| 7 | 55 | 2.5 | 22 | 20.5 | 5 | 145.0 | 0.169 | 90.26 |
| 8 | 45 | 1.5 | 22 | 31.5 | 10 | 114.9 | 0.205 | 94.11 |
| 9 | 45 | 2.5 | 8 | 44.5 | 5 | 92.41 | 0.173 | 94.62 |
| 10 | 45 | 1.5 | 8 | 45.5 | 10 | 113.7 | 0.233 | 96.36 |
| 11 | 50 | 1.5 | 15 | 33.5 | 7.5 | 140.2 | 0.155 | 92.54 |
| 12 | 55 | 1.5 | 15 | 28.5 | 10 | 129.1 | 0.190 | 96.16 |

As can be seen from the results in Table 2, the nanoparticles formed from the lipid mixture and mRNA in this range have uniform particle size, high encapsulation rate, and good druggability.

Example 26—Study of In Vivo Expression Effect of Luciferase mRNA Delivered by Different Cations The effect of delivering luciferase mRNA using more cationic lipids were validated according to the methods of Example 20 and Example 21. Table 3 below shows the characterization results.

TABLE 3

| No. | Cationic lipid | Encapsulation rate (%) | Particle size (nm) | PDI | relative fluorescence intensity (%) |
|---|---|---|---|---|---|
| 1 | Compound 7 | 96.8 | 82.9 | 0.15 | 754 ± 32 |
| 2 | Compound 16 | 95.6 | 90.9 | 0.20 | 574 ± 102 |
| 3 | Compound 17 | 97.6 | 68.2 | 0.11 | 686 ± 45 |
| 4 | Compound 23 | 97.0 | 75.4 | 0.10 | 764 ± 39 |
| 5 | Compound 35 | 96.2 | 80.4 | 0.14 | 962 ± 78 |
| 6 | Compound 44 | 97.1 | 71.1 | 0.10 | 843 ± 52 |
| 7 | Compound 45 | 96.8 | 80.9 | 0.15 | 559 ± 33 |
| 8 | Compound 51 | 98.0 | 91.0 | 0.11 | 734 ± 51 |
| 9 | DLin-MC3-DMA | 0.2 | 101.5 | 0.16 | 100 |

Note:
Due to different experimental batches, the encapsulation rate, particle size and DPI data in Table 3 are slightly different from those in Table 1.

As can be seen from the above table, the above compounds have high encapsulation rate and homogeneous particle size, and the efficiency of in vivo delivery of Luciferase mRNA is much higher than that of commercial lipid DLin-MC3-DMA.

Example 27—Study of Protein Expression Efficiency of Various Cationic Lipids

In the example, the effects of in vivo transfection of erythropoietin (EPO) by various cationic liposomes were compared. Nanoparticles were prepared in the same manner as in Example 20, and the nucleotide sequence corresponding to the EPO mRNA used is given in CN114380724B, SEQ ID NO:2. After preparation, 20 μg of EPO-mRNA-lipid nanoparticles were injected via tail intravenous injection in 6-8 week female Balb/c mice. 6 hours later the mice were subjected to blood sampling from the eye frame. After centrifugation to separate the serum, EPO protein expression was determined using ELISA. The basic characteristics of the mRNA used include ARCA cap structure, polyA tail length of 100-120 nt, and complete substitution of pseudouridine. The preparation and protein assay results are shown in Table 4.

TABLE 4

| No. | Cationic lipid | Encapsulation rate (%) | Particle size (nm) | PDI | EPO concentration (pg/mL) |
|---|---|---|---|---|---|
| 1 | Compound 7 | 97.8 | 88.8 | 0.09 | $4.21 \times 10^7$ |
| 2 | Compound 16 | 96.5 | 75.4 | 0.12 | $3.01 \times 10^7$ |
| 3 | Compound 17 | 96.9 | 74.0 | 0.09 | $3.25 \times 10^7$ |
| 4 | Compound 23 | 96.5 | 81.7 | 0.11 | $4.11 \times 10^7$ |
| 5 | Compound 35 | 96.1 | 79.1 | 0.12 | $5.73 \times 10^7$ |
| 6 | Compound 44 | 95.5 | 82.5 | 0.17 | $4.89 \times 10^7$ |
| 7 | Compound 45 | 93.9 | 81.0 | 0.15 | $3.46 \times 10^7$ |
| 8 | Compound 51 | 95.0 | 75.3 | 0.14 | $6.68 \times 10^7$ |
| 9 | DLin-MC3-DMA | 90.1 | 97.6 | 0.19 | $4.37 \times 10^6$ |

Note:
Due to different experimental batches, the encapsulation rate, particle size and DPI data in Table 4 are slightly different from those in Tables 1 and 3.

As can be seen from the above table, the above compounds have high encapsulation rate and homogeneous particle size, and the in vivo protein translation efficiency for delivery of EPO mRNA is much higher than that of commercial lipid DLin-MC3-DMA.

Example 28—Study on the Abnormal Toxicity of Various Cationic Lipids

Figure 5:
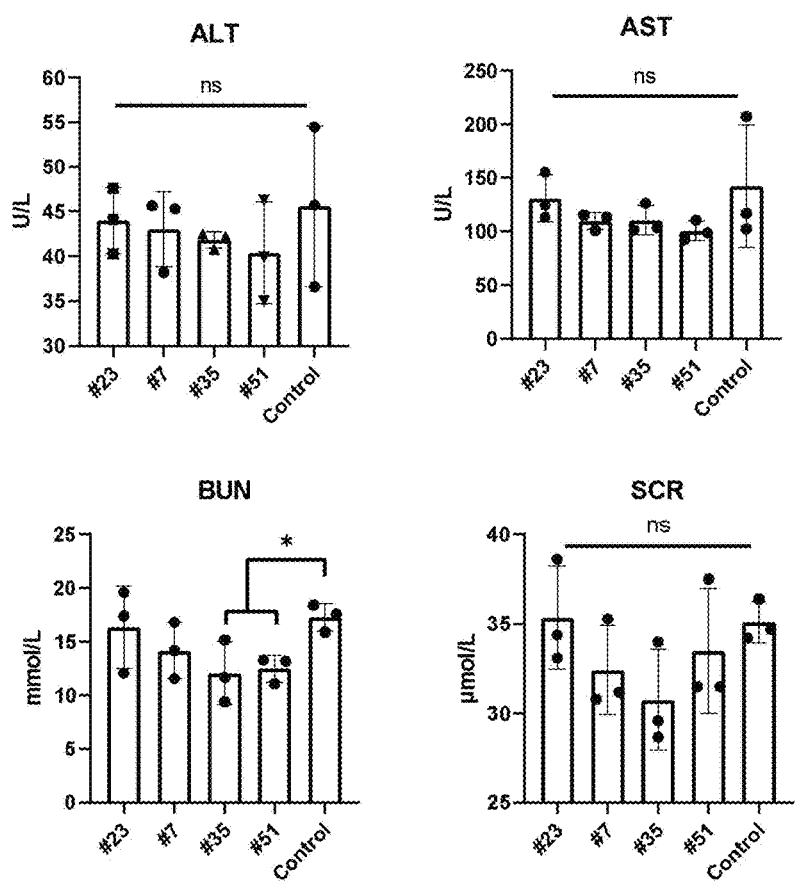
FIG. 5 shows a graph for liver and kidney function evaluation of Example 25.

The nanoparticles prepared in Example 27 were used in this experiment. The nanoparticles were injected via tail intravenous injection at a dose of 5 mg/kg in female SD rats weighing 200-250 g. The mice in the control group were injected with a corresponding volume of normal saline. The mice in the DLin-MC3-DMA group died within 18 h after injection, while the weight, feeding and activity status of the remaining mice showed no abnormalities during the observation period. This indicated that DLin-MC3-DMA lipids were more toxic. Blood samples were collected at 120 h after injection, and alanine transaminase (ALT), aspartate aminotransferase (AST), urea nitrogen (BUN), and serum creatinine (SCR) were measured using a fully automated biochemistry instrument as the evaluation indexes of hepatic and renal functions. The results in FIG. 5 show that the rest of the indicators of lipid nanoparticles did not fluctuate significantly, except for a slight decrease in the BUN values of Compound 35 and Compound 51 (but the values were within the healthy normal range). This suggests that the cationic lipids do not affect liver and kidney function, have low toxicity, and are suitable for use in protein replacement pipelines.

Figure 6:
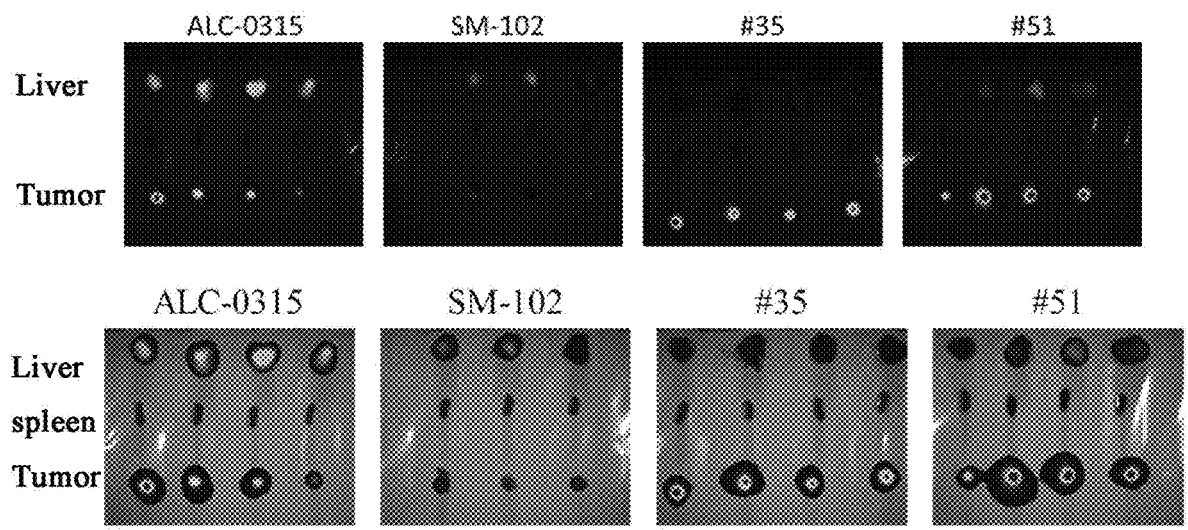
FIG. 6 shows the fluorescence imaging graph of Example 28.
Figure 7:
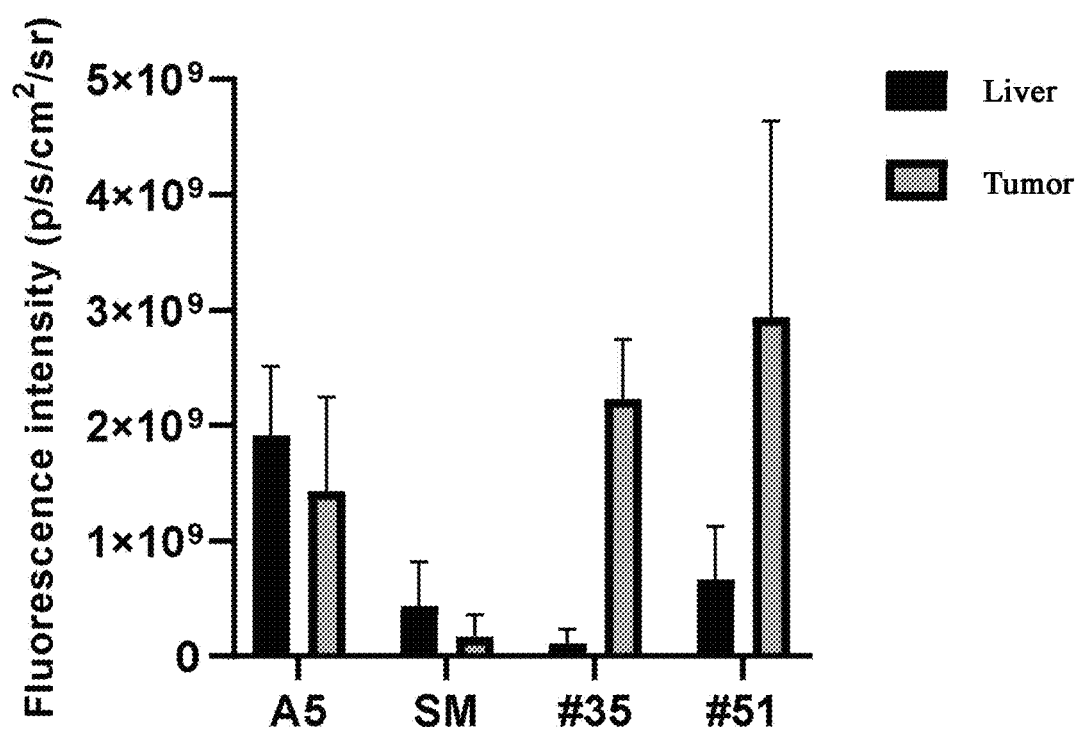
FIG. 7 shows the statistical values of the fluorescence imaging results of Example 28.

Example 29—Comparison of the Effect of Intratumoral Injection of Various Nanolipid Particle Compositions Different types of lipid nanoparticles encapsulating luciferase mRNA in were prepared accordance with the preparation of Example 20. Tumors were injected subcutaneously in the right abdomen of 6-8 week female $C_{57}BL6$ mice at $5 \times 10^5$ B 16F 10 cells (from CAS Cell Bank, CSTR:19375.09.3101MOUTCM36)/mouse, and tumor growth was observed and recorded periodically. On the 8th day after tumor inoculation, the length (L, mm) and width (D, mm) of the tumors were measured by using a vernier caliper, and the tumor volume (V) was calculated according to the formula $V=(L \times D^2)/2$. Mice with tumor volume in the range of 80-120 mm³ were taken and randomly grouped, and intratumorally injected with different types of lipid nanoparticles encapsulating luciferase mRNA at the volume of 25 μL/2.5 μg. Anatomical imaging was performed after 24 h to detect the fluorescence intensity of the mouse liver and tumor (as shown in FIGS. 6 and 7). The results showed that Compounds 35 and 51 had higher brightness at the tumor and lower brightness in the liver. This indicates better in situ tumor expression and lower liver metastasis, which is suitable for encapsulation and delivery of some tumor therapy-related nucleic acid drugs.

The invention claimed is:

1. A cationic lipid compound having the following structures:

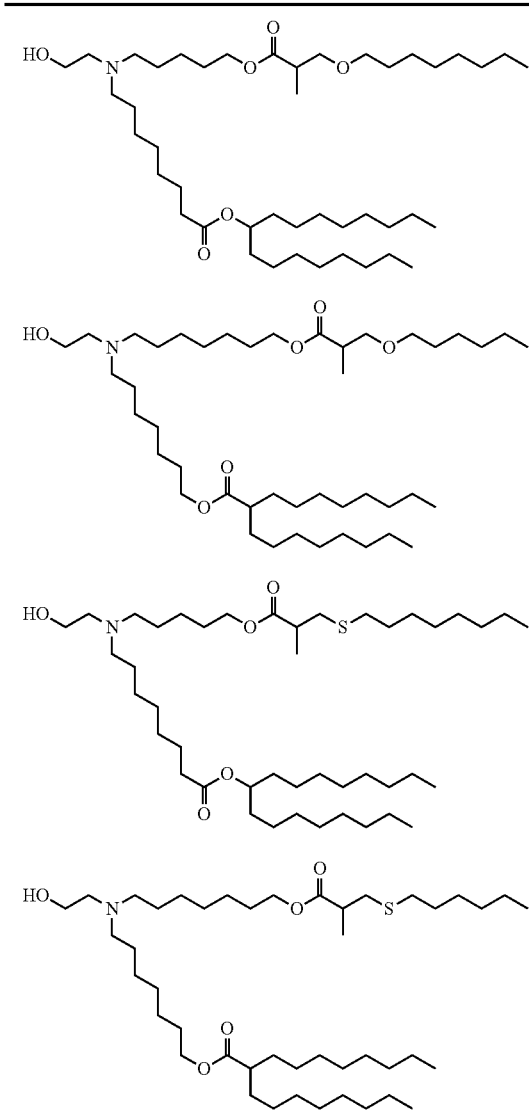

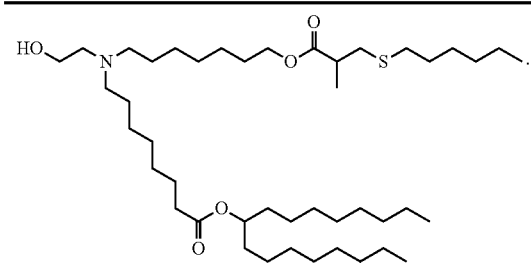

2. A liposomal formulation comprising the cationic lipid compound according to claim 1 and a prophylactic or therapeutic nucleic acid, wherein the liposomal formulation is used for prevention or treatment of diseases.

3. The liposomal formulation according to claim 2, wherein the molar ratio of the nucleic acid to the cationic lipid compound is from 20:1 to 1:1.

4. The liposomal formulation according to claim 2, wherein the liposomal formulation has a diameter of 50 nm to 300 nm.

5. The liposomal formulation according to claim 2, further comprising one or more other lipid components, including a neutral lipid, a steroid and a polymer-conjugated lipid.

6. The liposomal formulation according to claim 5, wherein the included steroid is cholesterol.

7. The liposomal formulation according to claim 6, wherein the molar ratio of the cholesterol to the cationic lipid compound is (0-1.5):1.

8. The liposomal formulation according to claim 5, wherein the polymer in the polymer-conjugated lipid is polyethylene glycol (PEG).

9. The liposomal formulation according to claim 8, wherein the molar ratio of the cationic lipid compound to the polyethylene glycol-conjugated lipid is from 100:1 to 20:1.

10. The liposomal formulation according to claim 5, wherein the neutral lipid is selected from one or more of DSPC, DPPC, DMPC, DOPC, POPC, DOPE, and SM.

11. The liposomal formulation according to claim 10, wherein the molar ratio of the neutral lipid to the cationic lipid compound is (0-0.5):1.

12. The liposomal formulation according to claim 2, wherein the nucleic acid is selected from antisense RNA and/or messenger RNA.

13. A method for inducing protein expression in a subject, wherein, the method comprises administering the cationic lipid compound according to claim 1 to the subject.

* * * * *

SEQUENCE LISTING

```
Sequence total quantity: 2
SEQ ID NO: 1            moltype = DNA   length = 1653
FEATURE                 Location/Qualifiers
misc_feature            1..1653
                        note =          Luciferase
source                  1..1653
                        mol_type = other DNA
                        organism = synthetic construct
SEQUENCE: 1
atggaggatg ctaagaatat caagaagggt ccagccccat tttacccgct ggaagacgga    60
acggctggcg agcagctcca caaggcaatg aaaaggtacg ccttagtgcc tggcacgatc   120
gcttttacag acgcccatat tgaggtcaat attacgtatg ctgagtattt cgagatgagt   180
gtgagacttg cagaggccat gaagcgttac gggctcaaca ctaatcatcg tatagtggtg   240
tgttcagaaa actctctgca attcttcatg ccggtcttag gagcgctctt cataggagtg   300
gcagttgcgc cagcgaatga catatataac gagcgcgagt tgctgaactc tatgaatatt   360
```

-continued

```
tcacagccaa cggtcgtttt cgtatccaaa aaaggcctac aaaagatcct caacgtacaa  420
aaaaaactgc ctatcataca aaaaattatt attatggact cgaagaccga ctatcaaggg  480
tttcaaagca tgtacacgtt cgttactagc catctccctc caggcttcaa tgaatacgac  540
ttcgtgcctg aatcattcga ccgtgacaaa accatagccc tgatcatgaa ctcatcggga  600
agcacgggct taccaaaagg tgtggcgctt ccacacagga ctgcttgtgt aagatttagt  660
catgccagag atcccatctt tggaaatcaa atcattccag acactgccat tcttagtgtc  720
gtaccgttcc atcatggttt cggaatgttc acgactttgg gctatttaat ttgtggtttc  780
cgcgttgttt tgatgtatag gttcgaagag gaactgttcc tgagatcatt acaggactat  840
aagatccaga gcgccctact cgttccgacg ctattttcct tttcgcgaa atcgaccctc  900
attgacaaat acgatctgtc taacctacat gagattgcta gtgggggtgc gcccctaagc  960
aaagaggttg gtgaagcggt ggcgaagcga tttcatctgc ctggaatacg gcaagggtac  1020
ggtttaaccg aaaccacatc ggccatcttg ataacgccag aaggggacga caagccggga  1080
gctgtaggta aggttgttcc attcttcgaa gcgaaagtgg tggacttgga cactggaaag  1140
accttagggg ttaatcaacg tggggagctg tgcgtcagag gcccgatgat catgtctggg  1200
tacgttaaca accctgaagc aacgaatgcc ttaattgata aggacgggtg gttgcactcg  1260
ggtgacatag cctactggga cgaagacgaa cactttttca ttgtggatcg tctgaagtcc  1320
ctgattaaat ataaaggcta tcaagtggcc ccagcggagc tcgaatctat tttgctgcaa  1380
cacccgaaca tcttcgatgc gggcgttgca ggtctgccag acgatgatgc gggagagctc  1440
ccggctgcag ttgttgtcct tgagcatggg aagactatga cggaaaaaga aatcgttgat  1500
tatgtggcat cgcaagtaac caccgccaag aagctacgtg gtggggtggt cttcgtggat  1560
gaggtaccca aaggtctgac tggaaaacta gacgctcgga aaattcgcga gattctcatc  1620
aaggcgaaaa aaggtggaaa aagcaagcta tga                               1653

SEQ ID NO: 2           moltype = DNA  length = 3822
FEATURE                Location/Qualifiers
misc_feature           1..3822
                       note =        COVID-19 Spike
source                 1..3822
                       mol_type = other DNA
                       organism = synthetic construct
SEQUENCE: 2
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcaccgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctgggcgtgt actaccacaa gaacaacaag agctggatgg agagcgagtt ccgggtgtac  480
agcagcgcca acaactgcac cttcgagtac gtgagccagc ccttcctgat ggacctggag  540
ggcaagcagg gcaacttcaa gaacctgcgg gagttcgtgt tcaagaacat cgacggctac  600
ttcaagatct acagcaagca caccccaatc aacctggtgc gggatctgcc ccagggcttc  660
tcagccctgg agcccctggt ggacctgccc atcggcatca acatcacccg gttccagacc  720
ctgctggccc tgcaccggag ctacctgacc ccaggcgaca gcagcagcgg gtggacagca  780
ggcgcggctg cttactacgt gggctacctg cagccccgga ccttcctgct gaagtacaac  840
gagaacggca ccatcaccga cgccgtggac tgcgccctgg accctctgag cgagaccaag  900
tgcaccctga agagcttcac cgtggagaag ggcatctacc agaccagcaa cttccgggtg  960
cagcccaccg agagcatcgt gcggttcccc aacatcacca acctgtgccc cttcggcgag  1020
gtgttcaacg ccacccggtt cgccagcgtg tacgcctgga accggaagcg gatcagcaac  1080
tgcgtggccg actacagcgt gctgtacaac agcgccagct tcagcacctt caagtgctac  1140
ggcgtgagcc ccaccaagct gaacgacctg tgcttcacca acgtgtacgc cgacagcttc  1200
gtgatccgtg gcgacgaggt gcggcagatc gcacccggcc agacaggcaa gatcgccgac  1260
tacaactaca agctgcccga cgacttcacc ggctgcgtga tcgcctggaa cagcaacaac  1320
ctcgacagca aggtgggcgg caactacaac tacctgtacc ggctgttccg gaagagcaac  1380
ctgaagccct tcgagcggga catcagcacc gagatctacc aagccggctc cacccccttgc  1440
aacggcgtgg agggcttcaa ctgctacttc cctctgcaga gctacggctt ccagcccacc  1500
aacggcgtgg gctaccagcc ctaccgggtg gtggtgctga gcttcgagct gctgcacgcc  1560
ccagccaccg tgtgtggccc caagaagagc accaacctgg tgaagaacaa gtgcgtgaac  1620
ttcaacttca acggccttac cggcaccggc gtgctgaccg agagcaacaa gaaattcctg  1680
ccctttcagc agttcggccg ggacatcgcc gacaccaccg acgctgtgcg ggatccccag  1740
accctggaga tcctggacat caccccttgc agcttcggcg gcgtgagcgt gatcacccca  1800
ggcaccaaca ccagcaacca ggtggccgtg ctgtaccagg acgtgaactg caccgaggtg  1860
cccgtggcca tccacgccga ccagctgaca cccacctggc gggtctacag caccggcagc  1920
aacgtgttcc agacccgggc cggttgcctg atcggcgccg agcacgtgaa caacagctac  1980
gagtgcgaca tccccatcgg cgccggcatc tgtgccagct accagaccca gaccaattca  2040
ccccggaggg caaggagcgt ggccagccag agcatcatcg cctacaccat gagcctgggc  2100
gccgagaaca gcgtggccta cagcaacaac agcatcgcca tccccaccaa cttcaccatc  2160
agcgtgacca ccgagattct gcccgtgagc atgaccaaga ccagcgtgga ctgcaccatg  2220
tacatctgcg gcgacagcac cgagtgcagc aacctgctgc tgcagtacgg cagcttctgc  2280
acccagctga accgggccct gaccggcatc gccgtggagc aggacaagaa cacccaggag  2340
gtgttcgccc aggtgaagca gatctacaag acccctccca tcaaggactt cggcggcttc  2400
aacttcagcc agatcctgcc cgaccccagc aagcccagca agcggagctt catcgaggac  2460
ctgctgttca acaaggtgac cctagccgac gccggcttca tcaagcagta cggcgactgc  2520
ctcggcgaca tagccgcccg ggacctgatc tgcgcccaga agttcaacgg cctgaccgtg  2580
ctgcctcccc tgctgaccga cgagatgatc gcccagtaca ccagcgccct gttagccgga  2640
accatcacca gcggctggac tttcggcgct ggagccgctc tgcagatccc cttcgccatg  2700
cagatggcct accggttcaa cggcatcggc gtgacccaga acgtgctgta cgagaaccag  2760
aagctgatcg ccaaccagtt caacagcgcc atcggcaaga tccaggacag cctgagcagc  2820
accgctagcg ccctgggcaa gctgcaggac gtggtgaacc agaacgccca ggccctgaac  2880
```

```
accctggtga agcagctgag cagcaacttc ggcgccatca gcagcgtgct gaacgacatc  2940
ctgagccggc tggaccctcc cgaggccgag gtgcagatcg accggctgat cactggccgg  3000
ctgcagagcc tgcagaccta cgtgacccag cagctgatcc gggccgccga gattcgggcc  3060
agcgccaacc tggccgccac caagatgagc gagtgcgtgc tgggccagag caagcgggtg  3120
gacttctgcg gcaagggcta ccacctgatg agctttcccc agagcgcacc ccacggagtg  3180
gtgttcctgc acgtgaccta cgtgcccgcc caggagaaga acttcaccac cgccccagcc  3240
atctgccacg acggcaaggc ccactttccc cgggagggcg tgttcgtgag caacggcacc  3300
cactggttcg tgacccagcg gaacttctac gagcccagat catcaccac cgacaacacc  3360
ttcgtgagcg gcaactgcga cgtggtgatc ggcatcgtga acaacaccgt gtacgatccc  3420
ctgcagcccg agctggacag cttcaaggag gagctggaca agtacttcaa gaatcacacc  3480
agccccgacg tggacctggg cgacatcagc ggcatcaacg ccagcgtggt gaacatccag  3540
aaggagatcg atcggctgaa cgaggtggcc aagaacctga acgagagcct gatcgacctg  3600
caggagctgg gcaagtacga gcagtacatc aagtggccct ggtacatctg gctgggcttc  3660
atcgccggcc tgatcgccat cgtgatggtg accatcatgc tgtgctgcat gaccagctgc  3720
tgcagctgcc tgaagggctg ttgcagctgc ggcagctgct gcaagttcga cgaggacgac  3780
agcgagcccg tgctgaaggg cgtgaagctg cactacacct ga                     3822
```